United States Patent [19]
Büchel et al.
[11] Patent Number: 4,994,480
[45] Date of Patent: Feb. 19, 1991

[54] FUNGICIDAL SUBSTITUTED TRIAZOLYLMETHYLCARBINOLS

[75] Inventors: Karl H. Büchel, Burscheid; Graham Holmwood, Wuppertal; Gerd Hännsler, Leverkusen; Wilhelm Brandes, Leichlingen; Stefan Dutzmann, Duesseldorf, all of Fed. Rep. of Germany

[73] Assignee: Bayer Aktiengesellschaft, Leverkusen, Fed. Rep. of Germany

[21] Appl. No.: 337,201

[22] Filed: Apr. 12, 1989

[30] Foreign Application Priority Data

Apr. 20, 1988 [DE] Fed. Rep. of Germany ....... 3813253

[51] Int. Cl.⁵ .................. C07D 249/08; A01N 43/653

[52] U.S. Cl. .................................... 514/383; 514/184; 548/101; 548/267.8; 548/268.6

[58] Field of Search ...................... 548/101, 262, 267.8, 548/268.6; 546/276; 544/333, 340; 514/184, 256, 383

[56] References Cited

U.S. PATENT DOCUMENTS 4,584,308 4/1986 Elbe et al. ........................... 514/383
4,723,984 2/1988 Holmwood et al. ................... 71/76

FOREIGN PATENT DOCUMENTS 061835 10/1982 European Pat. Off. ............ 514/383
091398 7/1983 European Pat. Off. ............ 548/262

*Primary Examiner*—Glennon H. Hollrah
*Assistant Examiner*—Patricia L. Morris
*Attorney, Agent, or Firm*—Sprung Horn Kramer & Woods

[57] ABSTRACT

Fungicidal substituted triazolylmethylcarbinols of the formula

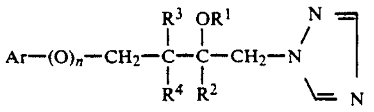

(I)

in which n stands for the numbers 0 or 1,

Ar stands for optionally substituted phenyl or for optionally substituted naphthyl, $R^1$ stands for hydrogen, optionally substituted alkyl, optionally substituted alkenyl, optionally substituted alkinyl, optionally substituted aralkyl, cycloalkyl or optionally substituted heteroarylalkyl, $R^2$ stands for alkyl, cycloalkyl, cycloalkylalkyl or alkenyl, $R^3$ stands for methyl and $R^4$ stands for methyl or $R^3$ and $R^4$ together stand for ethane-1,2-diyl, and addition products thereof with acids and metal salts. Intermediates of the formulas

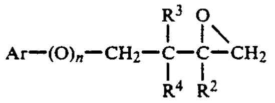

(V)

and

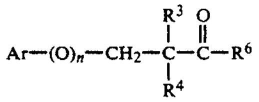

(VII-a)

in which $R^6$ stands for alkyl having more than one carbon atom, cycloalkyl, cycloalkylalkyl or alkenyl, are also new.

14 Claims, No Drawings

FUNGICIDAL SUBSTITUTED TRIAZOLYLMETHYLCARBINOLS

The present invention relates to new substituted triazolylmethylcarbinols, several processes for their preparation and their use as fungicides.

It has already been disclosed that certain triazolylmethylcarbinols exhibit fungicidal properties (cf. EP-OS (European Published Specification) No. 0,040,345). Thus, for example, it is possible to employ 1-(4-chlorophenyl)-4-methyl-3-(1,2,4-triazol-1-yl-methyl)-pentan-3-ol for combating fungi. However, the action of this substance is not always satisfactory, above all when it is used at low application rates.

New substituted triazolylmethylcarbinols of the formula

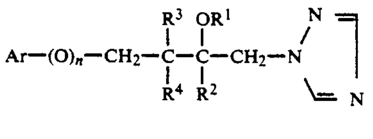

(I)

in which n stands for the numbers 0 or 1,

Ar stands for optionally substituted phenyl or for optionally substituted naphthyl, $R^1$ stands for hydrogen, optionally substituted alkyl, optionally substituted alkenyl, optionally substituted alkinyl, optionally substituted aralkyl, cycloalkyl or optionally substituted heteroarylalkyl, $R^2$ stands for alkyl, cycloalkyl, cycloalkylalkyl or alkenyl, $R^3$ stands for methyl and $R^4$ stands for methyl or $R^3$ and $R^4$ together stand for ethane-1,2-diyl, and their acid addition salts and metal salt complexes have now been found.

The new substituted triazolylmethylcarbinols of the formula (I) possess an asymmetrically substituted carbon atom and can therefore be obtained in the two optical isomer forms. The invention relates both to the isomer mixtures and to the individual isomers.

Furthermore, it has been found that the new substituted triazolylmethylcarbinols of the formula (I) and their acid addition salts and metal salt complexes are obtained (a) when triazolyl methyl ketones of the formula

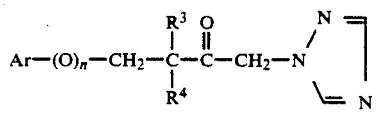

(II)

in which n, Ar, $R^3$ and $R^4$ have the abovementioned meanings, are reacted with halogen compounds of the formula $R^2 - X$ (III)

in which $R^2$ has the abovementioned meaning and

X stands for halogen, in the presence of aluminum and if appropriate with the use of ultrasound and/or in the presence of aluminum activators in the presence of a diluent, and the product is then reacted with compounds of the formula $R^1 - Y$ (IV)

in which $R^1$ has the abovementioned meaning and

Y stands for halogen, in the presence of an inert diluent, or (b) when oxiranes of the formula

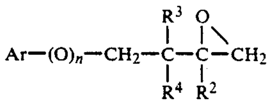

(V)

in which n, Ar, $R^2$, $R^3$ and $R^4$ have the abovementioned meanings, are reacted with 1,2,4-triazole of the formula

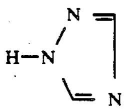

(VI)

if appropriate in the presence of an acid acceptor and if appropriate in the presence of a free-radical initiator and also if appropriate in the presence of a diluent, and if appropriate the resulting compounds of the formula

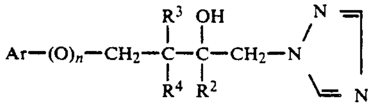

(Ia)

in which

Ar, $R^2$, $R^3$, $R^4$ and n have the abovementioned meanings, are reacted with compounds of the formula $R^5 - Y$ (IVa)

in which

Y has the abovementioned meaning and $R^5$ stands for optionally substituted alkyl, optionally substituted alkenyl, optionally substituted alkinyl, optionally substituted aralkyl, cycloalkyl or optionally substituted heteroarylalkyl, in the presence of a base and if appropriate in the presence of a diluent, and in which, if desired, an acid or a metal salt is then subjected to an addition reaction with the compounds of the formula (I).

Finally, it has been found that the new substituted triazolylmethylcarbinols of the formula (I) and also their acid addition salts and metal salt complexes are distinguished by very good fungicidal properties.

Surprisingly, the substituted triazolylmethylcarbinols of the formula (I) according to the invention and also their acid addition salts and metal salt complexes show a considerably more powerful fungicidal action than 1-(4-chlorophenyl)-4-methyl-3-(1,2,4-triazol-1-yl-methyl)pentan-3-ol, which is known and is a structurally similar active compound of the same type of action.

Formula (I) provides a general definition of the substances according to the invention. Preferred substituted triazolylmethylcarbinols of the formula (I) are those in which n stands for the numbers 0 or 1, Ar stands for phenyl or naphthyl, it being possible for each of these radicals to be monosubstituted or polysubstituted by identical or different substituents from the series comprising fluorine, chlorine, bromine, iodine, cyano, nitro, phenyl, phenoxy, benzyl, formyl, alkoximinomethyl having 1 to 4 carbon atoms in the alkoxy moiety, alkylcarbonyl having 1 to 4 carbon atoms in the alkyl moiety, alkoximinoalkyl having 1 to 4 carbon atoms in the alkoxy moiety and 2 to 4 carbon atoms in the alkyl moiety, straight-chain or branched alkyl having 1 to 4 carbon atoms, straight-chain or branched halogenoalkyl having 1 to 4 carbon atoms and 1 to 9 halogen atoms, in particular fluorine and/or chlorine atoms, straight-chain or branched alkoxy having 1 to 4 carbon atoms, straight-chain or branched halogenoalkoxy having 1 to 4 carbon atoms and 1 to 9 halogen atoms, in particular fluorine and/or chlorine atoms, straight-chain or branched alkylthio having 1 to 4 carbon atoms, straight-chain or branched halogenoalkylthio having 1 to 4 carbon atoms and 1 to 9 halogen atoms, in particular fluorine and/or chlorine atoms, straight-chain or branched alkylsulphinyl having 1 to 4 carbon atoms, straight-chain or branched halogenoalkylsulphinyl having 1 to 4 carbon atoms and 1 to 9 halogen atoms, in particular fluorine and/or chlorine atoms, straight-chain or branched alkylsulphonyl having 1 to 4 carbon atoms, and/or by straight-chain or branched halogenoalkylsulphonyl having 1 to 4 carbon atoms and 1 to 9 halogen atoms, in particular fluorine and/or chlorine atoms, $R^1$ stands for hydrogen or for straight-chain or branched alkyl having 1 to 8 carbon atoms, it being possible for each of the alkyl radicals to be monosubstituted or polysubstituted by identical or different substituents from the series comprising fluorine, chlorine, cyano, alkylcarbonyl having 1 to 4 carbon atoms in the alkyl moiety, alkoxycarbonyl having 1 to 4 carbon atoms in the alkoxy moiety and/or alkoxy having 1 to 4 carbon atoms, or $R^1$ stands for straight-chain or branched alkenyl having 2 to 4 carbon atoms, it being possible for each of the alkenyl radicals to be monosubstituted or polysubstituted by identical or different substituents from the series comprising fluorine, chlorine, cyano and/or alkoxycarbonyl having 1 to 4 carbon atoms in the alkoxy moiety, or $R^1$ stands for straight-chain or branched alkinyl having 2 to 4 carbon atoms, it being possible for each of the alkinyl radicals to be monosubstituted or polysubstituted by identical or different substituents from the series comprising fluorine, chlorine, cyano and/or alkoxycarbonyl having 1 to 4 carbon atoms in the alkoxy moiety, or $R^1$ stands for phenylalkyl which has 1 or 2 carbon atoms in the alkyl moiety and which is optionally substituted by fluorine, chlorine, cyano, nitro, methyl, ethyl, methoxy and/or trifluoromethyl, or $R^1$ stands for cycloalkyl having 3 to 8 carbon atoms, or $R^1$ stands for pyridylmethyl, pyrimidinylmethyl, furylmethyl or thienylmethyl, it being possible for each of these radicals to be monosubstituted or polysubstituted by identical or different substituents from the series comprising fluorine, chlorine, alkyl having 1 to 4 carbon atoms and/or alkoxy having 1 to 4 carbon atoms, $R^2$ stands for straight-chain or branched alkyl having 1 to 8 carbon atoms, cycloalkyl having 3 to 6 carbon atoms, cycloalkylalkyl having 3 to 6 carbon atoms in the cycloalkyl moiety and 1 or 2 carbon atoms in the alkyl moiety, or for straight-chain or branched alkenyl having 2 to 6 carbon atoms, $R^3$ stands for methyl and $R^4$ stands for methyl or $R^3$ and $R^4$ together stand for ethane-1,2-diyl.

Particularly preferred compounds of the formula (I) are those in which n stands for the numbers 0 or 1, Ar stands for phenyl or naphthyl, it being possible for each of these radicals to be monosubstituted to trisubstituted by identical or different substituents from the series comprising fluorine, chlorine, bromine, iodine, cyano, nitro, phenyl, phenoxy, benzyl, formyl, alkoximinomethyl having 1 or 2 carbon atoms in the alkoxy moiety, alkylcarbonyl having 1 or 2 carbon atoms in the alkyl moiety, alkoximinoalkyl having 1 or 2 carbon atoms in the alkoxy moiety and 2 or 3 carbon atoms in the alkyl moiety, alkyl having 1 or 2 carbon atoms, halogenoalkyl having 1 or 2 carbon atoms and 1 to 5 halogen atoms, in particular fluorine and/or chlorine atoms, alkoxy having 1 or 2 carbon atoms, halogenoalkoxy having 1 or 2 carbon atoms and 1 to 5 halogen atoms, in particular fluorine and/or chlorine atoms, alkylthio having 1 or 2 carbon atoms, halogenoalkylthio having 1 or 2 carbon atoms and 1 to 5 halogen atoms, in particular fluorine and/or chlorine atoms, alkylsulphinyl having 1 or 2 carbon atoms, halogenoalkylsulphinyl having 1 or 2 carbon atoms and 1 to 5 halogen atoms, in particular fluorine and/or chlorine atoms, alkylsulphonyl having 1 or 2 carbon atoms, and/or by halogenoalkylsulphonyl having 1 or 2 carbon atoms and 1 to 5 halogen atoms, in particular fluorine and/or chlorine atoms, $R^1$ stands for hydrogen, methyl, ethyl, propyl, isopropyl, butyl, isobutyl, sec.-butyl, pentyl, chloromethyl, fluoromethyl, methylcarbonylmethyl, methoxycarbonylmethyl, methoxymethyl, allyl, propargyl or for benzyl which is optionally monosubstituted to trisubstituted by identical or different substituents from the series comprising fluorine, chlorine, bromine, methyl, methoxy and/or trifluoromethyl, or $R^1$ stands for cyclopropyl, cyclobutyl, cyclopentyl or cyclohexyl, or $R^1$ stands for pyridylmethyl, pyrimidinylmethyl, furylmethyl or thienylmethyl, it being possible for each of these radicals to be monosubstituted or disubstituted by identical or different substituents from the series comprising fluorine, chlorine, methyl and/or methoxy, $R^2$ stands for straight-chain or branched alkyl having 1 to 6 carbon atoms, cyclopropyl, cyclopropylmethyl or alkenyl having 2 to 4 carbon atoms, $R^3$ stands for methyl and $R^4$ stands for methyl or $R^3$ and $R^4$ together stand for ethane-1,2-diyl.

A group of very particularly preferred substituted triazolylmethylcarbinols are the compounds of the formula (I) in which n stands for the number 0, Ar stands for phenyl which is optionally substituted in the 4-position by fluorine, chlorine, bromine, methyl, trifluoromethyl, methoxy, difluoromethoxy or trifluoromethoxy, or for phenyl which is optionally substituted in the 4-position and also additionally substituted by identical or different substituents from the series comprising fluorine, chlorine, bromine, methyl, trifluoromethyl, methoxy, difluoromethoxy or trifluoromethoxy in the 2- or 3-position, $R^1$ stands for hydrogen, methyl, ethyl, propyl, isopropyl, butyl, isobutyl, sec.-butyl, pentyl, cyclopropyl or allyl, $R^2$ stands for alkyl having 1 to 6 carbon atoms, cyclopropyl or allyl, $R^3$ stands for methyl and $R^4$ stands for methyl.

Another group of very particularly preferred substances according to the invention are the compounds of the formula (I) in which n stands for the number 1, Ar stands for phenyl which is optionally substituted in the 4-position by fluorine, chlorine, bromine, methyl, trifluoromethyl, methoxy, difluoromethoxy or trifluoromethoxy, or for phenyl which is optionally substituted in the 4-position and also additionally substituted by identical or different substituents from the series comprising fluorine, chlorine, bromine, methyl, trifluoromethyl, methoxy, difluoromethoxy or trifluoromethoxy in the 2- or 3-position, $R^1$ stands for hydrogen, methyl, ethyl, propyl, isopropyl, butyl, isobutyl, sec.-butyl, pentyl, cyclopropyl or allyl, $R^2$ stands for alkyl having 1 to 6 carbon atoms, cyclopropyl or allyl, $R^3$ stands for methyl and $R^4$ stands for methyl.

A further group of very particularly preferred substances according to the invention are the compounds of the formula (I) in which n stands for the number 0, Ar stands for phenyl which is optionally substituted in the 4-position by fluorine, chlorine, bromine, methyl, trifluoromethyl, methoxy, difluoromethoxy or trifluoromethoxy, or for phenyl which is optionally substituted in the 4-position and also additionally substituted by identical or different substituents from the series comprising fluorine, chlorine, bromine, methyl, trifluoromethyl, methoxy, difluoromethoxy or trifluoromethoxy in the 2- or 3-position, $R^1$ stands for hydrogen, methyl, ethyl, propyl, isopropyl, butyl, isobutyl, sec.-butyl, pentyl, cyclopropyl or allyl, $R^2$ stands for alkyl having 1 to 6 carbon atoms, cyclopropyl or allyl and $R^3$ and $R^4$ together stand for ethane-1,2-diyl.

Finally, an additional group of very particularly preferred substances according to the invention are the compounds of the formula (I) in which n stands for the number 1, Ar stands for phenyl which is optionally substituted in the 4-position by fluorine, chlorine, bromine, methyl, trifluoromethyl, methoxy, difluoromethoxy or trifluoromethoxy, or for phenyl which is optionally substituted in the 4-position and also additionally substituted by identical or different substituents from the series comprising fluorine, chlorine, bromine, methyl, trifluoromethyl, methoxy, difluoromethoxy or trifluoromethoxy in the 2- or 3-position, $R^1$ stands for hydrogen, methyl, ethyl, propyl, isopropyl, butyl, isobutyl, sec.-butyl, pentyl, cyclopropyl or allyl, $R^2$ stands for alkyl having 1 to 6 carbon atoms, cyclopropyl or allyl and $R^3$ and $R^4$ together stand for ethane-1,2-diyl.

Other preferred compounds according to the invention are addition products of acids and those compounds of the formula (I) in which n, Ar, $R^1$, $R^2$, $R^3$ and R4 have those meanings which have already been preferably mentioned in connection with the description of the substances according to the invention for these substituents and the index n.

The acids which can be subjected to the addition reaction preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid.

Other preferred compounds according to the invention are addition products of salts of metals of main groups II to IV and subgroups I and II and also IV to VIII of the Periodic Table of the Elements and those compounds of the formula (I) in which n, Ar, $R^1$, $R^2$, $R^3$ and R4 have the meanings which have already been preferably mentioned in connection with the description of the substances according to the invention for these substituents and the index n.

In this context, salts of copper, zinc, manganese, magnesium, tin, iron and of nickel are particularly preferred. Suitable anions of these salts are those which are derived from those acids which lead to physiologically acceptable addition products. Particularly preferred acids of this type in this connection are the hydrohalic acids, such as, for example, hydrochloric acid and hydrobromic acid, furthermore phosphoric acid, nitric acid and sulphuric acid.

Examples of the compounds of the formula (I) according to the invention are listed in Table 1 below (cf. also the Preparation Examples).

TABLE 1

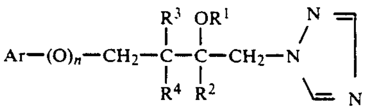

(I)

| Ar | n | $R^1$ | $R^2$ | $R^3$ | $R^4$ |
|---|---|---|---|---|---|
| 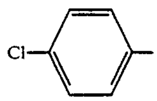 | 0 | H | $-CH_3$ | $CH_3$ | $CH_3$ |

TABLE 1-continued
| | | | | | |
|---|---|---|---|---|---|
| 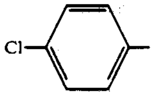 | 0 | H | $-C_2H_5$ | $CH_3$ | $CH_3$ |
| 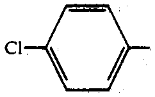 | 0 | H | $-C_3H_7$-n | $CH_3$ | $CH_3$ |
| 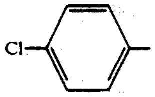 | 0 | H | $-CH(CH_3)_2$ | $CH_3$ | $CH_3$ |
| 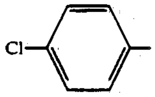 | 0 | H | 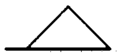 | $CH_3$ | $CH_3$ |
| 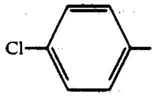 | 0 | H | $-CH_2CH{=}CH_2$ | $CH_3$ | $CH_3$ |
| 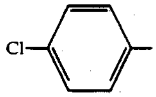 | 0 | H | $-(CH_2)_3-CH_3$ | $CH_3$ | $CH_3$ |
| 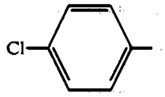 | 0 | H | $-CH_2CH(CH_3)_2$ | $CH_3$ | $CH_3$ |
| 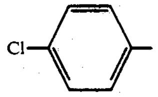 | 0 | H | $-(CH_2)_4-CH_3$ | $CH_3$ | $CH_3$ |
| 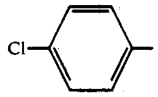 | 0 | H | $-(CH_2)_5-CH_3$ | $CH_3$ | $CH_3$ |
| 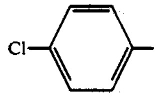 | 1 | H | $-CH_3$ | $CH_3$ | $CH_3$ |
| 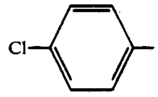 | 1 | H | $-C_2H_5$ | $CH_3$ | $CH_3$ |
| 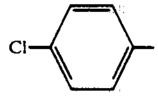 | 1 | H | $-C_3H_7$-n | $CH_3$ | $CH_3$ |
| 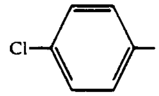 | 1 | H | $-CH(CH_3)_2$ | $CH_3$ | $CH_3$ |

TABLE 1-continued
| | | | | | |
|---|---|---|---|---|---|
| 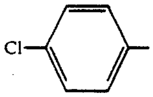 | 1 | H | 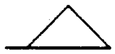 | $CH_3$ | $CH_3$ |
| 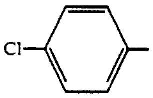 | 1 | H | $-CH_2CH{=}CH_2$ | $CH_3$ | $CH_3$ |
| 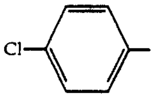 | 1 | H | $-(CH_2)_3-CH_3$ | $CH_3$ | $CH_3$ |
| 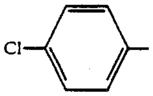 | 1 | H | $-CH_2CH(CH_3)_2$ | $CH_3$ | $CH_3$ |
| 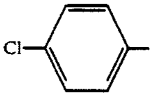 | 1 | H | $-(CH_2)_4-CH_3$ | $CH_3$ | $CH_3$ |
| 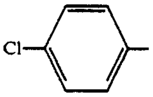 | 1 | H | $-(CH_2)_5-CH_3$ | $CH_3$ | $CH_3$ |
| 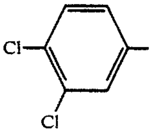 | 0 | H | $-CH_3$ | $CH_3$ | $CH_3$ |
| 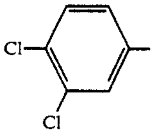 | 1 | H | $-CH_3$ | $CH_3$ | $CH_3$ |
| 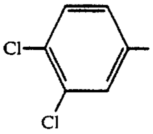 | 0 | H | $-C_2H_5$ | $CH_3$ | $CH_3$ |
| 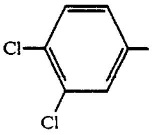 | 1 | H | $-C_2H_5$ | $CH_3$ | $CH_3$ |
| 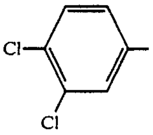 | 0 | H | $-CH_2CH_2CH_3$ | $CH_3$ | $CH_3$ |
| 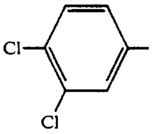 | 1 | H | $-CH_2CH_2CH_3$ | $CH_3$ | $CH_3$ |

TABLE 1-continued
| | | | | | |
|---|---|---|---|---|---|
| 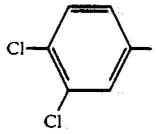 | 0 | H | $-CH(CH_3)_2$ | $CH_3$ | $CH_3$ |
| 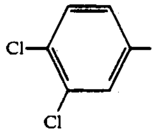 | 1 | H | $-CH(CH_3)_2$ | $CH_3$ | $CH_3$ |
| 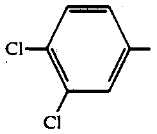 | 0 | H | 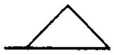 | $CH_3$ | $CH_3$ |
| 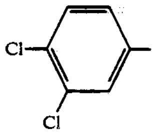 | 1 | H | 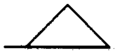 | $CH_3$ | $CH_3$ |
| 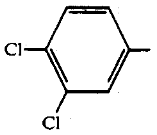 | 0 | H | $-CH_2CH{=}CH_2$ | $CH_3$ | $CH_3$ |
| 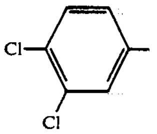 | 1 | H | $-CH_2CH{=}CH_2$ | $CH_3$ | $CH_3$ |
| 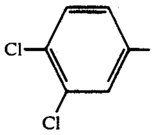 | 0 | H | $-(CH_2)_3-CH_3$ | $CH_3$ | $CH_3$ |
| 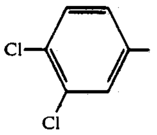 | 1 | H | $-(CH_2)_3-CH_3$ | $CH_3$ | $CH_3$ |
| 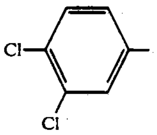 | 0 | H | $-CH_2CH(CH_3)_2$ | $CH_3$ | $CH_3$ |
| 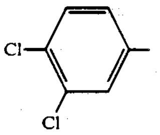 | 1 | H | $-CH_2CH(CH_3)_2$ | $CH_3$ | $CH_3$ |

TABLE 1-continued
| | | | | | |
|---|---|---|---|---|---|
| 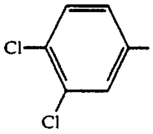 | 0 | H | $-(CH_2)_4-CH_3$ | $CH_3$ | $CH_3$ |
| 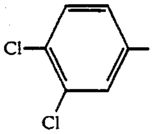 | 1 | H | $-(CH_2)_4-CH_3$ | $CH_3$ | $CH_3$ |
| 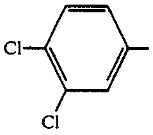 | 0 | H | $-(CH_2)_5-CH_3$ | $CH_3$ | $CH_3$ |
| 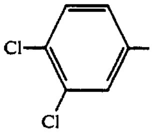 | 1 | H | $-(CH_2)_5-CH_3$ | $CH_3$ | $CH_3$ |
| 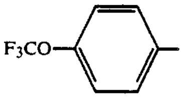 | 0 | H | $-CH_3$ | $CH_3$ | $CH_3$ |
| 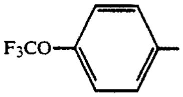 | 1 | H | $-CH_3$ | $CH_3$ | $CH_3$ |
| 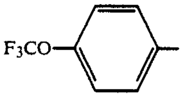 | 0 | H | $-C_2H_5$ | $CH_3$ | $CH_3$ |
| 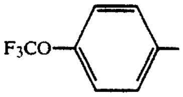 | 1 | H | $-C_2H_5$ | $CH_3$ | $CH_3$ |
| 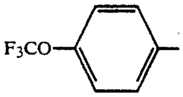 | 0 | H | $-CH_2CH_2CH_3$ | $CH_3$ | $CH_3$ |
| 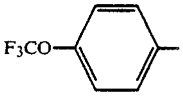 | 1 | H | $-CH_2CH_2CH_3$ | $CH_3$ | $CH_3$ |
| 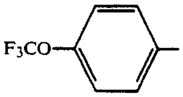 | 0 | H | $-CH(CH_3)_2$ | $CH_3$ | $CH_3$ |
| 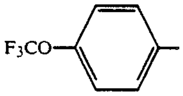 | 1 | H | $-CH(CH_3)_2$ | $CH_3$ | $CH_3$ |

TABLE 1-continued
| | | | | | |
|---|---|---|---|---|---|
| 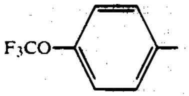 | 0 | H | 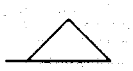 | $CH_3$ | $CH_3$ |
| 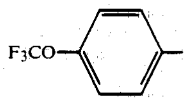 | 1 | H | 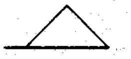 | $CH_3$ | $CH_3$ |
| 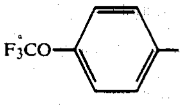 | 0 | H | $-CH_2CH{=}CH_2$ | $CH_3$ | $CH_3$ |
| 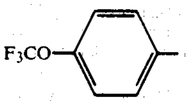 | 1 | H | $-CH_2CH{=}CH_2$ | $CH_3$ | $CH_3$ |
| 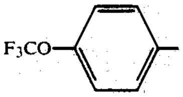 | 0 | H | $-(CH_2)_3-CH_3$ | $CH_3$ | $CH_3$ |
| 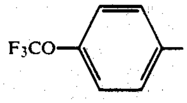 | 1 | H | $-(CH_2)_3-CH_3$ | $CH_3$ | $CH_3$ |
| 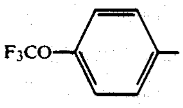 | 0 | H | $-CH_2CH(CH_3)_2$ | $CH_3$ | $CH_3$ |
| 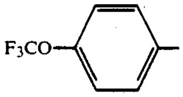 | 1 | H | $-CH_2CH(CH_3)_2$ | $CH_3$ | $CH_3$ |
| 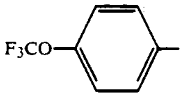 | 0 | H | $-(CH_2)_4-CH_3$ | $CH_3$ | $CH_3$ |
| 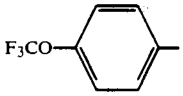 | 1 | H | $-(CH_2)_4-CH_3$ | $CH_3$ | $CH_3$ |
| 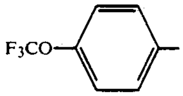 | 0 | H | $-(CH_2)_5-CH_3$ | $CH_3$ | $CH_3$ |
| 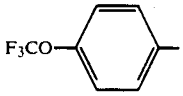 | 1 | H | $-(CH_2)_5-CH_3$ | $CH_3$ | $CH_3$ |
| 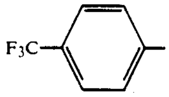 | 0 | H | $-CH_3$ | $CH_3$ | $CH_3$ |

TABLE 1-continued
| | | | | | |
|---|---|---|---|---|---|
| 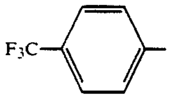 | 1 | H | $-CH_3$ | $CH_3$ | $CH_3$ |
| 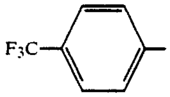 | 0 | H | $-C_2H_5$ | $CH_3$ | $CH_3$ |
| 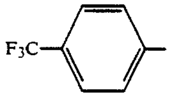 | 1 | H | $-C_2H_5$ | $CH_3$ | $CH_3$ |
| 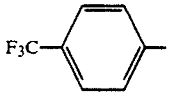 | 0 | H | $-CH_2CH_2CH_3$ | $CH_3$ | $CH_3$ |
| 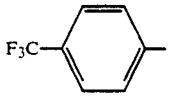 | 1 | H | $-CH_2CH_2CH_3$ | $CH_3$ | $CH_3$ |
| 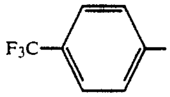 | 0 | H | $-CH(CH_3)_2$ | $CH_3$ | $CH_3$ |
| 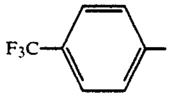 | 1 | H | $-CH(CH_3)_2$ | $CH_3$ | $CH_3$ |
| 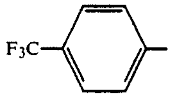 | 0 | H | 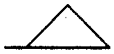 | $CH_3$ | $CH_3$ |
| 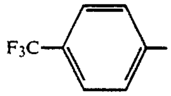 | 1 | H | 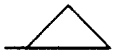 | $CH_3$ | $CH_3$ |
| 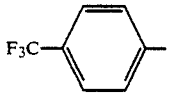 | 0 | H | $-CH_2CH{=}CH_2$ | $CH_3$ | $CH_3$ |
| 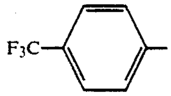 | 1 | H | $-CH_2CH{=}CH_2$ | $CH_3$ | $CH_3$ |
| 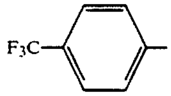 | 0 | H | $-(CH_2)_3-CH_3$ | $CH_3$ | $CH_3$ |
| 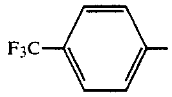 | 1 | H | $-(CH_2)_3-CH_3$ | $CH_3$ | $CH_3$ |

TABLE 1-continued
| | | | | | |
|---|---|---|---|---|---|
| 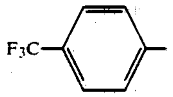 | 0 | H | $-CH_2CH(CH_3)_2$ | $CH_3$ | $CH_3$ |
| 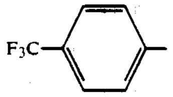 | 1 | H | $-CH_2CH(CH_3)_2$ | $CH_3$ | $CH_3$ |
| 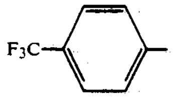 | 0 | H | $-(CH_2)_4-CH_3$ | $CH_3$ | $CH_3$ |
| 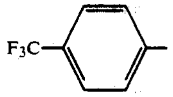 | 1 | H | $-(CH_2)_4-CH_3$ | $CH_3$ | $CH_3$ |
| 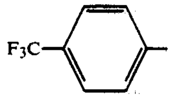 | 0 | H | $-(CH_2)_5-CH_3$ | $CH_3$ | $CH_3$ |
| 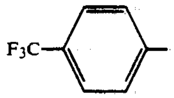 | 1 | H | $-(CH_2)_5-CH_3$ | $CH_3$ | $CH_3$ |
| 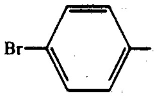 | 0 | H | $-CH_3$ | $CH_3$ | $CH_3$ |
| 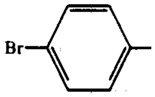 | 1 | H | $-CH_3$ | $CH_3$ | $CH_3$ |
| 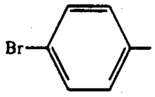 | 0 | H | $-C_2H_5$ | $CH_3$ | $CH_3$ |
| 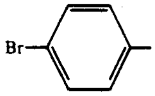 | 1 | H | $-C_2H_5$ | $CH_3$ | $CH_3$ |
| 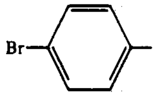 | 0 | H | $-CH_2CH_2CH_3$ | $CH_3$ | $CH_3$ |
| 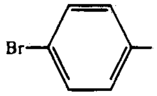 | 1 | H | $-CH_2CH_2CH_3$ | $CH_3$ | $CH_3$ |
| 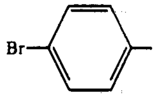 | 0 | H | $-CH(CH_3)_2$ | $CH_3$ | $CH_3$ |

TABLE 1-continued
| | | | | | |
|---|---|---|---|---|---|
| 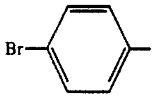 | 1 | H | $-CH(CH_3)_2$ | $CH_3$ | $CH_3$ |
| 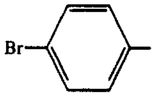 | 0 | H | 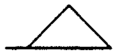 | $CH_3$ | $CH_3$ |
| 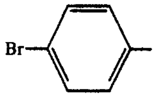 | 1 | H | 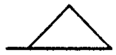 | $CH_3$ | $CH_3$ |
| 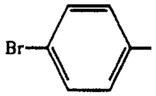 | 0 | H | $-CH_2CH{=}CH_2$ | $CH_3$ | $CH_3$ |
| 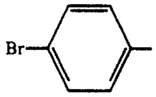 | 1 | H | $-CH_2CH{=}CH_2$ | $CH_3$ | $CH_3$ |
| 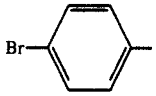 | 0 | H | $-(CH_2)_3-CH_3$ | $CH_3$ | $CH_3$ |
| 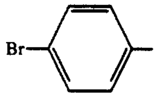 | 1 | H | $-(CH_2)_3-CH_3$ | $CH_3$ | $CH_3$ |
| 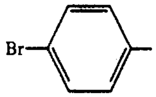 | 0 | H | $-CH_2CH(CH_3)_2$ | $CH_3$ | $CH_3$ |
| 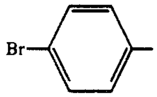 | 1 | H | $-CH_2CH(CH_3)_2$ | $CH_3$ | $CH_3$ |
| 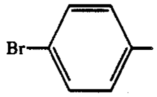 | 0 | H | $-(CH_2)_4-CH_3$ | $CH_3$ | $CH_3$ |
| 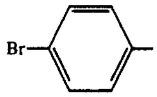 | 1 | H | $-(CH_2)_4-CH_3$ | $CH_3$ | $CH_3$ |
| 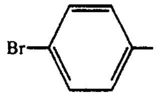 | 0 | H | $-(CH_2)_5-CH_3$ | $CH_3$ | $CH_3$ |
| 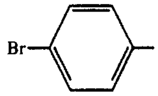 | 1 | H | $-(CH_2)_5-CH_3$ | $CH_3$ | $CH_3$ |

TABLE 1-continued
| | | | | | |
|---|---|---|---|---|---|
| 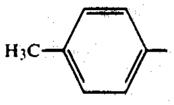 | 0 | H | $-CH_3$ | $CH_3$ | $CH_3$ |
| 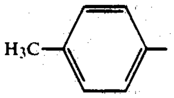 | 1 | H | $-CH_3$ | $CH_3$ | $CH_3$ |
| 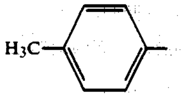 | 0 | H | $-C_2H_5$ | $CH_3$ | $CH_3$ |
| 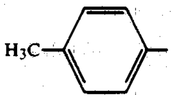 | 1 | H | $-C_2H_5$ | $CH_3$ | $CH_3$ |
| 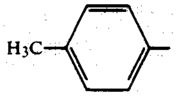 | 0 | H | $-CH_2CH_2CH_3$ | $CH_3$ | $CH_3$ |
| 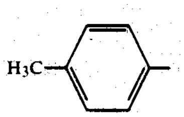 | 1 | H | $-CH_2CH_2CH_3$ | $CH_3$ | $CH_3$ |
| 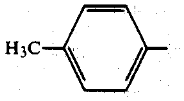 | 0 | H | $-CH(CH_3)_2$ | $CH_3$ | $CH_3$ |
| 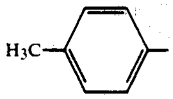 | 1 | H | $-CH(CH_3)_2$ | $CH_3$ | $CH_3$ |
| 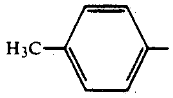 | 0 | H | 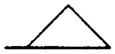 | $CH_3$ | $CH_3$ |
| 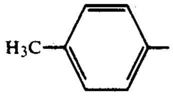 | 1 | H | 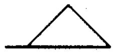 | $CH_3$ | $CH_3$ |
| 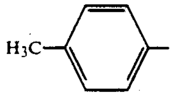 | 0 | H | $-CH_2CH{=}CH_2$ | $CH_3$ | $CH_3$ |
| 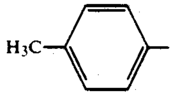 | 1 | H | $-CH_2CH{=}CH_2$ | $CH_3$ | $CH_3$ |
| 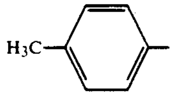 | 0 | H | $-(CH_2)_3-CH_3$ | $CH_3$ | $CH_3$ |

TABLE 1-continued
| | | | | | |
|---|---|---|---|---|---|
| 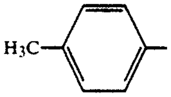 | 1 | H | $-(CH_2)_3-CH_3$ | $CH_3$ | $CH_3$ |
| 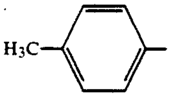 | 0 | H | $-CH_2CH(CH_3)_2$ | $CH_3$ | $CH_3$ |
| 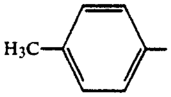 | 1 | H | $-CH_2CH(CH_3)_2$ | $CH_3$ | $CH_3$ |
| 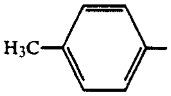 | 0 | H | $-(CH_2)_4-CH_3$ | $CH_3$ | $CH_3$ |
| 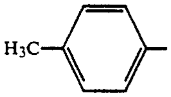 | 1 | H | $-(CH_2)_4-CH_3$ | $CH_3$ | $CH_3$ |
| 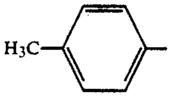 | 0 | H | $-(CH_2)_5-CH_3$ | $CH_3$ | $CH_3$ |
| 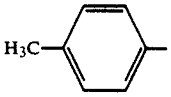 | 1 | H | $-(CH_2)_5-CH_3$ | $CH_3$ | $CH_3$ |
| 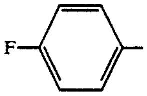 | 0 | H | $-CH_3$ | $CH_3$ | $CH_3$ |
| 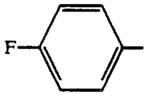 | 1 | H | $-CH_3$ | $CH_3$ | $CH_3$ |
| 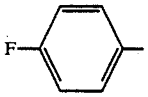 | 0 | H | $-C_2H_5$ | $CH_3$ | $CH_3$ |
| 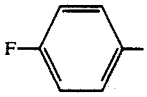 | 1 | H | $-C_2H_5$ | $CH_3$ | $CH_3$ |
| 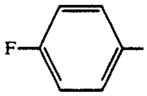 | 0 | H | $-CH_2CH_2CH_3$ | $CH_3$ | $CH_3$ |
| 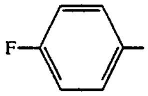 | 1 | H | $-CH_2CH_2CH_3$ | $CH_3$ | $CH_3$ |

TABLE 1-continued
| | | | | | |
|---|---|---|---|---|---|
| 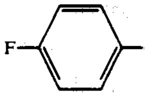 | 0 | H | $-CH(CH_3)_2$ | $CH_3$ | $CH_3$ |
| 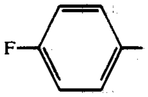 | 1 | H | $-CH(CH_3)_2$ | $CH_3$ | $CH_3$ |
| 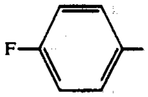 | 0 | H | 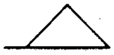 | $CH_3$ | $CH_3$ |
| 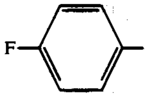 | 1 | H | 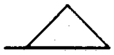 | $CH_3$ | $CH_3$ |
| 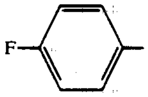 | 0 | H | $-CH_2CH{=}CH_2$ | $CH_3$ | $CH_3$ |
| 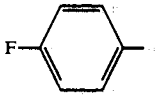 | 1 | H | $-CH_2CH{=}CH_2$ | $CH_3$ | $CH_3$ |
| 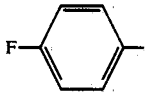 | 0 | H | $-(CH_2)_3-CH_3$ | $CH_3$ | $CH_3$ |
| 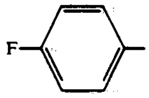 | 1 | H | $-(CH_2)_3-CH_3$ | $CH_3$ | $CH_3$ |
| 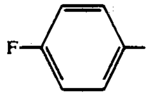 | 0 | H | $-CH_2CH(CH_3)_2$ | $CH_3$ | $CH_3$ |
| 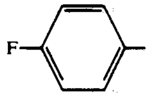 | 1 | H | $-CH_2CH(CH_3)_2$ | $CH_3$ | $CH_3$ |
| 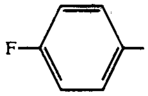 | 0 | H | $-(CH_2)_4-CH_3$ | $CH_3$ | $CH_3$ |
| 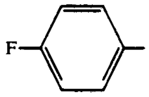 | 1 | H | $-(CH_2)_4-CH_3$ | $CH_3$ | $CH_3$ |
| 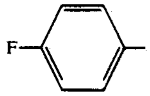 | 0 | H | $-(CH_2)_5-CH_3$ | $CH_3$ | $CH_3$ |

TABLE 1-continued
| | | | | | |
|---|---|---|---|---|---|
| 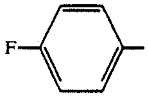 | 1 | H | $-(CH_2)_5-CH_3$ | $CH_3$ | $CH_3$ |
| 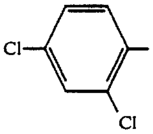 | 0 | H | $-CH_3$ | $CH_3$ | $CH_3$ |
| 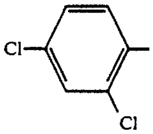 | 1 | H | $-CH_3$ | $CH_3$ | $CH_3$ |
| 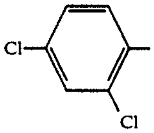 | 0 | H | $-C_2H_5$ | $CH_3$ | $CH_3$ |
| 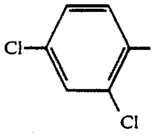 | 1 | H | $-C_2H_5$ | $CH_3$ | $CH_3$ |
| 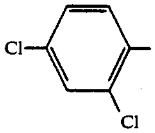 | 0 | H | $-CH_2CH_2CH_3$ | $CH_3$ | $CH_3$ |
| 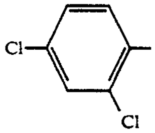 | 1 | H | $-CH_2CH_2CH_3$ | $CH_3$ | $CH_3$ |
| 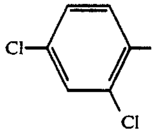 | 0 | H | $-CH(CH_3)_2$ | $CH_3$ | $CH_3$ |
| 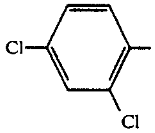 | 1 | H | $-CH(CH_3)_2$ | $CH_3$ | $CH_3$ |
| 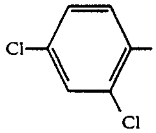 | 0 | H | 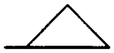 | $CH_3$ | $CH_3$ |
| 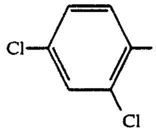 | 1 | H | 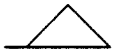 | $CH_3$ | $CH_3$ |

TABLE 1-continued
| | | | | | |
|---|---|---|---|---|---|
| 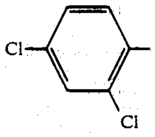 | 0 | H | $-CH_2CH{=}CH_2$ | $CH_3$ | $CH_3$ |
| 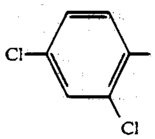 | 1 | H | $-CH_2CH{=}CH_2$ | $CH_3$ | $CH_3$ |
| 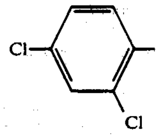 | 0 | H | $-(CH_2)_3-CH_3$ | $CH_3$ | $CH_3$ |
| 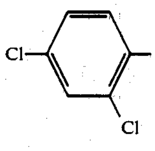 | 1 | H | $-(CH_2)_3-CH_3$ | $CH_3$ | $CH_3$ |
| 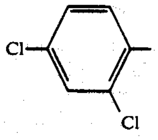 | 0 | H | $-CH_2CH(CH_3)_2$ | $CH_3$ | $CH_3$ |
| 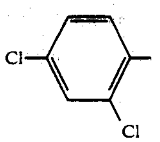 | 1 | H | $-CH_2CH(CH_3)_2$ | $CH_3$ | $CH_3$ |
| 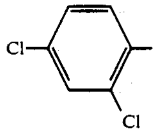 | 0 | H | $-(CH_2)_4-CH_3$ | $CH_3$ | $CH_3$ |
| 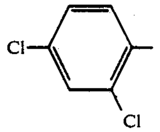 | 1 | H | $-(CH_2)_4-CH_3$ | $CH_3$ | $CH_3$ |
| 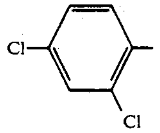 | 0 | H | $-(CH_2)_5-CH_3$ | $CH_3$ | $CH_3$ |
| 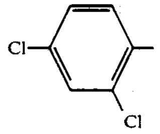 | 1 | H | $-(CH_2)_5-CH_3$ | $CH_3$ | $CH_3$ |

TABLE 1-continued
| | | | | | |
|---|---|---|---|---|---|
| 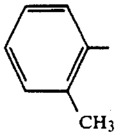 | 0 | H | $-CH_3$ | $CH_3$ | $CH_3$ |
| 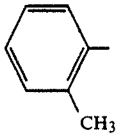 | 1 | H | $-CH_3$ | $CH_3$ | $CH_3$ |
| 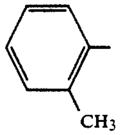 | 0 | H | $-C_2H_5$ | $CH_3$ | $CH_3$ |
| 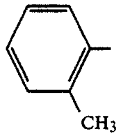 | 1 | H | $-C_2H_5$ | $CH_3$ | $CH_3$ |
| 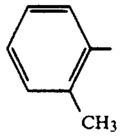 | 0 | H | $-CH_2CH_2CH_3$ | $CH_3$ | $CH_3$ |
| 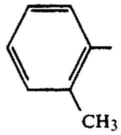 | 1 | H | $-CH_2CH_2CH_3$ | $CH_3$ | $CH_3$ |
| 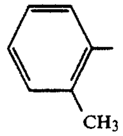 | 0 | H | $-CH(CH_3)_2$ | $CH_3$ | $CH_3$ |
| 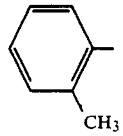 | 1 | H | $-CH(CH_3)_2$ | $CH_3$ | $CH_3$ |
| 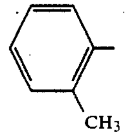 | 0 | H | 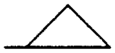 | $CH_3$ | $CH_3$ |
| 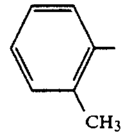 | 1 | H | 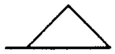 | $CH_3$ | $CH_3$ |

TABLE 1-continued
| | | | | | |
|---|---|---|---|---|---|
| 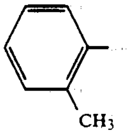 | 0 | H | $-CH_2CH{=}CH_2$ | $CH_3$ | $CH_3$ |
| 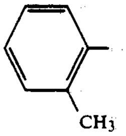 | 1 | H | $-CH_2CH{=}CH_2$ | $CH_3$ | $CH_3$ |
| 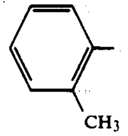 | 0 | H | $-(CH_2)_3-CH_3$ | $CH_3$ | $CH_3$ |
| 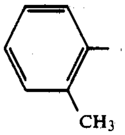 | 1 | H | $-(CH_2)_3-CH_3$ | $CH_3$ | $CH_3$ |
| 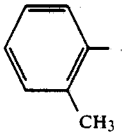 | 0 | H | $-CH_2CH(CH_3)_2$ | $CH_3$ | $CH_3$ |
| 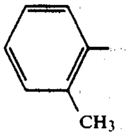 | 1 | H | $-CH_2CH(CH_3)_2$ | $CH_3$ | $CH_3$ |
| 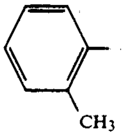 | 0 | H | $-(CH_2)_4-CH_3$ | $CH_3$ | $CH_3$ |
| 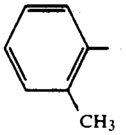 | 1 | H | $-(CH_2)_4-CH_3$ | $CH_3$ | $CH_3$ |
| 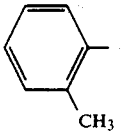 | 0 | H | $-(CH_2)_5-CH_3$ | $CH_3$ | $CH_3$ |
| 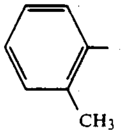 | 1 | H | $-(CH_2)_5-CH_3$ | $CH_3$ | $CH_3$ |

TABLE 1-continued
| | | | | | |
|---|---|---|---|---|---|
| 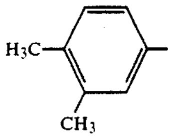 | 0 | H | $-CH_3$ | $CH_3$ | $CH_3$ |
| 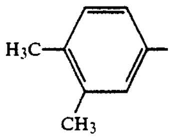 | 1 | H | $-CH_3$ | $CH_3$ | $CH_3$ |
| 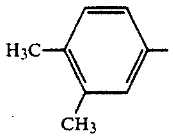 | 0 | H | $-C_2H_5$ | $CH_3$ | $CH_3$ |
| 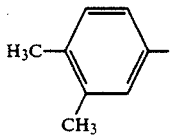 | 1 | H | $-C_2H_5$ | $CH_3$ | $CH_3$ |
| 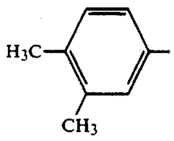 | 0 | H | $-CH_2CH_2CH_3$ | $CH_3$ | $CH_3$ |
| 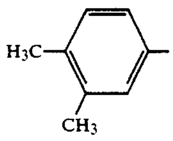 | 1 | H | $-CH_2CH_2CH_3$ | $CH_3$ | $CH_3$ |
| 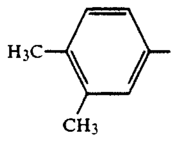 | 0 | H | $-CH(CH_3)_2$ | $CH_3$ | $CH_3$ |
| 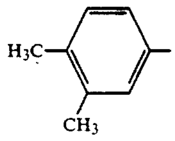 | 1 | H | $-CH(CH_3)_2$ | $CH_3$ | $CH_3$ |
| 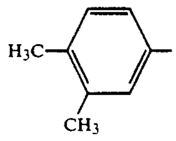 | 0 | H | 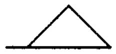 | $CH_3$ | $CH_3$ |
| 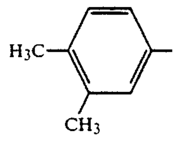 | 1 | H | 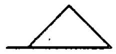 | $CH_3$ | $CH_3$ |

TABLE 1-continued
| | | | | | |
|---|---|---|---|---|---|
| 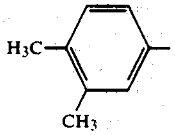 | 0 | H | $-CH_2CH{=}CH_2$ | $CH_3$ | $CH_3$ |
| 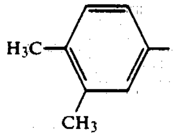 | 1 | H | $-CH_2CH{=}CH_2$ | $CH_3$ | $CH_3$ |
| 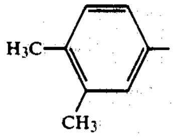 | 0 | H | $-(CH_2)_3-CH_3$ | $CH_3$ | $CH_3$ |
| 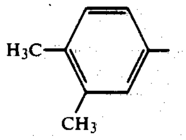 | 1 | H | $-(CH_2)_3-CH_3$ | $CH_3$ | $CH_3$ |
| 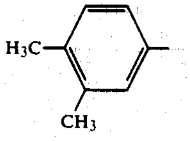 | 0 | H | $-CH_2CH(CH_3)_2$ | $CH_3$ | $CH_3$ |
| 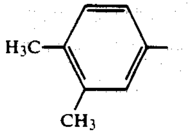 | 1 | H | $-CH_2CH(CH_3)_2$ | $CH_3$ | $CH_3$ |
| 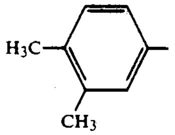 | 0 | H | $-(CH_2)_4-CH_3$ | $CH_3$ | $CH_3$ |
| 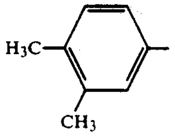 | 1 | H | $-(CH_2)_4-CH_3$ | $CH_3$ | $CH_3$ |
| 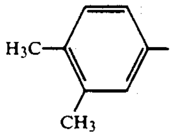 | 0 | H | $-(CH_2)_5-CH_3$ | $CH_3$ | $CH_3$ |
| 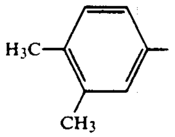 | 1 | H | $-(CH_2)_5-CH_3$ | $CH_3$ | $CH_3$ |

TABLE 1-continued
| | | | | | |
|---|---|---|---|---|---|
| 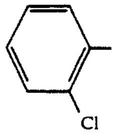 | 0 | H | $-CH_3$ | $CH_3$ | $CH_3$ |
| 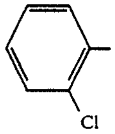 | 1 | H | $-CH_3$ | $CH_3$ | $CH_3$ |
| 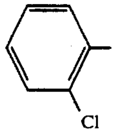 | 0 | H | $-C_2H_5$ | $CH_3$ | $CH_3$ |
| 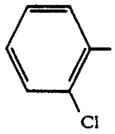 | 1 | H | $-C_2H_5$ | $CH_3$ | $CH_3$ |
| 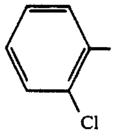 | 0 | H | $-CH_2CH_2CH_3$ | $CH_3$ | $CH_3$ |
| 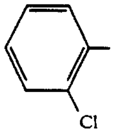 | 1 | H | $-CH_2CH_2CH_3$ | $CH_3$ | $CH_3$ |
| 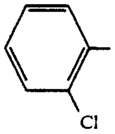 | 0 | H | $-CH(CH_3)_2$ | $CH_3$ | $CH_3$ |
| 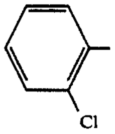 | 1 | H | $-CH(CH_3)_2$ | $CH_3$ | $CH_3$ |
| 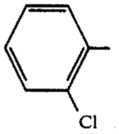 | 0 | H | 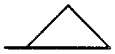 | $CH_3$ | $CH_3$ |
| 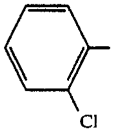 | 1 | H | 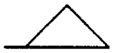 | $CH_3$ | $CH_3$ |

-continued
| | | | | | |
|---|---|---|---|---|---|
| 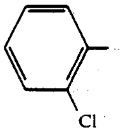 | 0 | H | $-CH_2CH{=}CH_2$ | $CH_3$ | $CH_3$ |
| 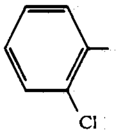 | 1 | H | $-CH_2CH{=}CH_2$ | $CH_3$ | $CH_3$ |
| 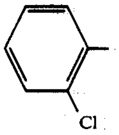 | 0 | H | $-(CH_2)_3-CH_3$ | $CH_3$ | $CH_3$ |
| 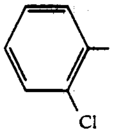 | 1 | H | $-(CH_2)_3-CH_3$ | $CH_3$ | $CH_3$ |
| 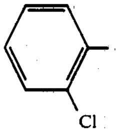 | 0 | H | $-CH_2CH(CH_3)_2$ | $CH_3$ | $CH_3$ |
| 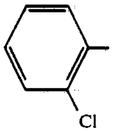 | 1 | H | $-CH_2CH(CH_3)_2$ | $CH_3$ | $CH_3$ |
| 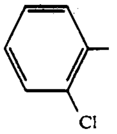 | 0 | H | $-(CH_2)_4-CH_3$ | $CH_3$ | $CH_3$ |
| 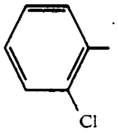 | 1 | H | $-(CH_2)_4-CH_3$ | $CH_3$ | $CH_3$ |
| 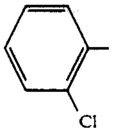 | 0 | H | $-(CH_2)_5-CH_3$ | $CH_3$ | $CH_3$ |
| 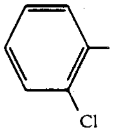 | 1 | H | $-(CH_2)_5-CH_3$ | $CH_3$ | $CH_3$ |

-continued
| | | | | | |
|---|---|---|---|---|---|
| 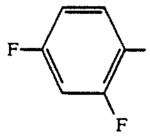 | 0 | H | $-CH_3$ | $CH_3$ | $CH_3$ |
| 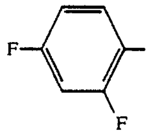 | 1 | H | $-CH_3$ | $CH_3$ | $CH_3$ |
| 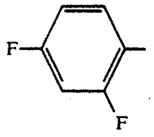 | 0 | H | $-C_2H_5$ | $CH_3$ | $CH_3$ |
| 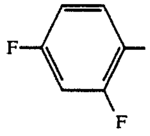 | 1 | H | $-C_2H_5$ | $CH_3$ | $CH_3$ |
| 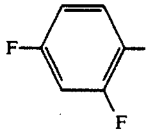 | 0 | H | $-CH_2CH_2CH_3$ | $CH_3$ | $CH_3$ |
| 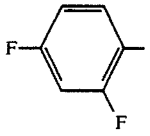 | 1 | H | $-CH_2CH_2CH_3$ | $CH_3$ | $CH_3$ |
| 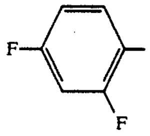 | 0 | H | $-CH(CH_3)_2$ | $CH_3$ | $CH_3$ |
| 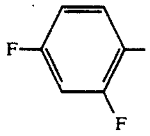 | 1 | H | $-CH(CH_3)_2$ | $CH_3$ | $CH_3$ |
| 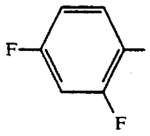 | 0 | H | 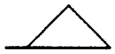 | $CH_3$ | $CH_3$ |
| 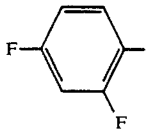 | 1 | H | 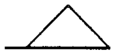 | $CH_3$ | $CH_3$ |

-continued
| | | | | | |
|---|---|---|---|---|---|
| 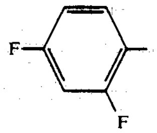 | 0 | H | $-CH_2CH=CH_2$ | $CH_3$ | $CH_3$ |
| 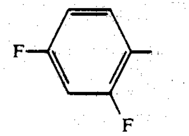 | 1 | H | $-CH_2CH=CH_2$ | $CH_3$ | $CH_3$ |
| 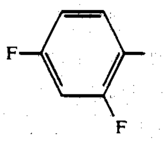 | 0 | H | $-(CH_2)_3-CH_3$ | $CH_3$ | $CH_3$ |
| 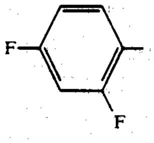 | 1 | H | $-(CH_2)_3-CH_3$ | $CH_3$ | $CH_3$ |
| 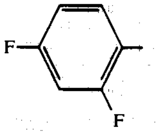 | 0 | H | $-CH_2CH(CH_3)_2$ | $CH_3$ | $CH_3$ |
| 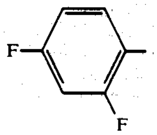 | 1 | H | $-CH_2CH(CH_3)_2$ | $CH_3$ | $CH_3$ |
| 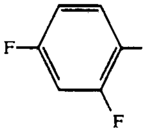 | 0 | H | $-(CH_2)_4-CH_3$ | $CH_3$ | $CH_3$ |
| 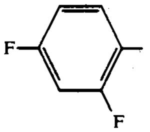 | 1 | H | $-(CH_2)_4-CH_3$ | $CH_3$ | $CH_3$ |
| 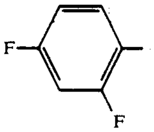 | 0 | H | $-(CH_2)_5-CH_3$ | $CH_3$ | $CH_3$ |
| 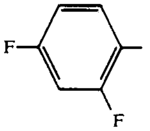 | 1 | H | $-(CH_2)_5-CH_3$ | $CH_3$ | $CH_3$ |
| 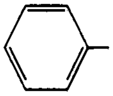 | 0 | H | $-CH_3$ | $CH_3$ | $CH_3$ |

-continued
| | | | | | |
|---|---|---|---|---|---|
| 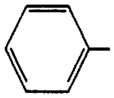 | 1 | H | $-CH_3$ | $CH_3$ | $CH_3$ |
| 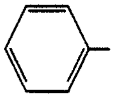 | 0 | H | $-C_2H_5$ | $CH_3$ | $CH_3$ |
| 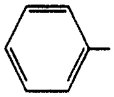 | 1 | H | $-C_2H_5$ | $CH_3$ | $CH_3$ |
| 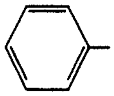 | 0 | H | $-CH_2CH_2CH_3$ | $CH_3$ | $CH_3$ |
| 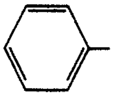 | 1 | H | $-CH_2CH_2CH_3$ | $CH_3$ | $CH_3$ |
| 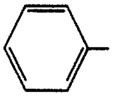 | 0 | H | $-CH(CH_3)_2$ | $CH_3$ | $CH_3$ |
| 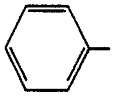 | 1 | H | $-CH(CH_3)_2$ | $CH_3$ | $CH_3$ |
| 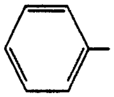 | 0 | H | 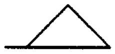 | $CH_3$ | $CH_3$ |
| 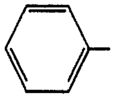 | 1 | H | 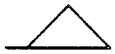 | $CH_3$ | $CH_3$ |
| 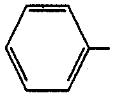 | 0 | H | $-CH_2CH{=}CH_2$ | $CH_3$ | $CH_3$ |
| 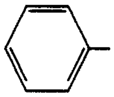 | 1 | H | $-CH_2CH{=}CH_2$ | $CH_3$ | $CH_3$ |
| 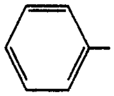 | 0 | H | $-(CH_2)_3-CH_3$ | $CH_3$ | $CH_3$ |
| 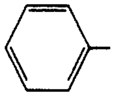 | 1 | H | $-(CH_2)_3-CH_3$ | $CH_3$ | $CH_3$ |

-continued
| | | | | | |
|---|---|---|---|---|---|
| 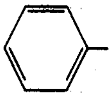 | 0 | H | $-CH_2CH(CH_3)_2$ | $CH_3$ | $CH_3$ |
| 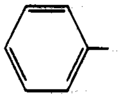 | 1 | H | $-CH_2CH(CH_3)_2$ | $CH_3$ | $CH_3$ |
| 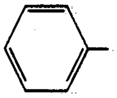 | 0 | H | $-(CH_2)_4-CH_3$ | $CH_3$ | $CH_3$ |
| 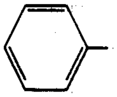 | 1 | H | $-(CH_2)_4-CH_3$ | $CH_3$ | $CH_3$ |
| 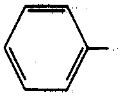 | 0 | H | $-(CH_2)_5-CH_3$ | $CH_3$ | $CH_3$ |
| 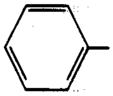 | 1 | H | $-(CH_2)_5-CH_3$ | $CH_3$ | $CH_3$ |
| 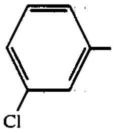 | 0 | H | $-CH_3$ | $CH_3$ | $CH_3$ |
| 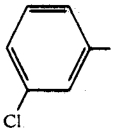 | 1 | H | $-CH_3$ | $CH_3$ | $CH_3$ |
| 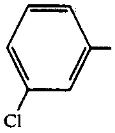 | 0 | H | $-C_2H_5$ | $CH_3$ | $CH_3$ |
| 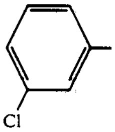 | 1 | H | $-C_2H_5$ | $CH_3$ | $CH_3$ |
| 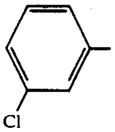 | 0 | H | $-CH_2CH_2CH_3$ | $CH_3$ | $CH_3$ |
| 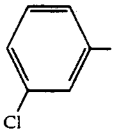 | 1 | H | $-CH_2CH_2CH_3$ | $CH_3$ | $CH_3$ |

-continued
| | | | | | |
|---|---|---|---|---|---|
| 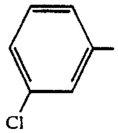 | 0 | H | $-CH(CH_3)_2$ | $CH_3$ | $CH_3$ |
| 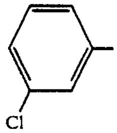 | 1 | H | $-CH(CH_3)_2$ | $CH_3$ | $CH_3$ |
| 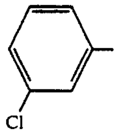 | 0 | H | 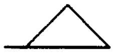 | $CH_3$ | $CH_3$ |
| 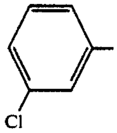 | 1 | H | 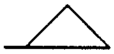 | $CH_3$ | $CH_3$ |
| 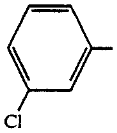 | 0 | H | $-CH_2CH{=}CH_2$ | $CH_3$ | $CH_3$ |
| 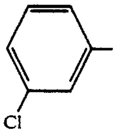 | 1 | H | $-CH_2CH{=}CH_2$ | $CH_3$ | $CH_3$ |
| 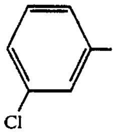 | 0 | H | $-(CH_2)_3-CH_3$ | $CH_3$ | $CH_3$ |
| 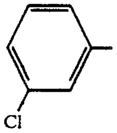 | 1 | H | $-(CH_2)_3-CH_3$ | $CH_3$ | $CH_3$ |
| 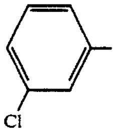 | 0 | H | $-CH_2CH(CH_3)_2$ | $CH_3$ | $CH_3$ |
| 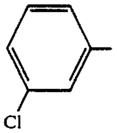 | 1 | H | $-CH_2CH(CH_3)_2$ | $CH_3$ | $CH_3$ |

-continued
| | | | | | |
|---|---|---|---|---|---|
| 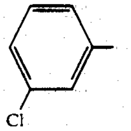 | 0 | H | $-(CH_2)_4-CH_3$ | $CH_3$ | $CH_3$ |
| 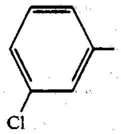 | 1 | H | $-(CH_2)_4-CH_3$ | $CH_3$ | $CH_3$ |
| 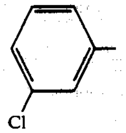 | 0 | H | $-(CH_2)_5-CH_3$ | $CH_3$ | $CH_3$ |
| 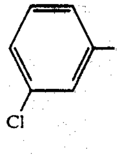 | 1 | H | $-(CH_2)_5-CH_3$ | $CH_3$ | $CH_3$ |
| 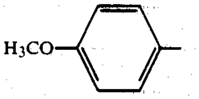 | 1 | H | $-CH_3$ | $CH_3$ | $CH_3$ |
| 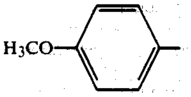 | 0 | H | $-C_2H_5$ | $CH_3$ | $CH_3$ |
| 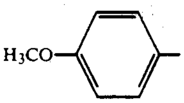 | 1 | H | $-C_2H_5$ | $CH_3$ | $CH_3$ |
| 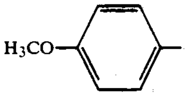 | 0 | H | $-CH_2CH_2CH_3$ | $CH_3$ | $CH_3$ |
| 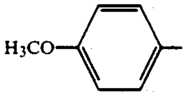 | 1 | H | $-CH_2CH_2CH_3$ | $CH_3$ | $CH_3$ |
| 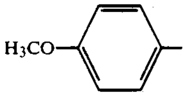 | 0 | H | $-CH(CH_3)_2$ | $CH_3$ | $CH_3$ |
| 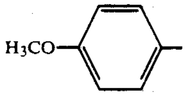 | 1 | H | $-CH(CH_3)_2$ | $CH_3$ | $CH_3$ |
| 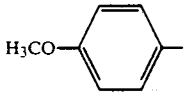 | 0 | H | 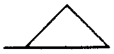 | $CH_3$ | $CH_3$ |

-continued
| | | | | | |
|---|---|---|---|---|---|
| 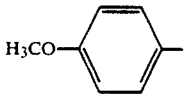 | 1 | H | 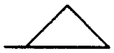 | $CH_3$ | $CH_3$ |
| 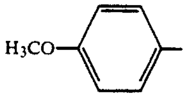 | 0 | H | $-CH_2CH{=}CH_2$ | $CH_3$ | $CH_3$ |
| 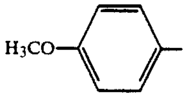 | 1 | H | $-CH_2CH{=}CH_2$ | $CH_3$ | $CH_3$ |
| 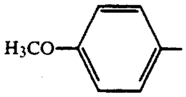 | 0 | H | $-(CH_2)_3-CH_3$ | $CH_3$ | $CH_3$ |
| 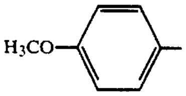 | 1 | H | $-(CH_2)_3-CH_3$ | $CH_3$ | $CH_3$ |
| 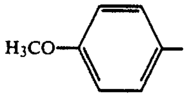 | 0 | H | $-CH_2CH(CH_3)_2$ | $CH_3$ | $CH_3$ |
| 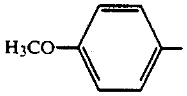 | 1 | H | $-CH_2CH(CH_3)_2$ | $CH_3$ | $CH_3$ |
| 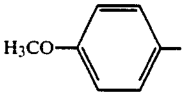 | 0 | H | $-(CH_2)_4-CH_3$ | $CH_3$ | $CH_3$ |
| 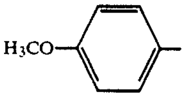 | 1 | H | $-(CH_2)_4-CH_3$ | $CH_3$ | $CH_3$ |
| 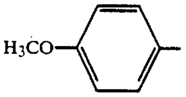 | 0 | H | $-(CH_2)_5-CH_3$ | $CH_3$ | $CH_3$ |
| 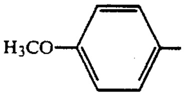 | 1 | H | $-(CH_2)_5-CH_3$ | $CH_3$ | $CH_3$ |
| 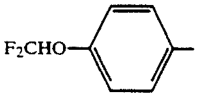 | 0 | H | $-CH_3$ | $CH_3$ | $CH_3$ |
| 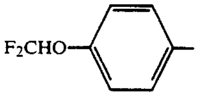 | 1 | H | $-CH_3$ | $CH_3$ | $CH_3$ |

-continued
| | | | | | |
|---|---|---|---|---|---|
| 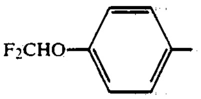 | 0 | H | $-C_2H_5$ | $CH_3$ | $CH_3$ |
| 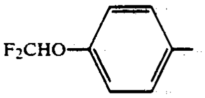 | 1 | H | $-C_2H_5$ | $CH_3$ | $CH_3$ |
| 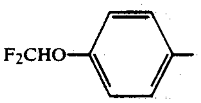 | 0 | H | $-CH_2CH_2CH_3$ | $CH_3$ | $CH_3$ |
| 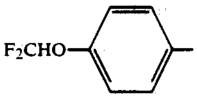 | 1 | H | $-CH_2CH_2CH_3$ | $CH_3$ | $CH_3$ |
| 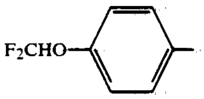 | 0 | H | $-CH(CH_3)_2$ | $CH_3$ | $CH_3$ |
| 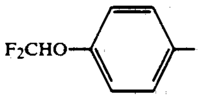 | 1 | H | $-CH(CH_3)_2$ | $CH_3$ | $CH_3$ |
| 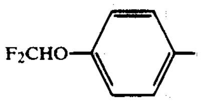 | 0 | H | 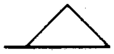 | $CH_3$ | $CH_3$ |
| 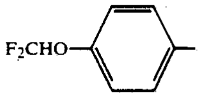 | 1 | H | 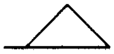 | $CH_3$ | $CH_3$ |
| 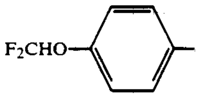 | 0 | H | $-CH_2CH{=}CH_2$ | $CH_3$ | $CH_3$ |
| 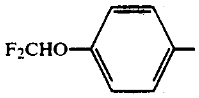 | 1 | H | $-CH_2CH{=}CH_2$ | $CH_3$ | $CH_3$ |
| 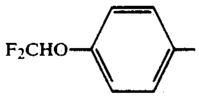 | 0 | H | $-(CH_2)_3-CH_3$ | $CH_3$ | $CH_3$ |
| 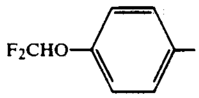 | 1 | H | $-(CH_2)_3-CH_3$ | $CH_3$ | $CH_3$ |
| 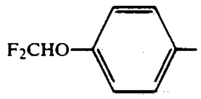 | 0 | H | $-CH_2CH(CH_3)_2$ | $CH_3$ | $CH_3$ |

-continued
| | | | | | |
|---|---|---|---|---|---|
| 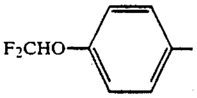 | 1 | H | $-CH_2CH(CH_3)_2$ | $CH_3$ | $CH_3$ |
| 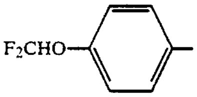 | 0 | H | $-(CH_2)_4-CH_3$ | $CH_3$ | $CH_3$ |
| 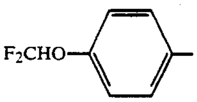 | 1 | H | $-(CH_2)_4-CH_3$ | $CH_3$ | $CH_3$ |
| 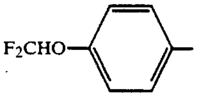 | 0 | H | $-(CH_2)_5-CH_3$ | $CH_3$ | $CH_3$ |
| 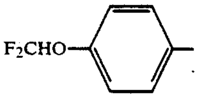 | 1 | H | $-(CH_2)_5-CH_3$ | $CH_3$ | $CH_3$ |
| 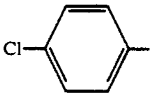 | 0 | $-CH_3$ | $-CH_3$ | $CH_3$ | $CH_3$ |
| 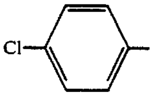 | 1 | $-CH_2CH=CH_2$ | $-C_2H_5$ | $CH_3$ | $CH_3$ |
| 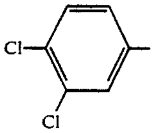 | 0 | $-CH_3$ | $-CH_2-CH_2-CH_3$ | $CH_3$ | $CH_3$ |
| 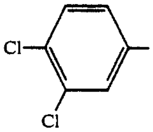 | 1 | $-CH_2CH=CH_2$ | $-CH(CH_3)_2$ | $CH_3$ | $CH_3$ |
| 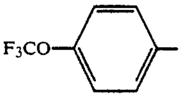 | 0 | $-CH_3$ | 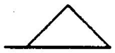 | $CH_3$ | $CH_3$ |
| 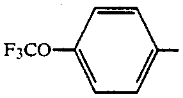 | 1 | $-CH_2CH=CH_2$ | $-CH_2CH=CH_2$ | $CH_3$ | $CH_3$ |
| 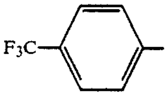 | 0 | $-CH_3$ | $-(CH_2)_3-CH_3$ | $CH_3$ | $CH_3$ |
| 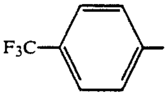 | 1 | $-CH_2CH=CH_2$ | $-CH_2CH(CH_3)_2$ | $CH_3$ | $CH_3$ |

-continued
| | | | | | |
|---|---|---|---|---|---|
| 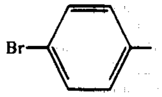 | 0 | $-CH_3$ | $-(CH_2)_4-CH_3$ | $CH_3$ | $CH_3$ |
| 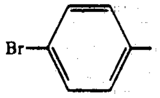 | 1 | $-CH_2CH=CH_2$ | $-(CH_2)_5-CH_3$ | $CH_3$ | $CH_3$ |
| 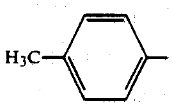 | 1 | $-CH_2CH=CH_2$ | $-CH_3$ | $CH_3$ | $CH_3$ |
| 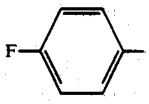 | 0 | $-CH_3$ | $-C_2H_5$ | $CH_3$ | $CH_3$ |
| 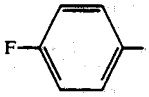 | 1 | $-CH_2CH=CH_2$ | $-CH_2CH_2CH_3$ | $CH_3$ | $CH_3$ |
| 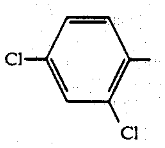 | 0 | $-CH_3$ | $-CH_3$ | $CH_3$ | $CH_3$ |
| 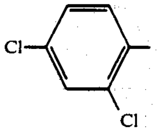 | 1 | $-CH_2CH=CH_2$ | $-C_2H_5$ | $CH_3$ | $CH_3$ |
| 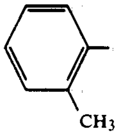 | 0 | $-CH_3$ | $-CH_2CH_2CH_3$ | $CH_3$ | $CH_3$ |
| 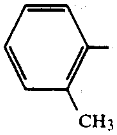 | 1 | $-CH_2CH=CH_2$ | $-CH(CH_3)_2$ | $CH_3$ | $CH_3$ |
| 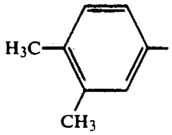 | 0 | $-CH_3$ | 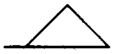 | $CH_3$ | $CH_3$ |
| 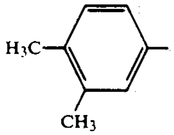 | 1 | $-CH_2CH=CH_2$ | $-CH_2CH=CH_2$ | $CH_3$ | $CH_3$ |

-continued
| | | | | | |
|---|---|---|---|---|---|
| 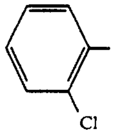 | 0 | $-CH_3$ | $-(CH_2)_3-CH_3$ | $CH_3$ | $CH_3$ |
| 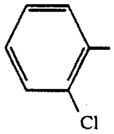 | 1 | $-CH_2CH=CH_2$ | $-CH_2CH(CH_3)_2$ | $CH_3$ | $CH_3$ |
| 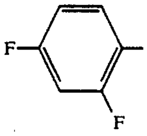 | 0 | $-CH_3$ | $-(CH_2)_4-CH_3$ | $CH_3$ | $CH_3$ |
| 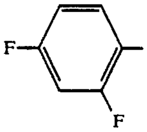 | 1 | $-CH_2CH=CH_2$ | $-(CH_2)_5-CH_3$ | $CH_3$ | $CH_3$ |
| 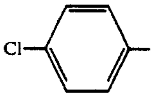 | 0 | H | $-CH_3$ | $-CH_2-CH_2-$ | |
| 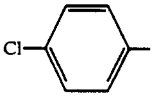 | 1 | H | $-CH_3$ | $-CH_2-CH_2-$ | |
| 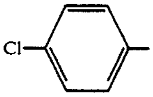 | 0 | H | $-C_2H_5$ | $-CH_2-CH_2-$ | |
| 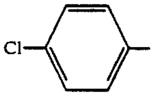 | 1 | H | $-C_2H_5$ | $-CH_2-CH_2-$ | |
| 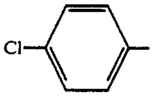 | 0 | H | $-CH_2CH_2CH_3$ | $-CH_2-CH_2-$ | |
| 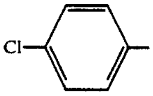 | 1 | H | $-CH_2CH_2CH_3$ | $-CH_2-CH_2-$ | |
| 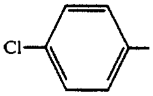 | 0 | H | $-CH(CH_3)_2$ | $-CH_2-CH_2-$ | |
| 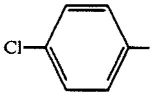 | 1 | H | $-CH(CH_3)_2$ | $-CH_2-CH_2-$ | |

-continued
| | | | | |
|---|---|---|---|---|
| 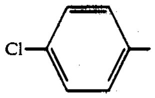 | 0 | H | 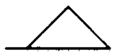 | $-CH_2-CH_2-$ |
| 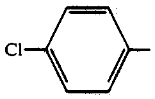 | 1 | H | 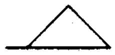 | $-CH_2-CH_2-$ |
| 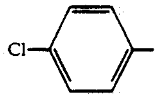 | 0 | H | $-CH_2CH{=}CH_2$ | $-CH_2-CH_2-$ |
| 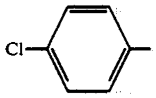 | 1 | H | $-CH_2CH{=}CH_2$ | $-CH_2-CH_2-$ |
| 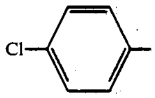 | 0 | H | $-(CH_2)_3-CH_3$ | $-CH_2-CH_2-$ |
| 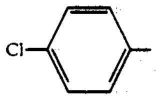 | 1 | H | $-(CH_2)_3-CH_3$ | $-CH_2-CH_2-$ |
| 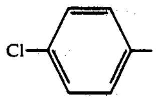 | 0 | H | $-CH_2CH(CH_3)_2$ | $-CH_2-CH_2-$ |
| 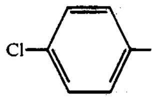 | 1 | H | $-CH_2CH(CH_3)_2$ | $-CH_2-CH_2-$ |
| 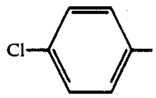 | 0 | H | $-(CH_2)_4-CH_3$ | $-CH_2-CH_2-$ |
| 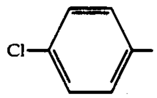 | 1 | H | $-(CH_2)_4-CH_3$ | $-CH_2-CH_2-$ |
| 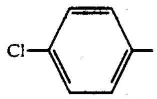 | 0 | H | $-(CH_2)_5-CH_3$ | $-CH_2-CH_2-$ |
| 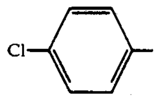 | 1 | H | $-(CH_2)_5-CH_3$ | $-CH_2-CH_2-$ |
| 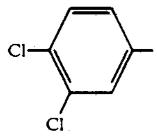 | 0 | H | $-CH_3$ | $-CH_2-CH_2-$ |

-continued
| | | | | |
|---|---|---|---|---|
| 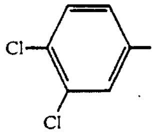 | 1 | H | $-CH_3$ | $-CH_2-CH_2-$ |
| 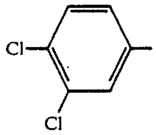 | 0 | H | $-C_2H_5$ | $-CH_2-CH_2-$ |
| 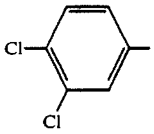 | 1 | H | $-C_2H_5$ | $-CH_2-CH_2-$ |
| 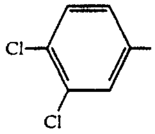 | 0 | H | $-CH_2CH_2CH_3$ | $-CH_2-CH_2-$ |
| 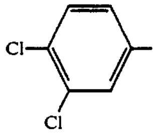 | 1 | H | $-CH_2CH_2CH_3$ | $-CH_2-CH_2-$ |
| 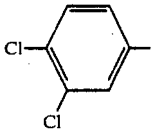 | 0 | H | $-CH(CH_3)_2$ | $-CH_2-CH_2-$ |
| 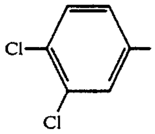 | 1 | H | $-CH(CH_3)_2$ | $-CH_2-CH_2-$ |
| 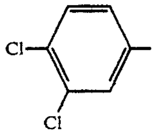 | 0 | H | 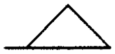 | $-CH_2-CH_2-$ |
| 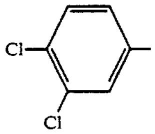 | 1 | H | 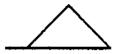 | $-CH_2-CH_2-$ |
| 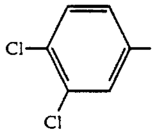 | 0 | H | $-CH_2CH=CH_2$ | $-CH_2-CH_2-$ |

-continued
| | | | | |
|---|---|---|---|---|
| 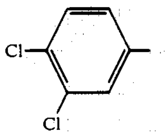 | 1 | H | $-CH_2CH=CH_2$ | $-CH_2-CH_2-$ |
| 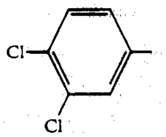 | 0 | H | $-(CH_2)_3-CH_3$ | $-CH_2-CH_2-$ |
| 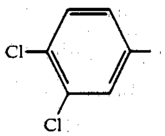 | 1 | H | $-(CH_2)_3-CH_3$ | $-CH_2-CH_2-$ |
| 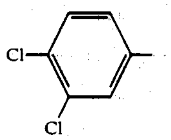 | 0 | H | $-CH_2CH(CH_3)_2$ | $-CH_2-CH_2-$ |
| 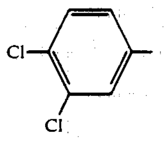 | 1 | H | $-CH_2CH(CH_3)_2$ | $-CH_2-CH_2-$ |
| 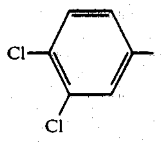 | 0 | H | $-(CH_2)_4-CH_3$ | $-CH_2-CH_2-$ |
| 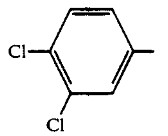 | 1 | H | $-(CH_2)_4-CH_3$ | $-CH_2-CH_2-$ |
| 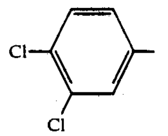 | 0 | H | $-(CH_2)_5-CH_3$ | $-CH_2-CH_2-$ |
| 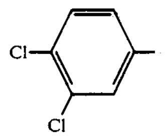 | 1 | H | $-(CH_2)_5-CH_3$ | $-CH_2-CH_2-$ |
| 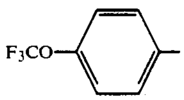 | 0 | H | $-CH_3$ | $-CH_2-CH_2-$ |
| 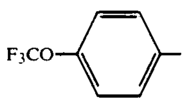 | 1 | H | $-CH_3$ | $-CH_2-CH_2-$ |

-continued
| | | | | |
|---|---|---|---|---|
| 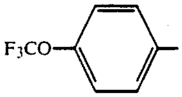 | 0 | H | $-C_2H_5$ | $-CH_2-CH_2-$ |
| 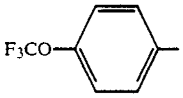 | 1 | H | $-C_2H_5$ | $-CH_2-CH_2-$ |
| 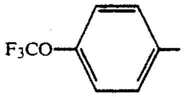 | 0 | H | $-CH_2CH_2CH_3$ | $-CH_2-CH_2-$ |
| 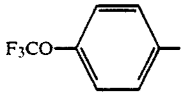 | 1 | H | $-CH_2CH_2CH_3$ | $-CH_2-CH_2-$ |
| 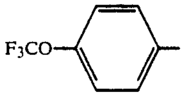 | 0 | H | $-CH(CH_3)_2$ | $-CH_2-CH_2-$ |
| 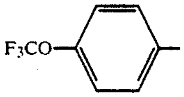 | 1 | H | $-CH(CH_3)_2$ | $-CH_2-CH_2-$ |
| 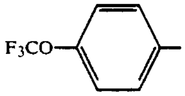 | 0 | H | 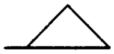 | $-CH_2-CH_2-$ |
| 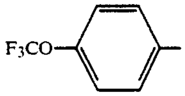 | 1 | H | 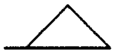 | $-CH_2-CH_2-$ |
| 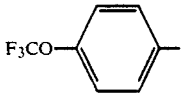 | 0 | H | $-CH_2CH=CH_2$ | $-CH_2-CH_2-$ |
| 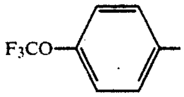 | 1 | H | $-CH_2CH=CH_2$ | $-CH_2-CH_2-$ |
| 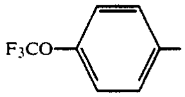 | 0 | H | $-(CH_2)_3-CH_3$ | $-CH_2-CH_2-$ |
| 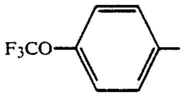 | 1 | H | $-(CH_2)_3-CH_3$ | $-CH_2-CH_2-$ |
| 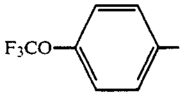 | 0 | H | $-CH_2CH(CH_3)_2$ | $-CH_2-CH_2-$ |

-continued
| | | | | |
|---|---|---|---|---|
| 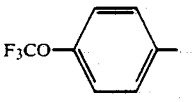 | 1 | H | $-CH_2CH(CH_3)_2$ | $-CH_2-CH_2-$ |
| 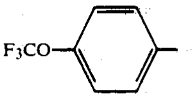 | 0 | H | $-(CH_2)_4-CH_3$ | $-CH_2-CH_2-$ |
| 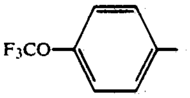 | 1 | H | $-(CH_2)_4-CH_3$ | $-CH_2-CH_2-$ |
| 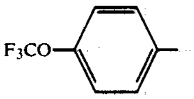 | 0 | H | $-(CH_2)_5-CH_3$ | $-CH_2-CH_2-$ |
| 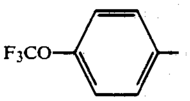 | 1 | H | $-(CH_2)_5-CH_3$ | $-CH_2-CH_2-$ |
| 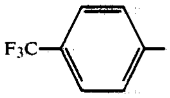 | 0 | H | $-CH_3$ | $-CH_2-CH_2-$ |
| 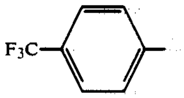 | 1 | H | $-CH_3$ | $-CH_2-CH_2-$ |
| 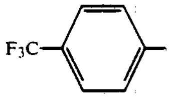 | 0 | H | $-C_2H_5$ | $-CH_2-CH_2-$ |
| 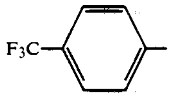 | 1 | H | $-C_2H_5$ | $-CH_2-CH_2-$ |
| 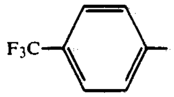 | 0 | H | $-CH_2CH_2CH_3$ | $-CH_2-CH_2-$ |
| 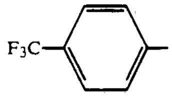 | 1 | H | $-CH_2CH_2CH_3$ | $-CH_2-CH_2-$ |
| 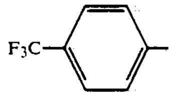 | 0 | H | $-CH(CH_3)_2$ | $-CH_2-CH_2-$ |
| 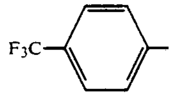 | 1 | H | $-CH(CH_3)_2$ | $-CH_2-CH_2-$ |

-continued
| | | | | |
|---|---|---|---|---|
| 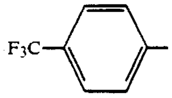 | 0 | H | 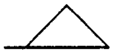 | $-CH_2-CH_2-$ |
| 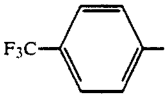 | 1 | H | 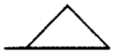 | $-CH_2-CH_2-$ |
| 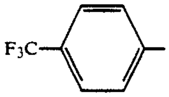 | 0 | H | $-CH_2CH{=}CH_2$ | $-CH_2-CH_2-$ |
| 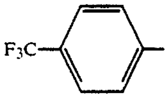 | 1 | H | $-CH_2CH{=}CH_2$ | $-CH_2-CH_2-$ |
| 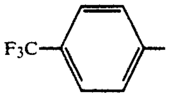 | 0 | H | $-(CH_2)_3-CH_3$ | $-CH_2-CH_2-$ |
| 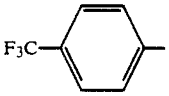 | 1 | H | $-(CH_2)_3-CH_3$ | $-CH_2-CH_2-$ |
| 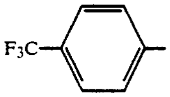 | 0 | H | $-CH_2CH(CH_3)_2$ | $-CH_2-CH_2-$ |
| 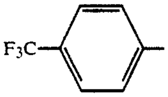 | 1 | H | $-CH_2CH(CH_3)_2$ | $-CH_2-CH_2-$ |
| 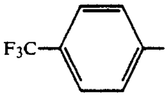 | 0 | H | $-(CH_2)_4-CH_3$ | $-CH_2-CH_2-$ |
| 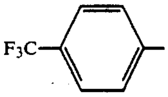 | 1 | H | $-(CH_2)_4-CH_3$ | $-CH_2-CH_2-$ |
| 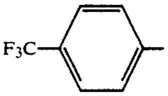 | 0 | H | $-(CH_2)_5-CH_3$ | $-CH_2-CH_2-$ |
| 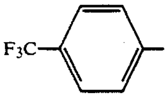 | 1 | H | $-(CH_2)_5-CH_3$ | $-CH_2-CH_2-$ |
| 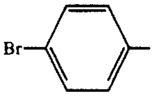 | 0 | H | $-CH_3$ | $-CH_2-CH_2-$ |

-continued
| | | | | |
|---|---|---|---|---|
| 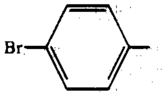 | 1 | H | $-CH_3$ | $-CH_2-CH_2-$ |
| 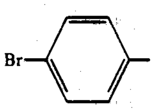 | 0 | H | $-C_2H_5$ | $-CH_2-CH_2-$ |
| 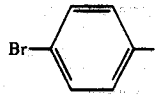 | 1 | H | $-C_2H_5$ | $-CH_2-CH_2-$ |
| 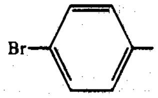 | 0 | H | $-CH_2CH_2CH_3$ | $-CH_2-CH_2-$ |
| 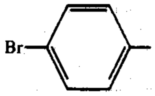 | 1 | H | $-CH_2CH_2CH_3$ | $-CH_2-CH_2-$ |
| 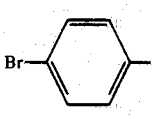 | 0 | H | $-CH(CH_3)_2$ | $-CH_2-CH_2-$ |
| 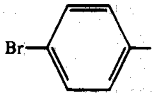 | 1 | H | $-CH(CH_3)_2$ | $-CH_2-CH_2-$ |
| 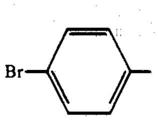 | 0 | H | 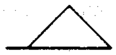 | $-CH_2-CH_2-$ |
| 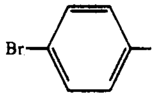 | 1 | H | 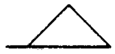 | $-CH_2-CH_2-$ |
| 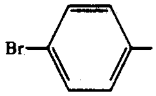 | 0 | H | $-CH_2CH=CH_2$ | $-CH_2-CH_2-$ |
| 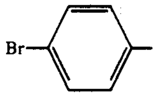 | 1 | H | $-CH_2CH=CH_2$ | $-CH_2-CH_2-$ |
| 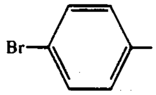 | 0 | H | $-(CH_2)_3-CH_3$ | $-CH_2-CH_2-$ |
| 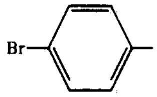 | 1 | H | $-(CH_2)_3-CH_3$ | $-CH_2-CH_2-$ |

-continued
| | | | | |
|---|---|---|---|---|
| 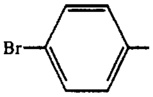 | 0 | H | $-CH_2CH(CH_3)_2$ | $-CH_2-CH_2-$ |
| 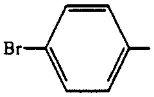 | 1 | H | $-CH_2CH(CH_3)_2$ | $-CH_2-CH_2-$ |
| 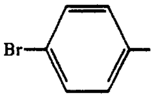 | 0 | H | $-(CH_2)_4-CH_3$ | $-CH_2-CH_2-$ |
| 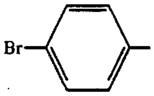 | 1 | H | $-(CH_2)_4-CH_3$ | $-CH_2-CH_2-$ |
| 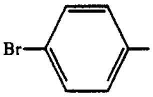 | 0 | H | $-(CH_2)_5-CH_3$ | $-CH_2-CH_2-$ |
| 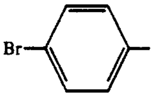 | 1 | H | $-(CH_2)_5-CH_3$ | $-CH_2-CH_2-$ |
| 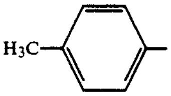 | 0 | H | $-CH_3$ | $-CH_2-CH_2-$ |
| 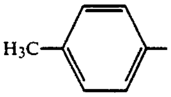 | 1 | H | $-CH_3$ | $-CH_2-CH_2-$ |
| 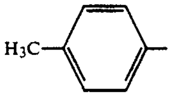 | 0 | H | $-C_2H_5$ | $-CH_2-CH_2-$ |
| 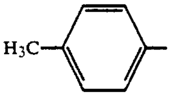 | 1 | H | $-C_2H_5$ | $-CH_2-CH_2-$ |
| 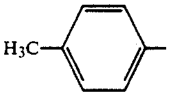 | 0 | H | $-CH_2CH_2CH_3$ | $-CH_2-CH_2-$ |
| 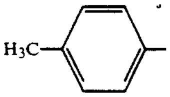 | 1 | H | $-CH_2CH_2CH_3$ | $-CH_2-CH_2-$ |
| 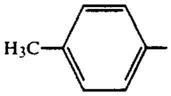 | 0 | H | $-CH(CH_3)_2$ | $-CH_2-CH_2-$ |

-continued
| | | | | |
|---|---|---|---|---|
| 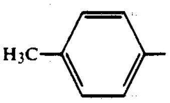 | 1 | H | $-CH(CH_3)_2$ | $-CH_2-CH_2-$ |
| 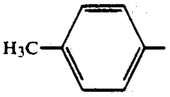 | 0 | H | 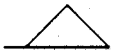 | $-CH_2-CH_2-$ |
| 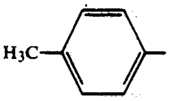 | 1 | H | 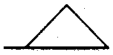 | $-CH_2-CH_2-$ |
| 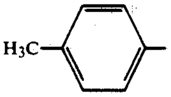 | 0 | H | $-CH_2CH=CH_2$ | $-CH_2-CH_2-$ |
| 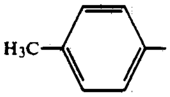 | 1 | H | $-CH_2CH=CH_2$ | $-CH_2-CH_2-$ |
| 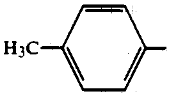 | 0 | H | $-(CH_2)_3-CH_3$ | $-CH_2-CH_2-$ |
| 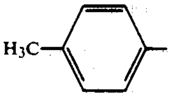 | 1 | H | $-(CH_2)_3-CH_3$ | $-CH_2-CH_2-$ |
| 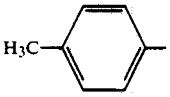 | 0 | H | $-CH_2CH(CH_3)_2$ | $-CH_2-CH_2-$ |
| 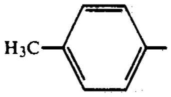 | 1 | H | $-CH_2CH(CH_3)_2$ | $-CH_2-CH_2-$ |
| 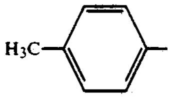 | 0 | H | $-(CH_2)_4-CH_3$ | $-CH_2-CH_2-$ |
| 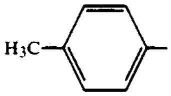 | 1 | H | $-(CH_2)_4-CH_3$ | $-CH_2-CH_2-$ |
| 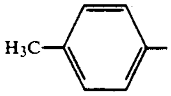 | 0 | H | $-(CH_2)_5-CH_3$ | $-CH_2-CH_2-$ |
| 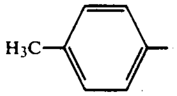 | 1 | H | $-(CH_2)_5-CH_3$ | $-CH_2-CH_2-$ |

-continued
| | | | | |
|---|---|---|---|---|
| 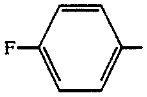 | 0 | H | $-CH_3$ | $-CH_2-CH_2-$ |
| 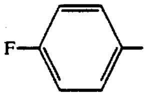 | 1 | H | $-CH_3$ | $-CH_2-CH_2-$ |
| 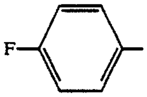 | 0 | H | $-C_2H_5$ | $-CH_2-CH_2-$ |
| 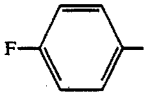 | 1 | H | $-C_2H_5$ | $-CH_2-CH_2-$ |
| 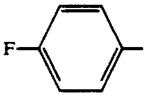 | 0 | H | $-CH_2CH_2CH_3$ | $-CH_2-CH_2-$ |
| 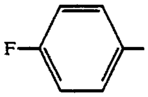 | 1 | H | $-CH_2CH_2CH_3$ | $-CH_2-CH_2-$ |
| 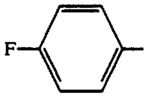 | 0 | H | $-CH(CH_3)_2$ | $-CH_2-CH_2-$ |
| 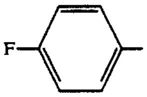 | 1 | H | $-CH(CH_3)_2$ | $-CH_2-CH_2-$ |
| 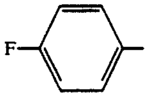 | 0 | H | 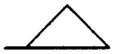 | $-CH_2-CH_2-$ |
| 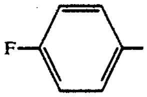 | 1 | H | 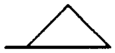 | $-CH_2-CH_2-$ |
| 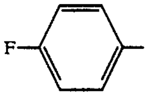 | 0 | H | $-CH_2CH=CH_2$ | $-CH_2-CH_2-$ |
| 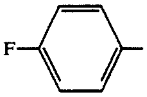 | 1 | H | $-CH_2CH=CH_2$ | $-CH_2-CH_2-$ |
| 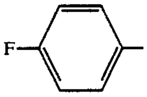 | 0 | H | $-(CH_2)_3-CH_3$ | $-CH_2-CH_2-$ |

-continued
| | | | | |
|---|---|---|---|---|
| 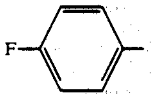 | 1 | H | $-(CH_2)_3-CH_3$ | $-CH_2-CH_2-$ |
| 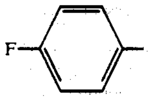 | 0 | H | $-CH_2CH(CH_3)_2$ | $-CH_2-CH_2-$ |
| 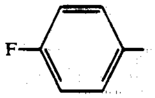 | 1 | H | $-CH_2CH(CH_3)_2$ | $-CH_2-CH_2-$ |
| 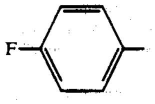 | 0 | H | $-(CH_2)_4-CH_3$ | $-CH_2-CH_2-$ |
| 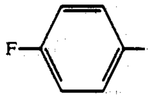 | 1 | H | $-(CH_2)_4-CH_3$ | $-CH_2-CH_2-$ |
| 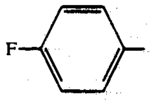 | 0 | H | $-(CH_2)_5-CH_3$ | $-CH_2-CH_2-$ |
| 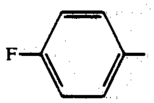 | 1 | H | $-(CH_2)_5-CH_3$ | $-CH_2-CH_2-$ |
| 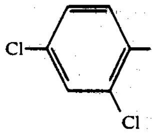 | 0 | H | $-CH_3$ | $-CH_2-CH_2-$ |
| 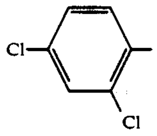 | 1 | H | $-CH_3$ | $-CH_2-CH_2-$ |
| 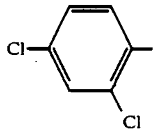 | 0 | H | $-C_2H_5$ | $-CH_2-CH_2-$ |
| 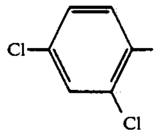 | 1 | H | $-C_2H_5$ | $-CH_2-CH_2-$ |
| 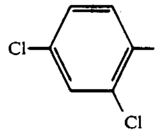 | 0 | H | $-CH_2CH_2CH_3$ | $-CH_2-CH_2-$ |

-continued
| | | | | |
|---|---|---|---|---|
| 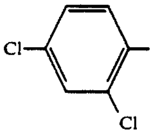 | 1 | H | $-CH_2CH_2CH_3$ | $-CH_2-CH_2-$ |
| 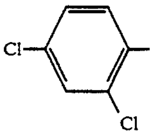 | 0 | H | $-CH(CH_3)_2$ | $-CH_2-CH_2-$ |
| 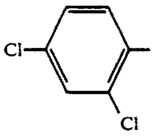 | 1 | H | $-CH(CH_3)_2$ | $-CH_2-CH_2-$ |
| 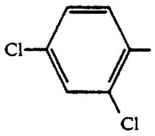 | 0 | H | 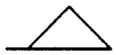 | $-CH_2-CH_2-$ |
| 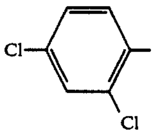 | 1 | H | 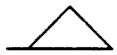 | $-CH_2-CH_2-$ |
| 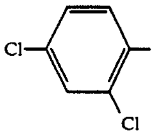 | 0 | H | $-CH_2CH=CH_2$ | $-CH_2-CH_2-$ |
| 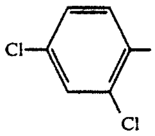 | 1 | H | $-CH_2CH=CH_2$ | $-CH_2-CH_2-$ |
| 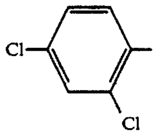 | 0 | H | $-(CH_2)_3-CH_3$ | $-CH_2-CH_2-$ |
| 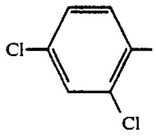 | 1 | H | $-(CH_2)_3-CH_3$ | $-CH_2-CH_2-$ |
| 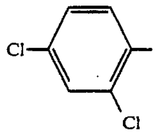 | 0 | H | $-CH_2CH(CH_3)_2$ | $-CH_2-CH_2-$ |

-continued
| | | | | |
|---|---|---|---|---|
| 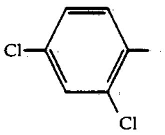 | 1 | H | $-CH_2CH(CH_3)_2$ | $-CH_2-CH_2-$ |
| 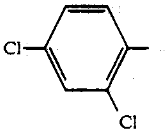 | 0 | H | $-(CH_2)_4-CH_3$ | $-CH_2-CH_2-$ |
| 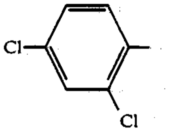 | 1 | H | $-(CH_2)_4-CH_3$ | $-CH_2-CH_2-$ |
| 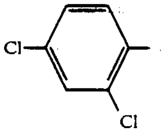 | 0 | H | $-(CH_2)_5-CH_3$ | $-CH_2-CH_2-$ |
| 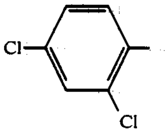 | 1 | H | $-(CH_2)_5-CH_3$ | $-CH_2-CH_2-$ |
| 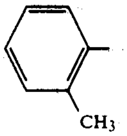 | 0 | H | $-CH_3$ | $-CH_2-CH_2-$ |
| 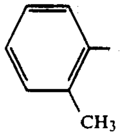 | 1 | H | $-CH_3$ | $-CH_2-CH_2-$ |
| 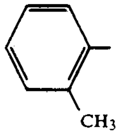 | 0 | H | $-C_2H_5$ | $-CH_2-CH_2-$ |
| 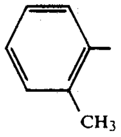 | 1 | H | $-C_2H_5$ | $-CH_2-CH_2-$ |
| 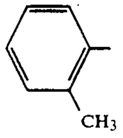 | 0 | H | $-CH_2CH_2CH_3$ | $-CH_2-CH_2-$ |

-continued
| | | | | |
|---|---|---|---|---|
| 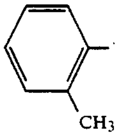 | 1 | H | $-CH_2CH_2CH_3$ | $-CH_2-CH_2-$ |
| 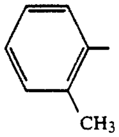 | 0 | H | $-CH(CH_3)_2$ | $-CH_2-CH_2-$ |
| 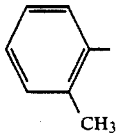 | 1 | H | $-CH(CH_3)_2$ | $-CH_2-CH_2-$ |
| 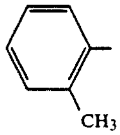 | 0 | H | 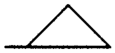 | $-CH_2-CH_2-$ |
| 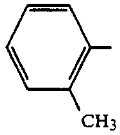 | 1 | H | 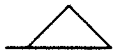 | $-CH_2-CH_2-$ |
| 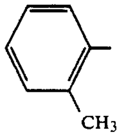 | 0 | H | $-CH_2CH{=}CH_2$ | $-CH_2-CH_2-$ |
| 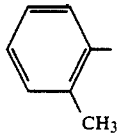 | 1 | H | $-CH_2CH{=}CH_2$ | $-CH_2-CH_2-$ |
| 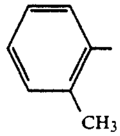 | 0 | H | $-(CH_2)_3-CH_3$ | $-CH_2-CH_2-$ |
| 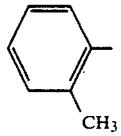 | 1 | H | $-(CH_2)_3-CH_3$ | $-CH_2-CH_2-$ |
| 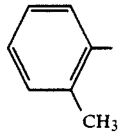 | 0 | H | $-CH_2CH(CH_3)_2$ | $-CH_2-CH_2-$ |

-continued
| | | | | |
|---|---|---|---|---|
| 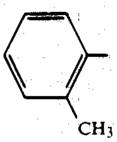 | 1 | H | $-CH_2CH(CH_3)_2$ | $-CH_2-CH_2-$ |
| 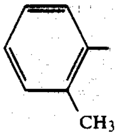 | 0 | H | $-(CH_2)_4-CH_3$ | $-CH_2-CH_2-$ |
| 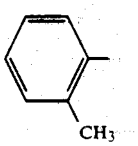 | 1 | H | $-(CH_2)_4-CH_3$ | $-CH_2-CH_2-$ |
| 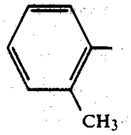 | 0 | H | $-(CH_2)_5-CH_3$ | $-CH_2-CH_2-$ |
| 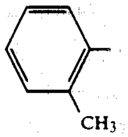 | 1 | H | $-(CH_2)_5-CH_3$ | $-CH_2-CH_2-$ |
| 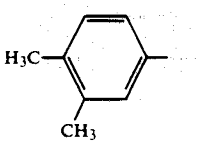 | 0 | H | $-CH_3$ | $-CH_2-CH_2-$ |
| 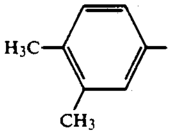 | 1 | H | $-CH_3$ | $-CH_2-CH_2-$ |
| 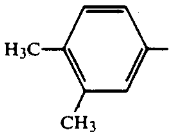 | 0 | H | $-C_2H_5$ | $-CH_2-CH_2-$ |
| 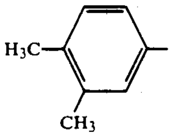 | 1 | H | $-C_2H_5$ | $-CH_2-CH_2-$ |
| 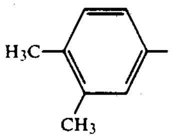 | 0 | H | $-CH_2CH_2CH_3$ | $-CH_2-CH_2-$ |

-continued
| | | | | |
|---|---|---|---|---|
| 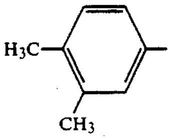 | 1 | H | $-CH_2CH_2CH_3$ | $-CH_2-CH_2-$ |
| 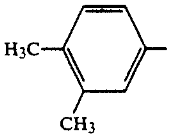 | 0 | H | $-CH(CH_3)_2$ | $-CH_2-CH_2-$ |
| 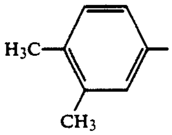 | 1 | H | $-CH(CH_3)_2$ | $-CH_2-CH_2-$ |
| 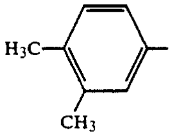 | 0 | H | 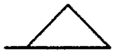 | $-CH_2-CH_2-$ |
| 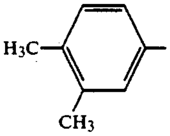 | 1 | H | 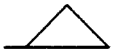 | $-CH_2-CH_2-$ |
| 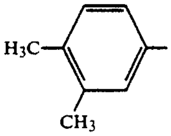 | 0 | H | $-CH_2CH{=}CH_2$ | $-CH_2-CH_2-$ |
| 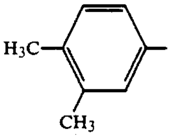 | 1 | H | $-CH_2CH{=}CH_2$ | $-CH_2-CH_2-$ |
| 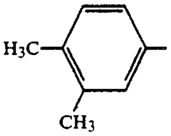 | 0 | H | $-(CH_2)_3-CH_3$ | $-CH_2-CH_2-$ |
| 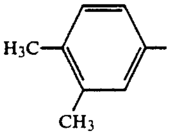 | 1 | H | $-(CH_2)_3-CH_3$ | $-CH_2-CH_2-$ |
| 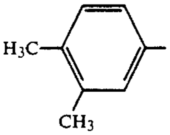 | 0 | H | $-CH_2CH(CH_3)_2$ | $-CH_2-CH_2-$ |

-continued
| | | | | |
|---|---|---|---|---|
| 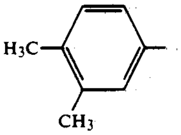 | 1 | H | $-CH_2CH(CH_3)_2$ | $-CH_2-CH_2-$ |
| 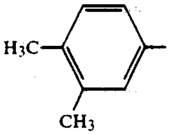 | 0 | H | $-(CH_2)_4-CH_3$ | $-CH_2-CH_2-$ |
| 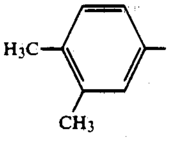 | 1 | H | $-(CH_2)_4-CH_3$ | $-CH_2-CH_2-$ |
| 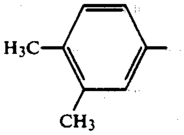 | 0 | H | $-(CH_2)_5-CH_3$ | $-CH_2-CH_2-$ |
| 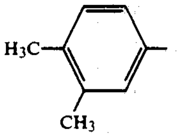 | 1 | H | $-(CH_2)_5-CH_3$ | $-CH_2-CH_2-$ |
| 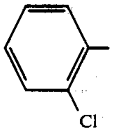 | 0 | H | $-CH_3$ | $-CH_2-CH_2-$ |
| 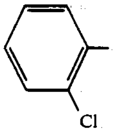 | 1 | H | $-CH_3$ | $-CH_2-CH_2-$ |
| 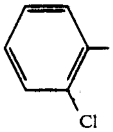 | 0 | H | $-C_2H_5$ | $-CH_2-CH_2-$ |
| 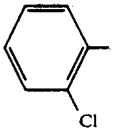 | 1 | H | $-C_2H_5$ | $-CH_2-CH_2-$ |
| 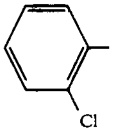 | 0 | H | $-CH_2CH_2CH_3$ | $-CH_2-CH_2-$ |

-continued
| | | | | |
|---|---|---|---|---|
| 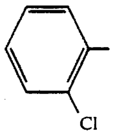 | 1 | H | $-CH_2CH_2CH_3$ | $-CH_2-CH_2-$ |
| 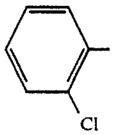 | 0 | H | $-CH(CH_3)_2$ | $-CH_2-CH_2-$ |
| 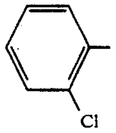 | 1 | H | $-CH(CH_3)_2$ | $-CH_2-CH_2-$ |
| 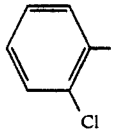 | 0 | H | 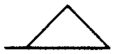 | $-CH_2-CH_2-$ |
| 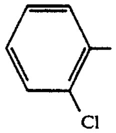 | 1 | H | 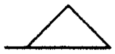 | $-CH_2-CH_2-$ |
| 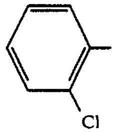 | 0 | H | $-CH_2CH{=}CH_2$ | $-CH_2-CH_2-$ |
| 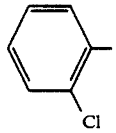 | 1 | H | $-CH_2CH{=}CH_2$ | $-CH_2-CH_2-$ |
| 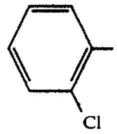 | 0 | H | $-(CH_2)_3-CH_3$ | $-CH_2-CH_2-$ |
| 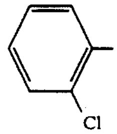 | 1 | H | $-(CH_2)_3-CH_3$ | $-CH_2-CH_2-$ |
| 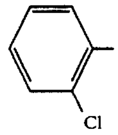 | 0 | H | $-CH_2CH(CH_3)_2$ | $-CH_2-CH_2-$ |

-continued
| | | | | |
|---|---|---|---|---|
| 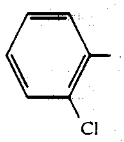 | 1 | H | $-CH_2CH(CH_3)_2$ | $-CH_2-CH_2-$ |
| 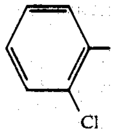 | 0 | H | $-(CH_2)_4-CH_3$ | $-CH_2-CH_2-$ |
| 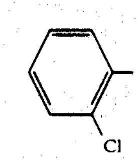 | 1 | H | $-(CH_2)_4-CH_3$ | $-CH_2-CH_2-$ |
| 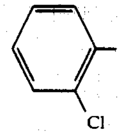 | 0 | H | $-(CH_2)_5-CH_3$ | $-CH_2-CH_2-$ |
| 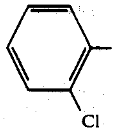 | 1 | H | $-(CH_2)_5-CH_3$ | $-CH_2-CH_2-$ |
| 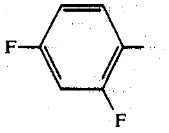 | 0 | H | $-CH_3$ | $-CH_2-CH_2-$ |
| 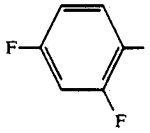 | 1 | H | $-CH_3$ | $-CH_2-CH_2-$ |
| 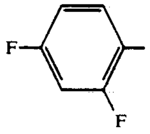 | 0 | H | $-C_2H_5$ | $-CH_2-CH_2-$ |
| 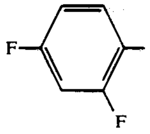 | 1 | H | $-C_2H_5$ | $-CH_2-CH_2-$ |
| 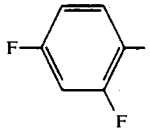 | 0 | H | $-CH_2CH_2CH_3$ | $-CH_2-CH_2-$ |

-continued
| | | | | |
|---|---|---|---|---|
| 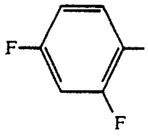 | 1 | H | $-CH_2CH_2CH_3$ | $-CH_2-CH_2-$ |
| 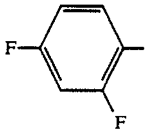 | 0 | H | $-CH(CH_3)_2$ | $-CH_2-CH_2-$ |
| 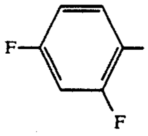 | 1 | H | $-CH(CH_3)_2$ | $-CH_2-CH_2-$ |
| 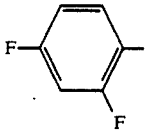 | 0 | H | 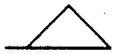 | $-CH_2-CH_2-$ |
| 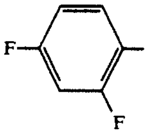 | 1 | H | 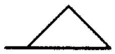 | $-CH_2-CH_2-$ |
| 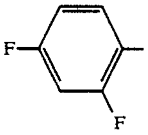 | 0 | H | $-CH_2CH{=}CH_2$ | $-CH_2-CH_2-$ |
| 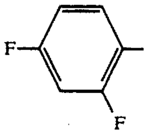 | 1 | H | $-CH_2CH{=}CH_2$ | $-CH_2-CH_2-$ |
| 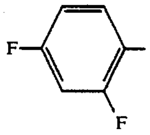 | 0 | H | $-(CH_2)_3-CH_3$ | $-CH_2-CH_2-$ |
| 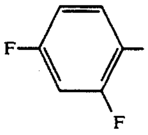 | 1 | H | $-(CH_2)_3-CH_3$ | $-CH_2-CH_2-$ |
| 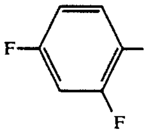 | 0 | H | $-CH_2CH(CH_3)_2$ | $-CH_2-CH_2-$ |

-continued
| | | | | |
|---|---|---|---|---|
| 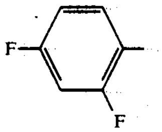 | 1 | H | $-CH_2CH(CH_3)_2$ | $-CH_2-CH_2-$ |
| 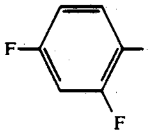 | 0 | H | $-(CH_2)_4-CH_3$ | $-CH_2-CH_2-$ |
| 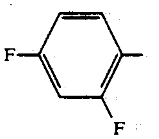 | 1 | H | $-(CH_2)_4-CH_3$ | $-CH_2-CH_2-$ |
| 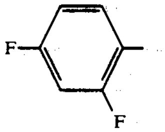 | 0 | H | $-(CH_2)_5-CH_3$ | $-CH_2-CH_2-$ |
| 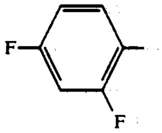 | 1 | H | $-(CH_2)_5-CH_3$ | $-CH_2-CH_2-$ |
| 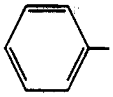 | 0 | H | $-CH_3$ | $-CH_2-CH_2-$ |
| 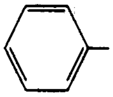 | 1 | H | $-CH_3$ | $-CH_2-CH_2-$ |
| 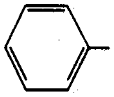 | 0 | H | $-C_2H_5$ | $-CH_2-CH_2-$ |
| 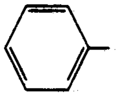 | 1 | H | $-C_2H_5$ | $-CH_2-CH_2-$ |
| 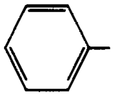 | 0 | H | $-CH_2CH_2CH_3$ | $-CH_2-CH_2-$ |
| 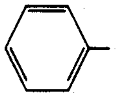 | 1 | H | $-CH_2CH_2CH_3$ | $-CH_2-CH_2-$ |
| 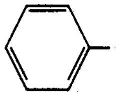 | 0 | H | $-CH(CH_3)_2$ | $-CH_2-CH_2-$ |

-continued
| | | | | |
|---|---|---|---|---|
| 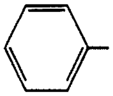 | 1 | H | $-CH(CH_3)_2$ | $-CH_2-CH_2-$ |
| 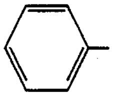 | 0 | H | 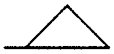 | $-CH_2-CH_2-$ |
| 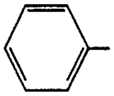 | 1 | H | 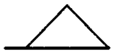 | $-CH_2-CH_2-$ |
| 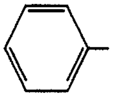 | 0 | H | $-CH_2CH{=}CH_2$ | $-CH_2-CH_2-$ |
| 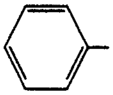 | 1 | H | $-CH_2CH{=}CH_2$ | $-CH_2-CH_2-$ |
| 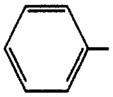 | 0 | H | $-(CH_2)_3-CH_3$ | $-CH_2-CH_2-$ |
| 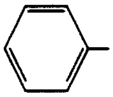 | 1 | H | $-(CH_2)_3-CH_3$ | $-CH_2-CH_2-$ |
| 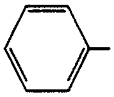 | 0 | H | $-CH_2CH(CH_3)_2$ | $-CH_2-CH_2-$ |
| 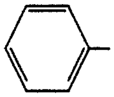 | 1 | H | $-CH_2CH(CH_3)_2$ | $-CH_2-CH_2-$ |
| 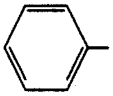 | 0 | H | $-(CH_2)_4-CH_3$ | $-CH_2-CH_2-$ |
| 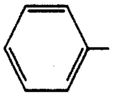 | 1 | H | $-(CH_2)_4-CH_3$ | $-CH_2-CH_2-$ |
| 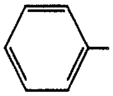 | 0 | H | $-(CH_2)_5-CH_3$ | $-CH_2-CH_2-$ |
| 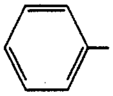 | 1 | H | $-(CH_2)_5-CH_3$ | $-CH_2-CH_2-$ |

-continued
| | | | | |
|---|---|---|---|---|
| 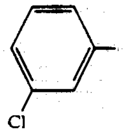 | 0 | H | $-CH_3$ | $-CH_2-CH_2-$ |
| 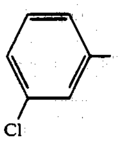 | 1 | H | $-CH_3$ | $-CH_2-CH_2-$ |
| 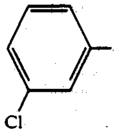 | 0 | H | $-C_2H_5$ | $-CH_2-CH_2-$ |
| 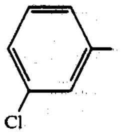 | 1 | H | $-C_2H_5$ | $-CH_2-CH_2-$ |
| 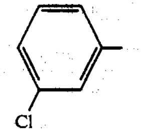 | 0 | H | $-CH_2CH_2CH_3$ | $-CH_2-CH_2-$ |
| 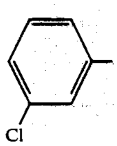 | 1 | H | $-CH_2CH_2CH_3$ | $-CH_2-CH_2-$ |
| 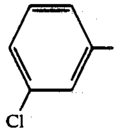 | 0 | H | $-CH(CH_3)_2$ | $-CH_2-CH_2-$ |
| 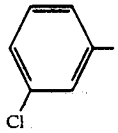 | 1 | H | $-CH(CH_3)_2$ | $-CH_2-CH_2-$ |
| 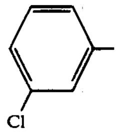 | 0 | H | 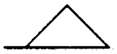 | $-CH_2-CH_2-$ |
| 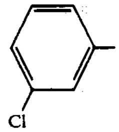 | 1 | H | 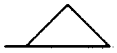 | $-CH_2-CH_2-$ |

-continued

| | | | | |
|---|---|---|---|---|
| 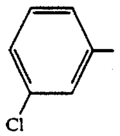 | 0 | H | $-CH_2CH{=}CH_2$ | $-CH_2-CH_2-$ |
| 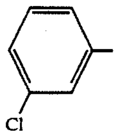 | 1 | H | $-CH_2CH{=}CH_2$ | $-CH_2-CH_2-$ |
| 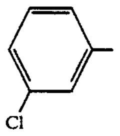 | 0 | H | $-(CH_2)_3-CH_3$ | $-CH_2-CH_2-$ |
| 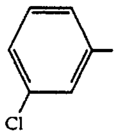 | 1 | H | $-(CH_2)_3-CH_3$ | $-CH_2-CH_2-$ |
| 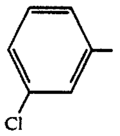 | 0 | H | $-CH_2CH(CH_3)_2$ | $-CH_2-CH_2-$ |
| 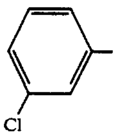 | 1 | H | $-CH_2CH(CH_3)_2$ | $-CH_2-CH_2-$ |
| 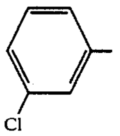 | 0 | H | $-(CH_2)_4-CH_3$ | $-CH_2-CH_2-$ |
| 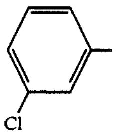 | 1 | H | $-(CH_2)_4-CH_3$ | $-CH_2-CH_2-$ |
| 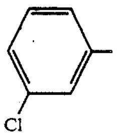 | 0 | H | $-(CH_2)_5-CH_3$ | $-CH_2-CH_2-$ |
| 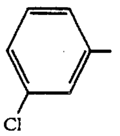 | 1 | H | $-(CH_2)_5-CH_3$ | $-CH_2-CH_2-$ |

If 1-(4-fluorobenzyl)-1-(1,2,4-triazol-1-yl-methyl-carbonyl)-cyclopropane and ethyl bromide are used as starting substances, pieces of aluminum foil as reaction auxiliaries and allyl bromide as a further reactant, the cource of process (a) according to the invention can be represented by the following equation:

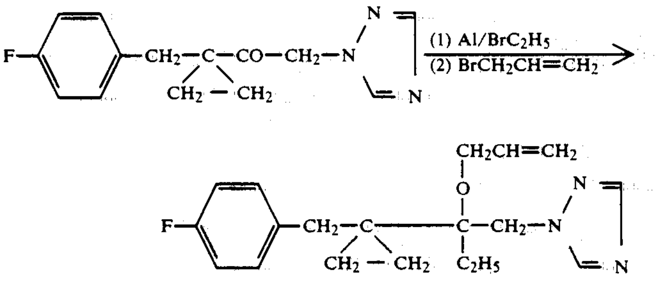

If 2-[2-(4-chlorophenoxy)-1,1-dimethyl-ethyl]-2-methyloxirane and 1,2,4-triazole are used as starting substances, the course of process (b) according to the invention can be represented by the following equation:

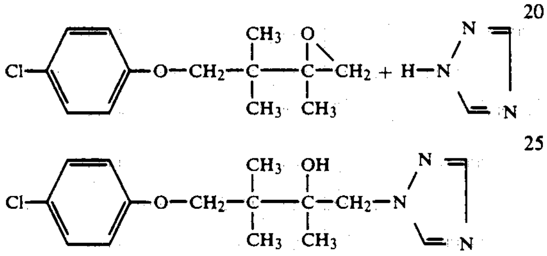

Formula (II) provides a general definition of the triazolyl methyl ketones to be used as starting substances in process (a) according to the invention.

In formula (II) in, Ar, $R^3$ and $R^4$ preferably, or in particular, have those meanings which have already been preferably mentioned above, or mentioned above as particularly preferred for in, Ar, $R^3$ and $R^7$ in connection with the description of the compounds of the formula (I) according to the invention.

Examples of the starting substances of the formula (II) are listed in Table 2 below:

TABLE 2

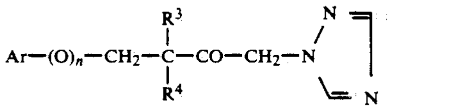 (II)

| Ar | n | $R^3$ | $R^4$ |
|---|---|---|---|
| 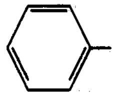 | 0 | $-CH_3$ | $-CH_3$ |
| 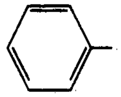 | 1 | $-CH_3$ | $-CH_3$ |
| 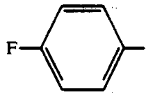 | 0 | $-CH_3$ | $-CH_3$ |
| 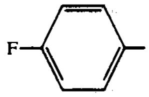 | 1 | $-CH_3$ | $-CH_3$ |

TABLE 2-continued

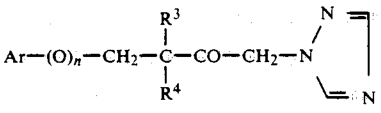 (II)

| Ar | n | $R^3$ | $R^4$ |
|---|---|---|---|
| 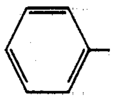 | 0 | $-CH_2-CH_2-$ | |
| 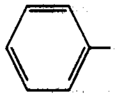 | 1 | $-CH_2-CH_2-$ | |
| 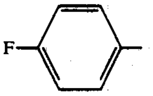 | 0 | $-CH_2-CH_2-$ | |
| 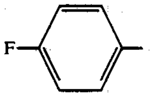 | 1 | $-CH_2-CH_2-$ | |
| 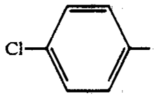 | 0 | $-CH_3$ | $-CH_3$ |
| 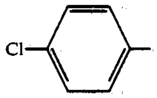 | 1 | $-CH_3$ | $-CH_3$ |
| 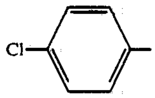 | 0 | $-CH_2-CH_2-$ | |
| 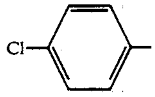 | 1 | $-CH_2-CH_2-$ | |
| 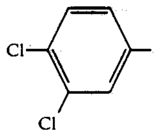 | 0 | $-CH_3$ | $-CH_3$ |

TABLE 2-continued
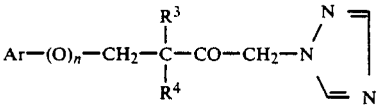
(II)
| Ar | n | $R^3$ | $R^4$ |
|---|---|---|---|
| 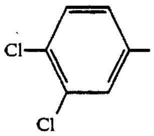 | 1 | $-CH_3$ | $-CH_3$ |
| 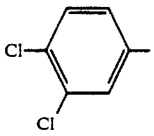 | 0 | $-CH_2-CH_2-$ | |
| 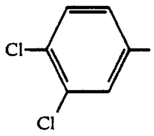 | 1 | $-CH_2-CH_2-$ | |
| 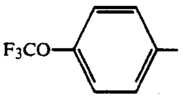 | 0 | $-CH_3$ | $-CH_3$ |
| 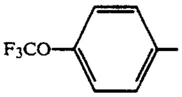 | 1 | $-CH_3$ | $-CH_3$ |
| 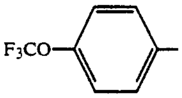 | 0 | $-CH_2-CH_2-$ | |
| 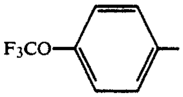 | 1 | $-CH_2-CH_2-$ | |
| 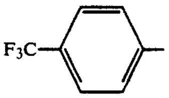 | 0 | $-CH_3$ | $-CH_3$ |
| 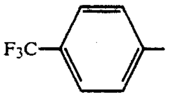 | 1 | $-CH_3$ | $-CH_3$ |
| 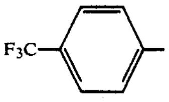 | 0 | $-CH_2-CH_2-$ | |
| 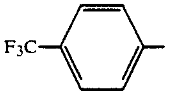 | 1 | $-CH_2-CH_2-$ | |
TABLE 2-continued
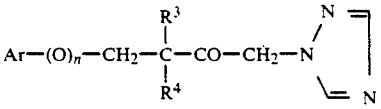
(II)
| Ar | n | $R^3$ | $R^4$ |
|---|---|---|---|
| 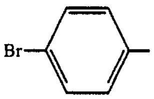 | 0 | $-CH_3$ | $-CH_3$ |
| 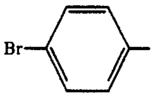 | 1 | $-CH_3$ | $-CH_3$ |
| 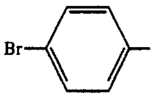 | 0 | $-CH_2-CH_2-$ | |
| 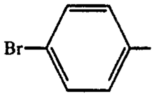 | 1 | $-CH_2-CH_2-$ | |
| 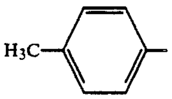 | 0 | $-CH_3$ | $-CH_3$ |
| 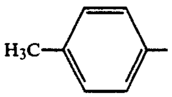 | 1 | $-CH_3$ | $-CH_3$ |
| 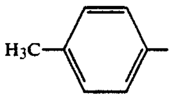 | 0 | $-CH_2-CH_2-$ | |
| 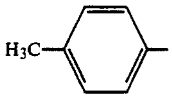 | 1 | $-CH_2-CH_2-$ | |
| 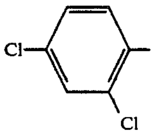 | 0 | $-CH_3$ | $-CH_3$ |
| 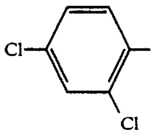 | 1 | $-CH_3$ | $-CH_3$ |
| 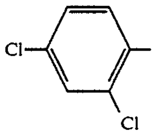 | 0 | $-CH_2-CH_2-$ | |

TABLE 2-continued
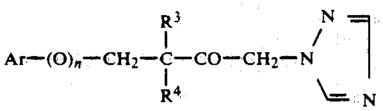
(II)
| Ar | n | $R^3$ | $R^4$ |
|---|---|---|---|
| 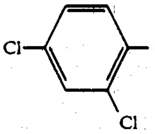 | 1 | $-CH_2-CH_2-$ | |
| 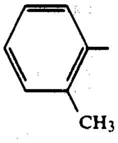 | 0 | $-CH_3$ | $-CH_3$ |
| 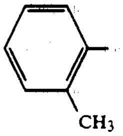 | 1 | $-CH_3$ | $-CH_3$ |
| 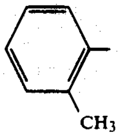 | 0 | $-CH_2-CH_2-$ | |
| 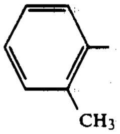 | 1 | $-CH_2-CH_2-$ | |
| 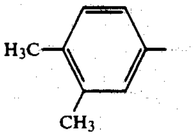 | 0 | $-CH_3$ | $-CH_3$ |
| 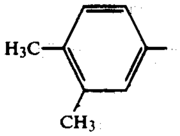 | 1 | $-CH_3$ | $-CH_3$ |
| 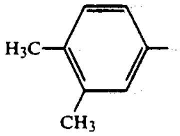 | 0 | $-CH_2-CH_2-$ | |
| 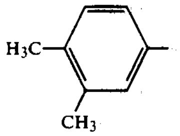 | 1 | $-CH_2-CH_2-$ | |
TABLE 2-continued
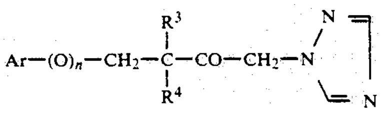
(II)
| Ar | n | $R^3$ | $R^4$ |
|---|---|---|---|
| 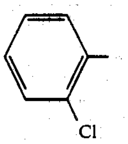 | 0 | $-CH_3$ | $-CH_3$ |
| 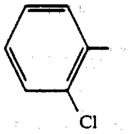 | 1 | $-CH_3$ | $-CH_3$ |
| 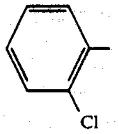 | 0 | $-CH_2-CH_2-$ | |
| 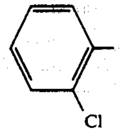 | 1 | $-CH_2-CH_2-$ | |
| 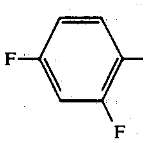 | 0 | $-CH_3$ | $-CH_3$ |
| 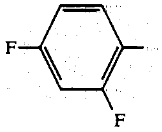 | 1 | $-CH_3$ | $-CH_3$ |
| 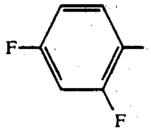 | 0 | $-CH_2-CH_2-$ | |
| 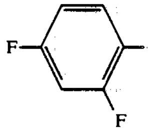 | 1 | $-CH_2-CH_2-$ | |
| 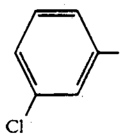 | 0 | $-CH_3$ | $-CH_3$ |

TABLE 2-continued

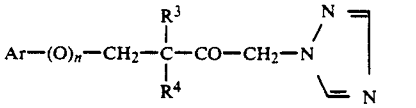

(II)

| Ar | n | $R^3$ | $R^4$ |
|---|---|---|---|
| 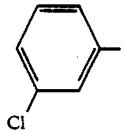 | 1 | $-CH_3$ | $-CH_3$ |
| 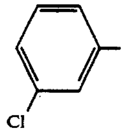 | 0 | $-CH_2-CH_2-$ | |
| 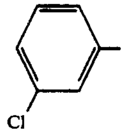 | 1 | $-CH_2-CH_2-$ | |
| 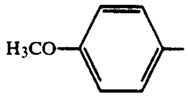 | 0 | $-CH_3$ | $-CH_3$ |
| 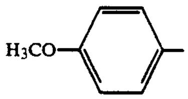 | 1 | $-CH_3$ | $-CH_3$ |
| 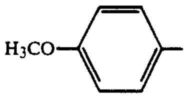 | 0 | $-CH_2-CH_2-$ | |
| 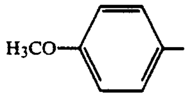 | 1 | $-CH_2-CH_2-$ | |
| 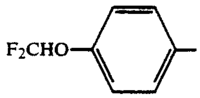 | 0 | $-CH_3$ | $-CH_3$ |
| 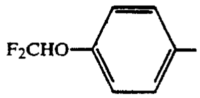 | 1 | $-CH_3$ | $-CH_3$ |
| 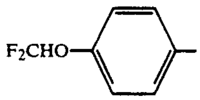 | 0 | $-CH_2-CH_2-$ | |
| 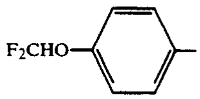 | 1 | $-CH_2-CH_2-$ | |

The triazolyl methyl ketones of the formula (II) are known or can be prepared by processes known per se (cf. EP-OS (European Patent Specification) No. 0,054,865).

Formula (III) provides a general definition of the halogen compounds also to be used as starting substances in process (a) according to the invention.

In formula (III), $R^2$ preferably, or in particular, has the meaning which has already preferably been mentioned above, or mentioned above as particularly preferred, for $R^2$ in connection with the description of the compounds of the formula (I) according to the invention, and X preferably stands for chlorine, bromine or iodine.

Examples of the starting substances of the formula (III) which may be mentioned are: methyl chloride, methyl bromide, methyl iodide, ethyl chloride, ethyl bromide, ethyl iodide, propyl chloride, propyl bromide, propyl iodide, isopropyl chloride, isopropyl bromide, isopropyl iodide, butyl chloride, butyl bromide, butyl iodide, isobutyl chloride, isobutyl bromide, isobutyl iodide, sec-butyl chloride, sec-butyl bromide, sec-butyl iodide, pentyl chloride, pentyl bromide, pentyl iodide, hexyl chloride, hexyl bromide, hexyl iodide, cyclopropyl chloride, cyclopropyl bromide, cyclopropyl iodide, allyl chloride, allyl bromide and allyl iodide.

The halogen compounds of the formula (III) are known chemicals for organic synthesis.

Formula (IV) provides a general definition of the compounds also to be used as reactants in process (a) according to the invention.

In formula (IV), $R^1$ preferably, or in particular, has the meaning which has already been preferably mentioned above, or mentioned above as particularly preferred, for $R^1$ in connection with the description of the compounds of the formula (I) according to the invention, and Y preferably stands for chlorine, bromine or iodine.

Examples of the starting substances of the formula (IV) which may be mentioned are: hydrogen chloride, hydrogen bromide, hydrogen iodide, methyl bromide, methyl chloride, methyl iodide, ethyl bromide, ethyl chloride, ethyl iodide, propyl bromide, propyl chloride, propyl iodide, isopropyl bromide, isopropyl chloride, isopropyl iodide, butyl bromide, butyl chloride, butyl iodide, isobutyl bromide, isobutyl chloride, isobutyl iodide, sec-butyl bromide, sec-butyl chloride, sec-butyl iodide, pentyl bromide, pentyl chloride, pentyl iodide, cyclopropyl bromide, cyclopropyl chloride, cyclopropyl iodide, allyl bromide, allyl chloride and allyl iodide.

The compounds of the formula (IV) are known chemicals for organic synthesis.

Process (a) according to the invention is carried out in the presence of aluminium and if appropriate in the presence of substances which are suitable for activating aluminium. In particular, such substances are halogens or metal halides, for example bromine, iodine, aluminum chloride or aluminum bromide, mercury(II) chloride, copper(II) chloride and silver(I) chloride.

Process (a) according to the invention is preferably carried out using diluents. Suitable diluents in this process are virtually all inert organic solvents. Aliphatic and aromatic hydrocarbons, such as pentane, hexane, heptane, cyclohexane, petroleum ether, benzine, ligroin, benzene, toluene and xylene, ethers, such as diethyl ether, dibutyl ether, glycol dimethyl ether, diglycol dimethyl ether, tetrahydrofuran and dioxane, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylenesulphone and hexamethylphosphoric triamide can preferably be used.

When carrying out process (a) according to the invention, the reaction temperatures can be varied within a relatively wide range. In general, the process is carried out at temperatures between −50° C. and +150° C., preferably at temperatures between −30° C. and +100° C.

In general, process (a) according to the invention is carried out under atmospheric pressure. However, it is also possible to carry out the process under increased or reduced pressure.

For carrying out process (a) according to the invention, between 1 and 3 moles, preferably between 1.5 and 2.5 moles, of halogen compound of the formula (III) and between 1 and 3 moles, preferably between 1.5 and 2.5 moles, of aluminum, if appropriate as a mixture with the aluminium activator, are generally employed, and also between 1 and 20 moles, preferably between 1 and 10 moles of a compound of the formula (IV) are employed per 1 mole of triazolyl methyl ketone of the formula (II).

In general, a procedure is followed in which, if appropriate, the aluminum is initially treated with one or more substances suitable for activating aluminum, preferably in an ultrasonic bath and using a diluent, then reacted with a halogen compound of the formula (III), and subsequently reacted with a triazolyl methyl ketone of the formula (II) and finally with a compound of the formula (IV).

In the event that the compounds of the formula (IV) are hydrogen halides, they can in a way also be reacted in the course of working up, using aqueous solutions thereof, such as, for example, hydrochloric acid.

Working up can be carried out by customary methods. For example, the reaction mixture is diluted with water or with an aqueous acid, and, if desired, the major part of the organic solvent is distilled off, if desired, the pH is rendered weakly alkaline with a base, such as, for example, ammonia, if desired, the mixture is diluted with water and filtered, if appropriate with suction, after a virtually water-immiscible organic solvent, such as, for example ethyl acetate, has been added. The organic phase of the filtrate is separated off, washed with water, treated with a drying agent, such as, for example, sodium sulphate, and filtered. The solvent is distilled off from the filtrate under a waterpump vacuum, and, if appropriate, the crude product which is obtained as the residue is purified by customary methods, for example by means of column chromatography.

Formula (V) provides a general definition of the oxiranes to be used as starting substances in process (b) according to the invention.

In formula (V), n, Ar, $R^2$, $R^3$ and $R^4$ preferably, or in particular, have those meanings which have already preferably been mentioned above, or mentioned above as particularly preferred, for n, Ar, $R^2$, $R^3$ and $R^4$ in connection with the description of the compounds of the formula (I) according to the invention.

Examples of the starting substances of the formula (V) are listed in Table 3 below:

TABLE 3

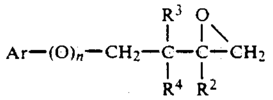

| Ar | n | $R^2$ | $R^3$ | $R^4$ |
|---|---|---|---|---|
| 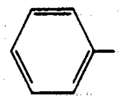 | 0 | $-CH_3$ | $-CH_3$ | $-CH_3$ |
| 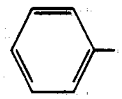 | 1 | $-CH_3$ | $-CH_3$ | $-CH_3$ |
| 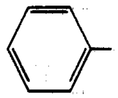 | 0 | $-CH_3$ | $-CH_2-CH_2-$ | |
| 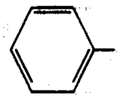 | 1 | $-CH_3$ | $-CH_2-CH_2-$ | |
| 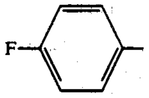 | 0 | $-CH_3$ | $-CH_3$ | |
| 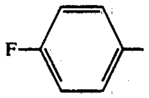 | 1 | $-CH_3$ | $-CH_3$ | |
| 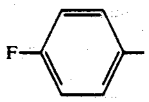 | 0 | $-CH_3$ | $-CH_2-CH_2-$ | |
| 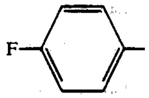 | 1 | $-CH_3$ | $-CH_2-CH_2-$ | |
| 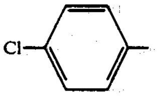 | 0 | $-CH_3$ | $-CH_3$ | $-CH_3$ |
| 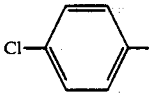 | 1 | $-CH_3$ | $-CH_3$ | $-CH_3$ |
| 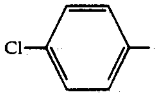 | 0 | $C_2H_5$ | $-CH_3$ | $-CH_3$ |
| 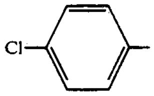 | 1 | $-C_2H_5$ | $-CH_3$ | $-CH_3$ |

TABLE 3-continued

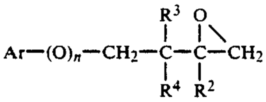

| Ar | n | $R^2$ | $R^3$ | $R^4$ |
|---|---|---|---|---|
| 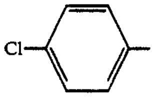 | 0 | $-CH_2CH_2CH_3$ | $-CH_3$ | $-CH_3$ |
| 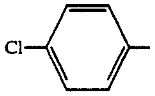 | 1 | $-CH_2CH_2CH_3$ | $-CH_3$ | $-CH_3$ |
| 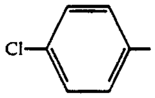 | 0 | $-CH(CH_3)_2$ | $-CH_3$ | $-CH_3$ |
| 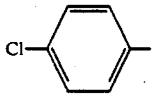 | 1 | $-CH(CH_3)_2$ | $-CH_3$ | $-CH_3$ |
| 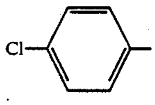 | 0 | 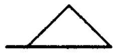 | $-CH_3$ | $-CH_3$ |
| 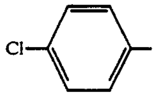 | 1 | 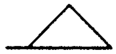 | $-CH_3$ | $-CH_3$ |
| 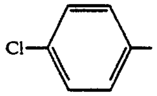 | 0 | $-CH_2CH{=}CH_2$ | $-CH_3$ | $-CH_3$ |
| 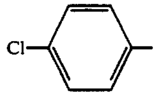 | 1 | $-CH_2CH{=}CH_2$ | $-CH_3$ | $-CH_3$ |
| 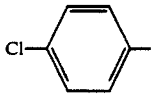 | 0 | $-(CH_2)_3-CH_3$ | $-CH_3$ | $-CH_3$ |
| 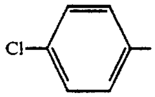 | 1 | $-(CH_2)_3-CH_3$ | $-CH_3$ | $-CH_3$ |
| 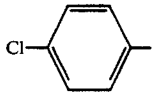 | 0 | $-CH_2CH(CH_3)_2$ | $-CH_3$ | $-CH_3$ |
| 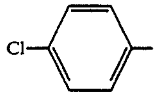 | 1 | $-CH_2CH(CH_3)_2$ | $-CH_3$ | $-CH_3$ |

TABLE 3-continued

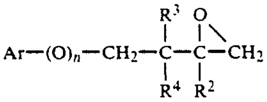

| Ar | n | $R^2$ | $R^3$ | $R^4$ |
|---|---|---|---|---|
| 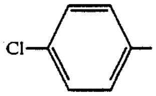 | 0 | $-(CH_2)_4-CH_3$ | $-CH_3$ | $-CH_3$ |
| 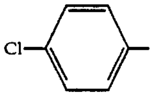 | 1 | $-(CH_2)_4-CH_3$ | $-CH_3$ | $-CH_3$ |
| 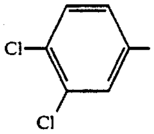 | 0 | $-CH_3$ | $-CH_3$ | $-CH_3$ |
| 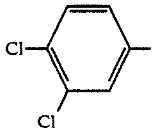 | 1 | $-CH_3$ | $-CH_3$ | $-CH_3$ |
| 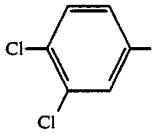 | 0 | $C_2H_5$ | $-CH_3$ | $-CH_3$ |
| 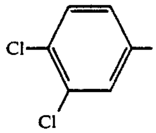 | 1 | $-C_2H_5$ | $-CH_3$ | $-CH_3$ |
| 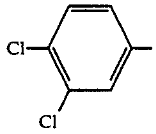 | 0 | $-CH_2CH_2CH_3$ | $-CH_3$ | $-CH_3$ |
| 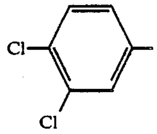 | 1 | $-CH_2CH_2CH_3$ | $-CH_3$ | $-CH_3$ |
| 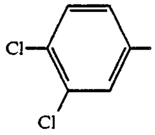 | 0 | $-CH(CH_3)_2$ | $-CH_3$ | $-CH_3$ |
| 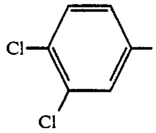 | 1 | $-CH(CH_3)_2$ | $-CH_3$ | $-CH_3$ |

TABLE 3-continued

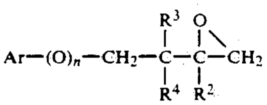

| Ar | n | $R^2$ | $R^3$ | $R^4$ |
|---|---|---|---|---|
| 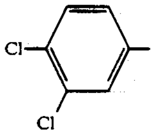 | 0 | 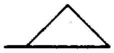 | $-CH_3$ | $-CH_3$ |
| 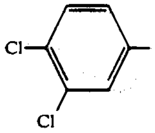 | 1 | 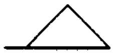 | $-CH_3$ | $-CH_3$ |
| 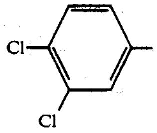 | 0 | $-CH_2CH=CH_2$ | $-CH_3$ | $-CH_3$ |
| 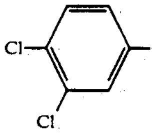 | 1 | $-CH_2CH=CH_2$ | $-CH_3$ | $-CH_3$ |
| 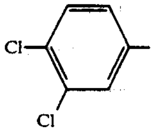 | 0 | $-(CH_2)_3-CH_3$ | $-CH_3$ | $-CH_3$ |
| 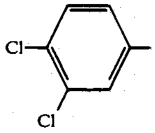 | 1 | $-(CH_2)_3-CH_3$ | $-CH_3$ | $-CH_3$ |
| 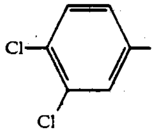 | 0 | $-CH_2CH(CH_3)_2$ | $-CH_3$ | $-CH_3$ |
| 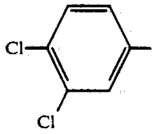 | 1 | $-CH_2CH(CH_3)_2$ | $-CH_3$ | $-CH_3$ |
| 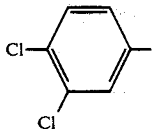 | 1 | $-(CH_2)_4-CH_3$ | $-CH_3$ | $-CH_3$ |

TABLE 3-continued

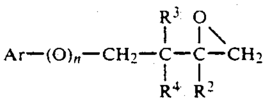

| Ar | n | $R^2$ | $R^3$ | $R^4$ |
|---|---|---|---|---|
| 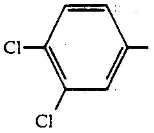 | 1 | $-(CH_2)_4-CH_3$ | $-CH_3$ | $-CH_3$ |
| 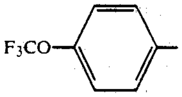 | 0 | $-CH_3$ | $-CH_3$ | $-CH_3$ |
| 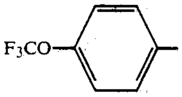 | 1 | $-CH_3$ | $-CH_3$ | $-CH_3$ |
| 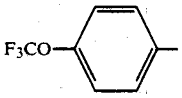 | 0 | $C_2H_5$ | $-CH_3$ | $-CH_3$ |
| 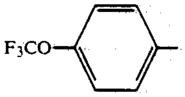 | 1 | $-C_2H_5$ | $-CH_3$ | $-CH_3$ |
| 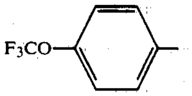 | 0 | $-CH_2CH_2CH_3$ | $-CH_3$ | $-CH_3$ |
| 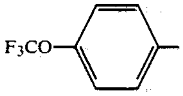 | 1 | $-CH_2CH_2CH_3$ | $-CH_3$ | $-CH_3$ |
| 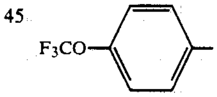 | 0 | $-CH(CH_3)_2$ | $-CH_3$ | $-CH_3$ |
| 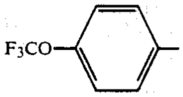 | 1 | $-CH(CH_3)_2$ | $-CH_3$ | $-CH_3$ |
| 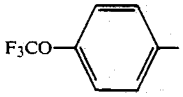 | 0 | 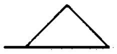 | $-CH_3$ | $-CH_3$ |
| 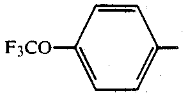 | 1 | 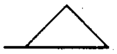 | $-CH_3$ | $-CH_3$ |
| 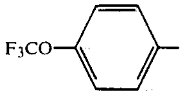 | 0 | $-CH_2CH=CH_2$ | $-CH_3$ | $-CH_3$ |

TABLE 3-continued

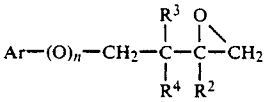

| Ar | n | $R^2$ | $R^3$ | $R^4$ |
|---|---|---|---|---|
| 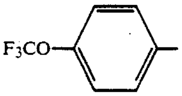 | 1 | $-CH_2CH{=}CH_2$ | $-CH_3$ | $-CH_3$ |
| 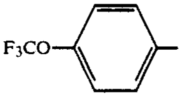 | 0 | $-(CH_2)_3-CH_3$ | $-CH_3$ | $-CH_3$ |
| 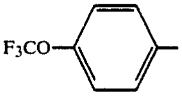 | 1 | $-(CH_2)_3-CH_3$ | $-CH_3$ | $-CH_3$ |
| 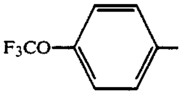 | 0 | $-CH_2CH(CH_3)_2$ | $-CH_3$ | $-CH_3$ |
| 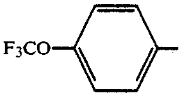 | 1 | $-CH_2CH(CH_3)_2$ | $-CH_3$ | $-CH_3$ |
| 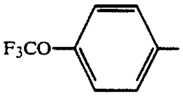 | 0 | $-(CH_2)_4-CH_3$ | $-CH_3$ | $-CH_3$ |
| 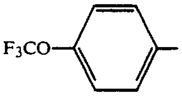 | 1 | $-(CH_2)_4-CH_3$ | $-CH_3$ | $-CH_3$ |
| 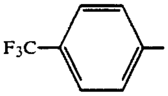 | 0 | $-CH_3$ | $-CH_3$ | $-CH_3$ |
| 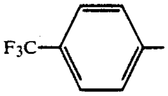 | 1 | $-CH_3$ | $-CH_3$ | $-CH_3$ |
| 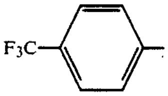 | 0 | $-C_2H_5$ | $-CH_3$ | $-CH_3$ |
| 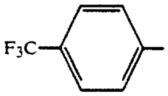 | 1 | $-C_2H_5$ | $-CH_3$ | $-CH_3$ |
| 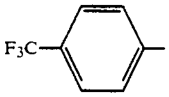 | 0 | $-CH_2CH_2CH_3$ | $-CH_3$ | $-CH_3$ |

TABLE 3-continued

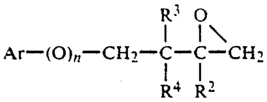

| Ar | n | $R^2$ | $R^3$ | $R^4$ |
|---|---|---|---|---|
| 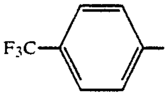 | 1 | $-CH_2CH_2CH_3$ | $-CH_3$ | $-CH_3$ |
| 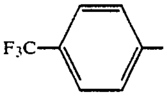 | 0 | $-CH(CH_3)_2$ | $-CH_3$ | $-CH_3$ |
| 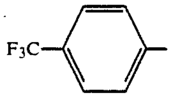 | 1 | $-CH(CH_3)_2$ | $-CH_3$ | $-CH_3$ |
| 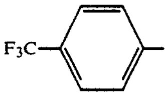 | 0 | 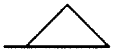 | $-CH_3$ | $-CH_3$ |
| 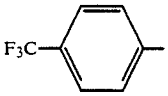 | 1 | 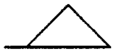 | $-CH_3$ | $-CH_3$ |
| 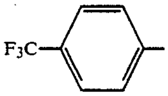 | 0 | $-CH_2CH{=}CH_2$ | $-CH_3$ | $-CH_3$ |
| 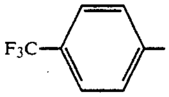 | 1 | $-CH_2CH{=}CH_2$ | $-CH_3$ | $-CH_3$ |
| 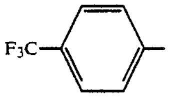 | 0 | $-(CH_2)_3-CH_3$ | $-CH_3$ | $-CH_3$ |
| 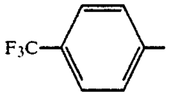 | 1 | $-(CH_2)_3-CH_3$ | $-CH_3$ | $-CH_3$ |
| 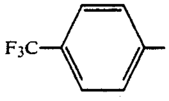 | 0 | $-CH_2CH(CH_3)_2$ | $-CH_3$ | $-CH_3$ |
| 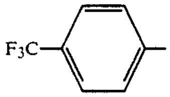 | 1 | $-CH_2CH(CH_3)_2$ | $-CH_3$ | $-CH_3$ |
| 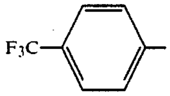 | 0 | $-(CH_2)_4-CH_3$ | $-CH_3$ | $-CH_3$ |

TABLE 3-continued

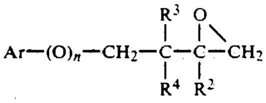

| Ar | n | $R^2$ | $R^3$ | $R^4$ |
|---|---|---|---|---|
| 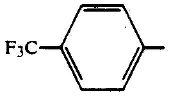 | 1 | $-(CH_2)_4-CH_3$ | $-CH_3$ | $-CH_3$ |
| 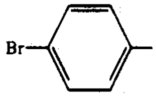 | 0 | $-CH_3$ | $-CH_3$ | $-CH_3$ |
| 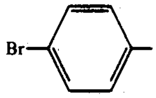 | 1 | $-CH_3$ | $-CH_3$ | $-CH_3$ |
| 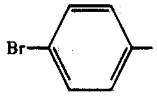 | 0 | $-C_2H_5$ | $-CH_3$ | $-CH_3$ |
| 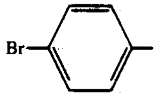 | 1 | $-C_2H_5$ | $-CH_3$ | $-CH_3$ |
| 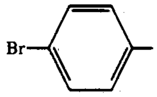 | 0 | $-CH_2CH_2CH_3$ | $-CH_3$ | $-CH_3$ |
| 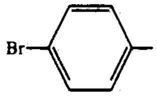 | 1 | $-CH_2CH_2CH_3$ | $-CH_3$ | $-CH_3$ |
| 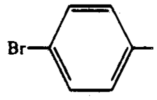 | 0 | $-CH(CH_3)_2$ | $-CH_3$ | $-CH_3$ |
| 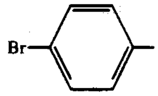 | 1 | $-CH(CH_3)_2$ | $-CH_3$ | $-CH_3$ |
| 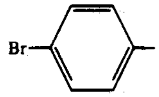 | 0 | 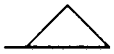 | $-CH_3$ | $-CH_3$ |
| 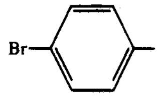 | 1 | 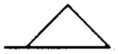 | $-CH_3$ | $-CH_3$ |
| 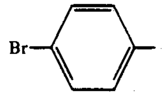 | 0 | $-CH_2CH=CH_2$ | $-CH_3$ | $-CH_3$ |

TABLE 3-continued

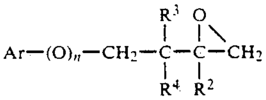

| Ar | n | $R^2$ | $R^3$ | $R^4$ |
|---|---|---|---|---|
| 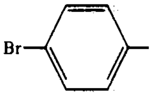 | 1 | $-CH_2CH=CH_2$ | $-CH_3$ | $-CH_3$ |
| 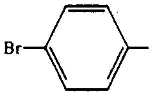 | 0 | $-(CH_2)_3-CH_3$ | $-CH_3$ | $-CH_3$ |
| 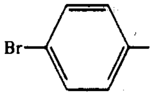 | 1 | $-(CH_2)_3-CH_3$ | $-CH_3$ | $-CH_3$ |
| 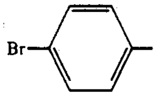 | 0 | $-CH_2CH(CH_3)_2$ | $-CH_3$ | $-CH_3$ |
| 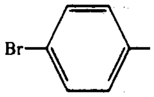 | 1 | $-CH_2CH(CH_3)_2$ | $-CH_3$ | $-CH_3$ |
| 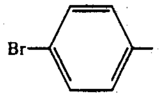 | 0 | $-(CH_2)_4-CH_3$ | $-CH_3$ | $-CH_3$ |
| 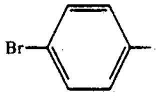 | 1 | $-(CH_2)_4-CH_3$ | $-CH_3$ | $-CH_3$ |
| 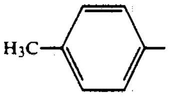 | 0 | $-CH_3$ | $-CH_3$ | $-CH_3$ |
| 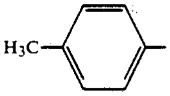 | 1 | $-CH_3$ | $-CH_3$ | $-CH_3$ |
| 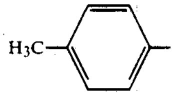 | 0 | $-C_2H_5$ | $-CH_3$ | $-CH_3$ |
| 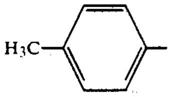 | 1 | $-C_2H_5$ | $-CH_3$ | $-CH_3$ |
| 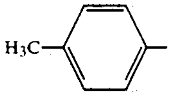 | 0 | $-CH_2CH_2CH_3$ | $-CH_3$ | $-CH_3$ |

TABLE 3-continued

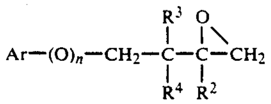

| Ar | n | $R^2$ | $R^3$ | $R^4$ |
|---|---|---|---|---|
| 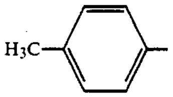 | 1 | $-CH_2CH_2CH_3$ | $-CH_3$ | $-CH_3$ |
| 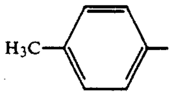 | 0 | $-CH(CH_3)_2$ | $-CH_3$ | $-CH_3$ |
| 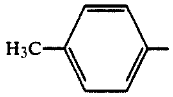 | 1 | $-CH(CH_3)_2$ | $-CH_3$ | $-CH_3$ |
| 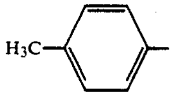 | 0 | 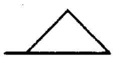 | $-CH_3$ | $-CH_3$ |
| 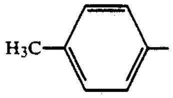 | 1 | 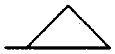 | $-CH_3$ | $-CH_3$ |
| 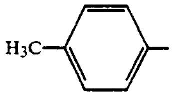 | 0 | $-CH_2CH=CH_2$ | $-CH_3$ | $-CH_3$ |
| 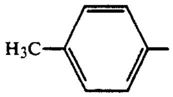 | 1 | $-CH_2CH=CH_2$ | $-CH_3$ | $-CH_3$ |
| 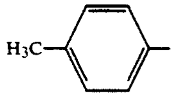 | 0 | $-(CH_2)_3-CH_3$ | $-CH_3$ | $-CH_3$ |
| 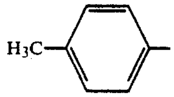 | 1 | $-(CH_2)_3-CH_3$ | $-CH_3$ | $-CH_3$ |
| 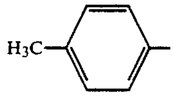 | 0 | $-CH_2CH(CH_3)_2$ | $-CH_3$ | $-CH_3$ |
| 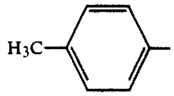 | 1 | $-CH_2CH(CH_3)_2$ | $-CH_3$ | $-CH_3$ |
| 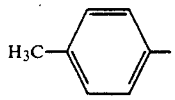 | 0 | $-(CH_2)_4-CH_3$ | $-CH_3$ | $-CH_3$ |

TABLE 3-continued

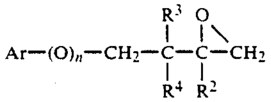

| Ar | n | $R^2$ | $R^3$ | $R^4$ |
|---|---|---|---|---|
| 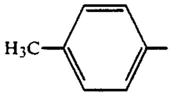 | 1 | $-(CH_2)_4-CH_3$ | $-CH_3$ | $-CH_3$ |
| 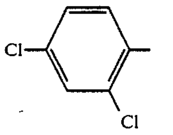 | 0 | $-CH_3$ | $-CH_3$ | $-CH_3$ |
| 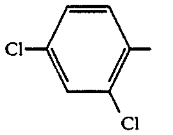 | 1 | $-CH_3$ | $-CH_3$ | $-CH_3$ |
| 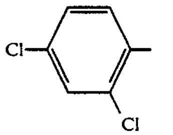 | 0 | $-C_2H_5$ | $-CH_3$ | $-CH_3$ |
| 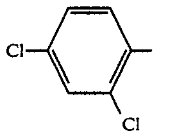 | 1 | $-C_2H_5$ | $-CH_3$ | $-CH_3$ |
| 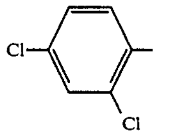 | 0 | $-CH_2CH_2CH_3$ | $-CH_3$ | $-CH_3$ |
| 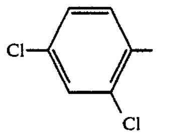 | 1 | $-CH_2CH_2CH_3$ | $-CH_3$ | $-CH_3$ |
| 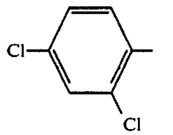 | 0 | $-CH(CH_3)_2$ | $-CH_3$ | $-CH_3$ |
| 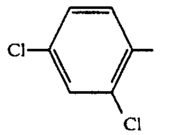 | 1 | $-CH(CH_3)_2$ | $-CH_3$ | $-CH_3$ |
| 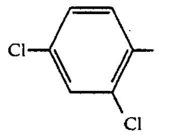 | 0 | 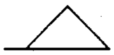 | $-CH_3$ | $-CH_3$ |

TABLE 3-continued

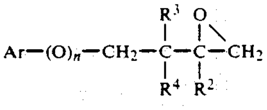

| Ar | n | $R^2$ | $R^3$ | $R^4$ |
|---|---|---|---|---|
| 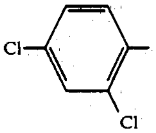 | 1 | 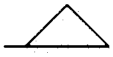 | $-CH_3$ | $-CH_3$ |
| 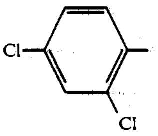 | 0 | $-CH_2CH{=}CH_2$ | $-CH_3$ | $-CH_3$ |
| 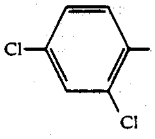 | 1 | $-CH_2CH{=}CH_2$ | $-CH_3$ | $-CH_3$ |
| 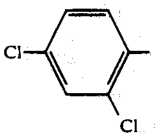 | 0 | $-(CH_2)_3-CH_3$ | $-CH_3$ | $-CH_3$ |
| 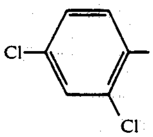 | 1 | $-(CH_2)_3-CH_3$ | $-CH_3$ | $-CH_3$ |
| 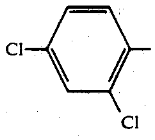 | 0 | $-CH_2CH(CH_3)_2$ | $-CH_3$ | $-CH_3$ |
| 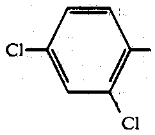 | 1 | $-CH_2CH(CH_3)_2$ | $-CH_3$ | $-CH_3$ |
| 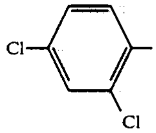 | 0 | $-(CH_2)_4-CH_3$ | $-CH_3$ | $-CH_3$ |
| 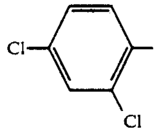 | 1 | $-(CH_2)_4-CH_3$ | $-CH_3$ | $-CH_3$ |

TABLE 3-continued

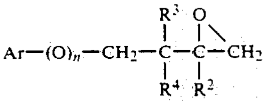

| Ar | n | $R^2$ | $R^3$ | $R^4$ |
|---|---|---|---|---|
| 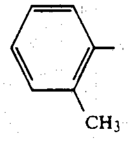 | 0 | $-CH_3$ | $-CH_3$ | $-CH_3$ |
| 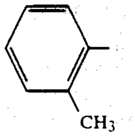 | 1 | $-CH_3$ | $-CH_3$ | $-CH_3$ |
| 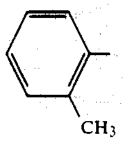 | 0 | $-C_2H_5$ | $-CH_3$ | $-CH_3$ |
| 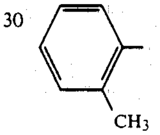 | 1 | $-C_2H_5$ | $-CH_3$ | $-CH_3$ |
| 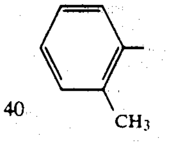 | 0 | $-CH_2CH_2CH_3$ | $-CH_3$ | $-CH_3$ |
| 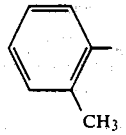 | 1 | $-CH_2CH_2CH_3$ | $-CH_3$ | $-CH_3$ |
| 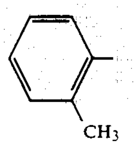 | 0 | $-CH(CH_3)_2$ | $-CH_3$ | $-CH_3$ |
| 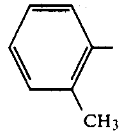 | 1 | $-CH(CH_3)_2$ | $-CH_3$ | $-CH_3$ |
| 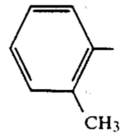 | 0 | 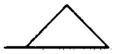 | $-CH_3$ | $-CH_3$ |

TABLE 3-continued

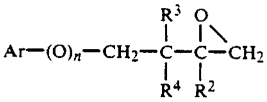

| Ar | n | $R^2$ | $R^3$ | $R^4$ |
|---|---|---|---|---|
| 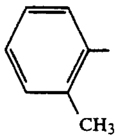 | 1 | 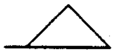 | $-CH_3$ | $-CH_3$ |
| 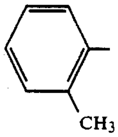 | 0 | $-CH_2CH{=}CH_2$ | $-CH_3$ | $-CH_3$ |
| 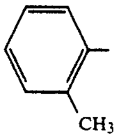 | 1 | $-CH_2CH{=}CH_2$ | $-CH_3$ | $-CH_3$ |
| 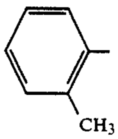 | 0 | $-(CH_2)_3-CH_3$ | $-CH_3$ | $-CH_3$ |
| 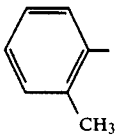 | 1 | $-(CH_2)_3-CH_3$ | $-CH_3$ | $-CH_3$ |
| 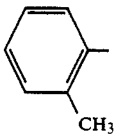 | 0 | $-CH_2CH(CH_3)_2$ | $-CH_3$ | $-CH_3$ |
| 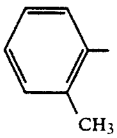 | 1 | $-CH_2CH(CH_3)_2$ | $-CH_3$ | $-CH_3$ |
| 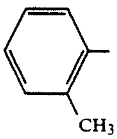 | 0 | $-(CH_2)_4-CH_3$ | $-CH_3$ | $-CH_3$ |
| 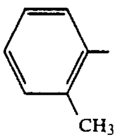 | 1 | $-(CH_2)_4-CH_3$ | $-CH_3$ | $-CH_3$ |

TABLE 3-continued

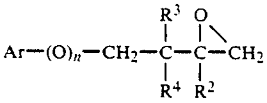

| Ar | n | $R^2$ | $R^3$ | $R^4$ |
|---|---|---|---|---|
| 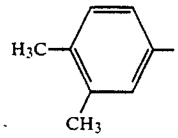 | 0 | $-CH_3$ | $-CH_3$ | $-CH_3$ |
| 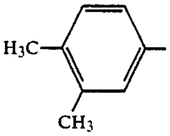 | 1 | $-CH_3$ | $-CH_3$ | $-CH_3$ |
| 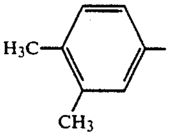 | 0 | $-C_2H_5$ | $-CH_3$ | $-CH_3$ |
| 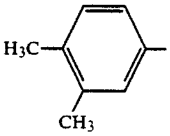 | 1 | $-C_2H_5$ | $-CH_3$ | $-CH_3$ |
| 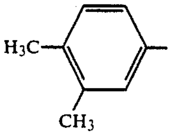 | 0 | $-CH_2CH_2CH_3$ | $-CH_3$ | $-CH_3$ |
| 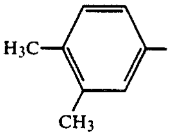 | 1 | $-CH_2CH_2CH_3$ | $-CH_3$ | $-CH_3$ |
| 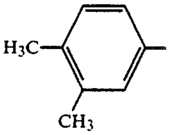 | 0 | $-CH(CH_3)_2$ | $-CH_3$ | $-CH_3$ |
| 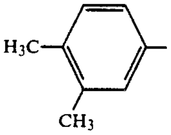 | 1 | $-CH(CH_3)_2$ | $-CH_3$ | $-CH_3$ |
| 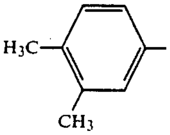 | 0 | 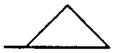 | $-CH_3$ | $-CH_3$ |

TABLE 3-continued

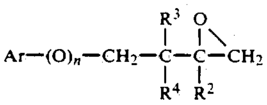

| Ar | n | $R^2$ | $R^3$ | $R^4$ |
|---|---|---|---|---|
| 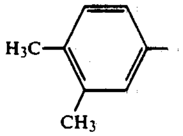 | 1 | 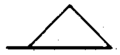 | $-CH_3$ | $-CH_3$ |
| 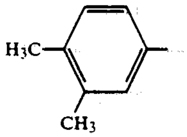 | 0 | $-CH_2CH{=}CH_2$ | $-CH_3$ | $-CH_3$ |
| 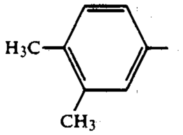 | 1 | $-CH_2CH{=}CH_2$ | $-CH_3$ | $-CH_3$ |
| 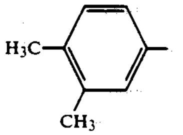 | 0 | $-(CH_2)_3-CH_3$ | $-CH_3$ | $-CH_3$ |
| 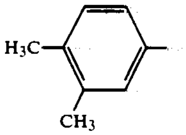 | 1 | $-(CH_2)_3-CH_3$ | $-CH_3$ | $-CH_3$ |
| 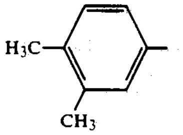 | 0 | $-CH_2CH(CH_3)_2$ | $-CH_3$ | $-CH_3$ |
| 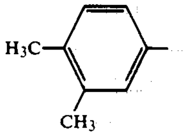 | 1 | $-CH_2CH(CH_3)_2$ | $-CH_3$ | $-CH_3$ |
| 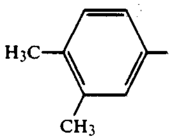 | 0 | $-(CH_2)_4-CH_3$ | $-CH_3$ | $-CH_3$ |
| 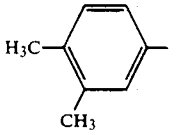 | 1 | $-(CH_2)_4-CH_3$ | $-CH_3$ | $-CH_3$ |

TABLE 3-continued

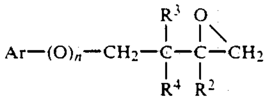

| Ar | n | $R^2$ | $R^3$ | $R^4$ |
|---|---|---|---|---|
| 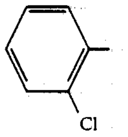 | 0 | $-CH_3$ | $-CH_3$ | $-CH_3$ |
| 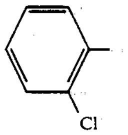 | 1 | $-CH_3$ | $-CH_3$ | $-CH_3$ |
| 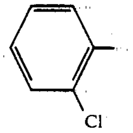 | 0 | $-C_2H_5$ | $-CH_3$ | $-CH_3$ |
| 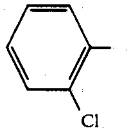 | 1 | $-C_2H_5$ | $-CH_3$ | $-CH_3$ |
| 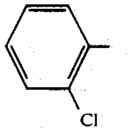 | 0 | $-CH_2CH_2CH_3$ | $-CH_3$ | $-CH_3$ |
| 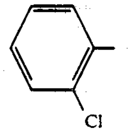 | 1 | $-CH_2CH_2CH_3$ | $-CH_3$ | $-CH_3$ |
| 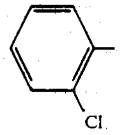 | 0 | $-CH(CH_3)_2$ | $-CH_3$ | $-CH_3$ |
| 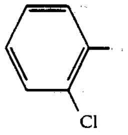 | 1 | $-CH(CH_3)_2$ | $-CH_3$ | $-CH_3$ |
| 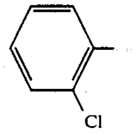 | 0 | 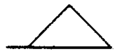 | $-CH_3$ | $-CH_3$ |

TABLE 3-continued

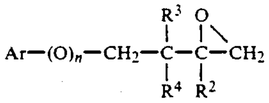

| Ar | n | $R^2$ | $R^3$ | $R^4$ |
|---|---|---|---|---|
| 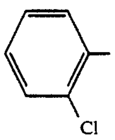 | 1 | 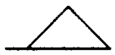 | $-CH_3$ | $-CH_3$ |
| 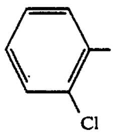 | 0 | $-CH_2CH{=}CH_2$ | $-CH_3$ | $-CH_3$ |
| 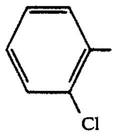 | 1 | $-CH_2CH{=}CH_2$ | $-CH_3$ | $-CH_3$ |
| 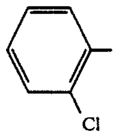 | 0 | $-(CH_2)_3-CH_3$ | $-CH_3$ | $-CH_3$ |
| 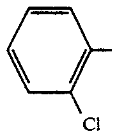 | 1 | $-(CH_2)_3-CH_3$ | $-CH_3$ | $-CH_3$ |
| 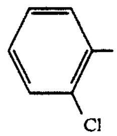 | 0 | $-CH_2CH(CH_3)_2$ | $-CH_3$ | $-CH_3$ |
| 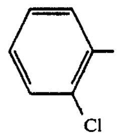 | 1 | $-CH_2CH(CH_3)_2$ | $-CH_3$ | $-CH_3$ |
| 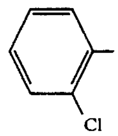 | 0 | $-(CH_2)_4-CH_3$ | $-CH_3$ | $-CH_3$ |
| 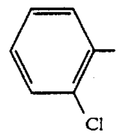 | 1 | $-(CH_2)_4-CH_3$ | $-CH_3$ | $-CH_3$ |

TABLE 3-continued

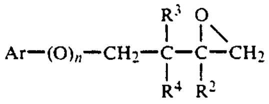

| Ar | n | $R^2$ | $R^3$ | $R^4$ |
|---|---|---|---|---|
| 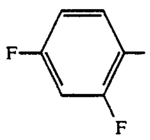 | 0 | $-CH_3$ | $-CH_3$ | $-CH_3$ |
| 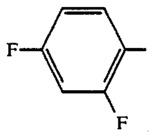 | 1 | $-CH_3$ | $-CH_3$ | $-CH_3$ |
| 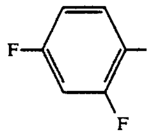 | 0 | $-C_2H_5$ | $-CH_3$ | $-CH_3$ |
| 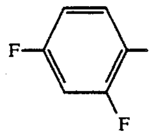 | 1 | $-C_2H_5$ | $-CH_3$ | $-CH_3$ |
| 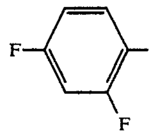 | 0 | $-CH_2CH_2CH_3$ | $-CH_3$ | $-CH_3$ |
| 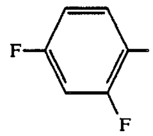 | 1 | $-CH_2CH_2CH_3$ | $-CH_3$ | $-CH_3$ |
| 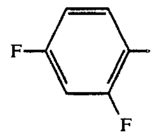 | 0 | $-CH(CH_3)_2$ | $-CH_3$ | $-CH_3$ |
| 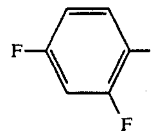 | 1 | $-CH(CH_3)_2$ | $-CH_3$ | $-CH_3$ |
| 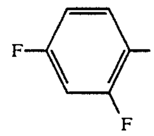 | 0 | 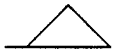 | $-CH_3$ | $-CH_3$ |

TABLE 3-continued

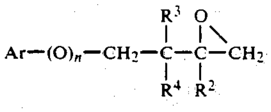

| Ar | n | $R^2$ | $R^3$ | $R^4$ |
|---|---|---|---|---|
| 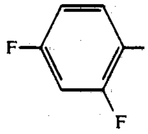 | 1 | 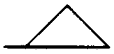 | $-CH_3$ | $-CH_3$ |
| 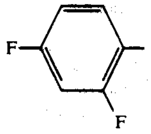 | 0 | $-CH_2CH{=}CH_2$ | $-CH_3$ | $-CH_3$ |
| 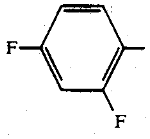 | 1 | $-CH_2CH{=}CH_2$ | $-CH_3$ | $-CH_3$ |
| 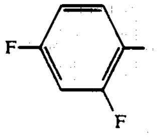 | 0 | $-(CH_2)_3-CH_3$ | $-CH_3$ | $-CH_3$ |
| 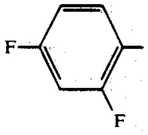 | 1 | $-(CH_2)_3-CH_3$ | $-CH_3$ | $-CH_3$ |
| 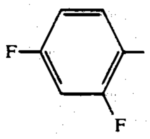 | 0 | $-CH_2CH(CH_3)_2$ | $-CH_3$ | $-CH_3$ |
| 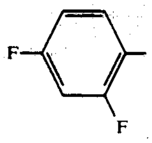 | 1 | $-CH_2CH(CH_3)_2$ | $-CH_3$ | $-CH_3$ |
| 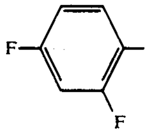 | 0 | $-(CH_2)_4-CH_3$ | $-CH_3$ | $-CH_3$ |
| 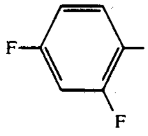 | 1 | $-(CH_2)_4-CH_3$ | $-CH_3$ | $-CH_3$ |

TABLE 3-continued

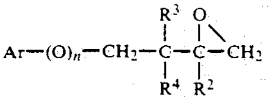

| Ar | n | $R^2$ | $R^3$ | $R^4$ |
|---|---|---|---|---|
| 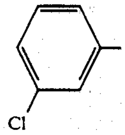 | 0 | $-CH_3$ | $-CH_3$ | $-CH_3$ |
| 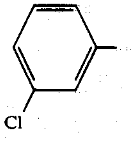 | 1 | $-CH_3$ | $-CH_3$ | $-CH_3$ |
| 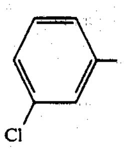 | 0 | $-C_2H_5$ | $-CH_3$ | $-CH_3$ |
| 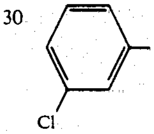 | 1 | $-C_2H_5$ | $-CH_3$ | $-CH_3$ |
| 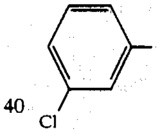 | 0 | $-CH_2CH_2CH_3$ | $-CH_3$ | $-CH_3$ |
| 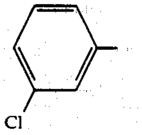 | 1 | $-CH_2CH_2CH_3$ | $-CH_3$ | $-CH_3$ |
| 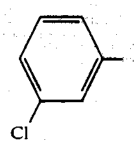 | 0 | $-CH(CH_3)_2$ | $-CH_3$ | $-CH_3$ |
| 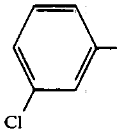 | 1 | $-CH(CH_3)_2$ | $-CH_3$ | $-CH_3$ |
| 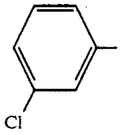 | 0 | 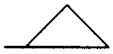 | $-CH_3$ | $-CH_3$ |

TABLE 3-continued

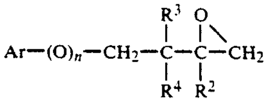

| Ar | n | $R^2$ | $R^3$ | $R^4$ |
|---|---|---|---|---|
| 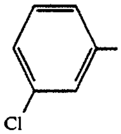 | 1 | 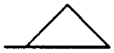 | $-CH_3$ | $-CH_3$ |
| 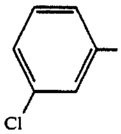 | 0 | $-CH_2CH{=}CH_2$ | $-CH_3$ | $-CH_3$ |
| 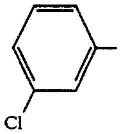 | 1 | $-CH_2CH{=}CH_2$ | $-CH_3$ | $-CH_3$ |
| 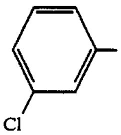 | 0 | $-(CH_2)_3-CH_3$ | $-CH_3$ | $-CH_3$ |
| 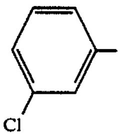 | 1 | $-(CH_2)_3-CH_3$ | $-CH_3$ | $-CH_3$ |
| 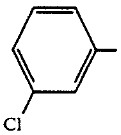 | 0 | $-CH_2CH(CH_3)_2$ | $-CH_3$ | $-CH_3$ |
| 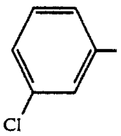 | 1 | $-CH_2CH(CH_3)_2$ | $-CH_3$ | $-CH_3$ |
| 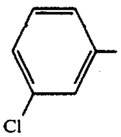 | 0 | $-(CH_2)_4-CH_3$ | $-CH_3$ | $-CH_3$ |
| 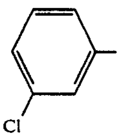 | 1 | $-(CH_2)_4-CH_3$ | $-CH_3$ | $-CH_3$ |
| 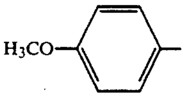 | 0 | $-CH_3$ | $-CH_3$ | $-CH_3$ |

TABLE 3-continued

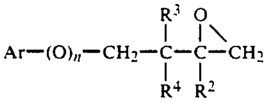

| Ar | n | $R^2$ | $R^3$ | $R^4$ |
|---|---|---|---|---|
| 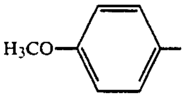 | 1 | $-CH_3$ | $-CH_3$ | $-CH_3$ |
| 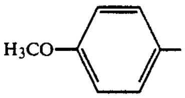 | 0 | $-C_2H_5$ | $-CH_3$ | $-CH_3$ |
| 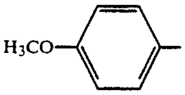 | 1 | $-C_2H_5$ | $-CH_3$ | $-CH_3$ |
| 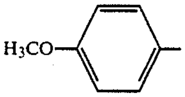 | 0 | $-CH_2CH_2CH_3$ | $-CH_3$ | $-CH_3$ |
| 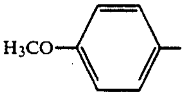 | 1 | $-CH_2CH_2CH_3$ | $-CH_3$ | $-CH_3$ |
| 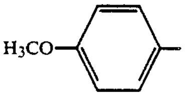 | 0 | $-CH(CH_3)_2$ | $-CH_3$ | $-CH_3$ |
| 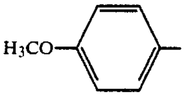 | 1 | $-CH(CH_3)_2$ | $-CH_3$ | $-CH_3$ |
| 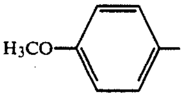 | 0 | 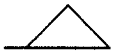 | $-CH_3$ | $-CH_3$ |
| 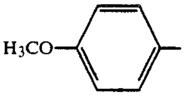 | 1 | 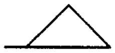 | $-CH_3$ | $-CH_3$ |
| 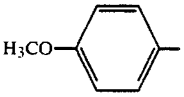 | 0 | $-CH_2CH{=}CH_2$ | $-CH_3$ | $-CH_3$ |
| 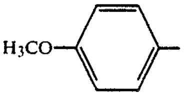 | 1 | $-CH_2CH{=}CH_2$ | $-CH_3$ | $-CH_3$ |
| 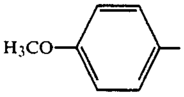 | 0 | $-(CH_2)_3-CH_3$ | $-CH_3$ | $-CH_3$ |

TABLE 3-continued

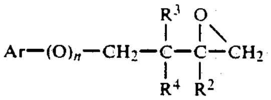

| Ar | n | $R^2$ | $R^3$ | $R^4$ |
|---|---|---|---|---|
| 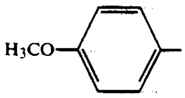 | 1 | $-(CH_2)_3-CH_3$ | $-CH_3$ | $-CH_3$ |
| 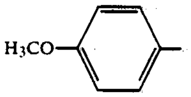 | 0 | $-CH_2CH(CH_3)_2$ | $-CH_3$ | $-CH_3$ |
| 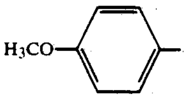 | 1 | $-CH_2CH(CH_3)_2$ | $-CH_3$ | $-CH_3$ |
| 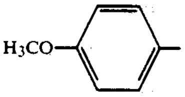 | 0 | $-(CH_2)_4-CH_3$ | $-CH_3$ | $-CH_3$ |
| 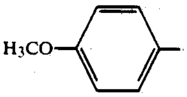 | 1 | $-(CH_2)_4-CH_3$ | $-CH_3$ | $-CH_3$ |
| 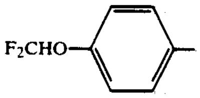 | 0 | $-CH_3$ | $-CH_3$ | $-CH_3$ |
| 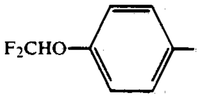 | 1 | $-CH_3$ | $-CH_3$ | $-CH_3$ |
| 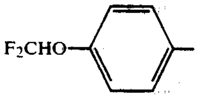 | 0 | $-C_2H_5$ | $-CH_3$ | $-CH_3$ |
| 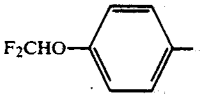 | 1 | $-C_2H_5$ | $-CH_3$ | $-CH_3$ |
| 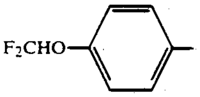 | 0 | $-CH_2CH_2CH_3$ | $-CH_3$ | $-CH_3$ |
| 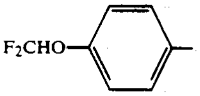 | 1 | $-CH_2CH_2CH_3$ | $-CH_3$ | $-CH_3$ |
| 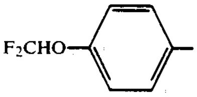 | 0 | $-CH(CH_3)_2$ | $-CH_3$ | $-CH_3$ |

TABLE 3-continued

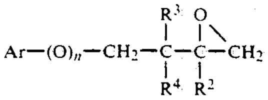

| Ar | n | $R^2$ | $R^3$ | $R^4$ |
|---|---|---|---|---|
| 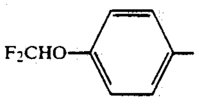 | 1 | $-CH(CH_3)_2$ | $-CH_3$ | $-CH_3$ |
| 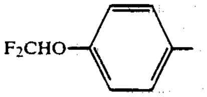 | 0 | 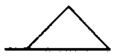 | $-CH_3$ | $-CH_3$ |
| 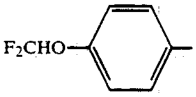 | 1 | 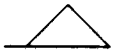 | $-CH_3$ | $-CH_3$ |
| 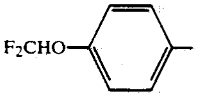 | 0 | $-CH_2CH=CH_2$ | $-CH_3$ | $-CH_3$ |
| 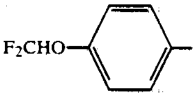 | 1 | $-CH_2CH=CH_2$ | $-CH_3$ | $-CH_3$ |
| 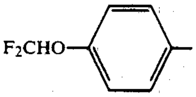 | 0 | $-(CH_2)_3-CH_3$ | $-CH_3$ | $-CH_3$ |
| 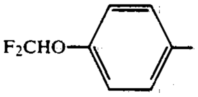 | 1 | $-(CH_2)_3-CH_3$ | $-CH_3$ | $-CH_3$ |
| 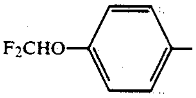 | 0 | $-CH_2CH(CH_3)_2$ | $-CH_3$ | $-CH_3$ |
| 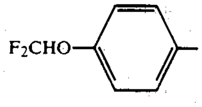 | 1 | $-CH_2CH(CH_3)_2$ | $-CH_3$ | $-CH_3$ |
| 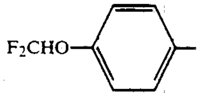 | 0 | $-(CH_2)_4-CH_3$ | $-CH_3$ | $-CH_3$ |
| 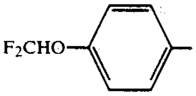 | 1 | $-(CH_2)_4-CH_3$ | $-CH_3$ | $-CH_3$ |

The oxiranes of the formula (V) were hitherto unknown. They can be prepared by a process in which (c) ketones of the formula

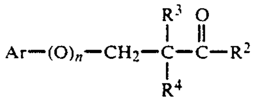

(VII)

in which n, Ar, $R^2$, $R^3$ and $R^4$ have the abovementioned meanings, are reacted either (α) with dimethyloxosulphonium methylide of the formula $$\delta+\delta-(CH_3)_2SOCH_2 \quad (VIII)$$

in the presence of a diluent, such as, for example, dimethyl sulphoxide, at temperatures between 20° C. and 80° C., or (β) with trimethylsulphonium methylsulphate of the formula $$[(CH_3)_3S^{61}]CH_3SO_4^{\ominus} \quad (IX)$$

in the presence of an inert organic solvent, such as, for example, acetonitrile, and in the presence of a base, such as, for example, sodium methoxide, at temperatures between 0° C. to 60° C., preferably at room temperature, or (γ) with methyl-triphenylphosphonium bromide of the formula $$H_3C-P^{\oplus}(C_6H_5)_3\ Br^{\ominus} \quad (X)$$

presence of a base, such as, for example, potassium tert-butoxide and if appropriate in the presence of a diluent, such as, for example, diethyl ether, benzene or toluene, at temperatures between 20° C. and 150° C. (cf. in this context Syn. Comm. 1985, 15, 855) and the resulting alkenes of the formula

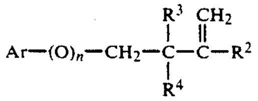

(XI)

in which n, Ar, $R^2$, $R^3$ and R4 have the abovementioned meanings, are reacted with oxygenating agents, such as, for example, m-chloroperbenzoic acid, performic acid or peracetic acid (or hydrogen peroxide as a mixture with formic acid or acetic acid), in the presence of a diluent, such as, for example, methylene chloride or chloroform, at temperatures between 0° C. and 100° C.

Formula (VII) provides a general definition of the ketones to be used as intermediates.

In formula (VII), n, Ar, $R^2$, $R^3$ and $R^4$ preferably, or in particular, have those meanings which have already been preferably mentioned above, or mentioned above as particularly preferred, for n, Ar, $R^2$, $R^3$ and $R^4$ in connection with the description of the compounds of the formula (I) according to the invention.

The ketones of the formula (VII), in which $R^2$ stands for methyl, have already been disclosed (cf. DE-OS (German Published Specification) No. 3,021,516). The ketones of the formula

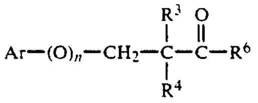

(VII-a)

in which

Ar stands for optionally substituted phenyl or for optionally substituted naphthyl, n stands for the numbers 0 or 1, $R^3$ stands for methyl, $R^4$ stands for methyl or $R^3$ and $R^4$ together stand for ethane-1,2-diyl and $R^6$ stands for alkyl having more than one carbon atom, cycloalkyl, cycloalkylalkyl or alkenyl, were hitherto unknown.

The ketones of the formula (VII-a) can be prepared by a process in which (d) compounds of the formula

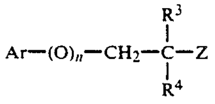

(XII)

in which n, Ar, $R^3$ and $R^4$ have the abovementioned meanings and

Z stands for cyano, chlorocarbonyl, methoxycarbonyl or ethoxycarbonyl, are reacted with Grignard compounds of the formula $$R^6\text{-}MgBr \quad (XIII)$$

in which $R^6$ has the abovementioned meaning, if appropriate in the presence of a diluent, such as, for example, diethyl ether, tetrahydrofuran or toluene, or mixtures of these substances, at temperatures between 0° C. and 110° C.

The ketones of the formula (VII-a), in which $R^3$ and $R^4$ in each case stand for methyl, can be prepared by a process in which (e) isopropyl ketones of the formula $$(CH_3)_2CH—CO—R^6 \quad (XIV)$$

in which $R^6$ has the abovementioned meaning, are reacted with compounds of the formula $$Ar—(O)_n—CH_2—X^1 \quad (XV)$$

in which n and Ar have the abovementioned meanings and $X^1$ stands for chlorine, bromine and iodine, if appropriate in the presence of an acid acceptor, such as, for example, potassium hydroxide, if appropriate in the presence of a phase-transfer catalyst, such as, for example, tetrabutylammonium bromide, and if appropriate in the presence of a diluent, such as, for example, toluene, at temperatures between 0° C. and 100° C.

The ketones of the formula (VII-a), in which n stands for 1 and $R^3$ and $R^4$ stand for methyl, can be prepared by a process in which (f) isopropyl ketones of the formula $$(CH_3)_2CH—CO—R^6 \quad (XIV)$$

in which

R6 has the abovementioned meaning, are reacted with formaldehyde or an oligomeric form thereof, such as for example, paraformaldehyde, if appropriate in the presence of a base, such as, for example, potassium hydroxide, and if appropriate in the presence of a diluent, such as, for example, methanol, at temperatures between 0° C. and 80° C., the resulting hydroxymethyl compounds of the formula

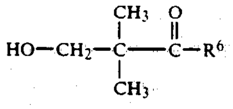 (XVI)

in which $R^6$ has the abovementioned meaning, are reacted with a sulphonyl chloride of the formula $R^7-SO_2-Cl$ (XVII)

in which $R^7$ stands for methyl or 4-methyl-phenyl, if appropriate in the presence of an acid-binding agent, such as, for example, pyridine, and if appropriate in the presence of a diluent, such as, for example, chloroform, at temperatures between 0° C. and 50° C., and the resulting sulphonyloxy compounds of the formula

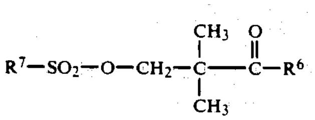 (XVIII)

in which $R^6$ and $R^7$ have the abovementioned meaning, are reacted with hydroxyaryl compounds of the formula Ar—OH (XIX)

in which

Ar has the abovementioned meaning, if appropriate in the presence of bases, such as, for example, sodium methoxide, and if appropriate in the presence of diluents, such as, for example, ethylene glycol, at temperatures between 0° C. and 150° C.

The ketones of the formula (VII-a), in which $R^3$ and $R^4$ together stand for ethane-1,2-diyl, can also be prepared by a process in which (g) enones of the formula

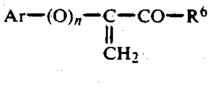 (XX)

in which n, Ar and $R^6$ have the abovementioned meanings, are reacted with dimethyloxosulphonium methylide of the formula $\delta+\delta-(CH_3)_2SOCH_2$ (VIII)

in the presence of a diluent, such as, for example, dimethyl sulphoxide, at temperatures between 20° C. and 80° C.

The ketones of the formula (VII-a), in which $R^6$ stands for cyclopropyl, can also be prepared by a process in which (h) vinyl ketones of the formula

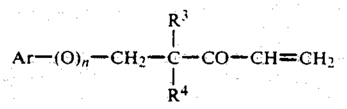 (XXI)

in which n, Ar, $R^3$ and $R^4$ have the abovementioned meanings, are reacted with dimethyloxosulphonium methylide of the formula $\delta+\delta-(CH_3)_2SOCH_2$ (VIII)

in the presence of a diluent, such as, for example, dimethyl sulphoxide, at temperatures between 20° C. and 80° C.

The compounds of the formulae (VIII), (IX), (X), (XII), (XIII), (XIV), (XV), (XIX), (XX) and (XXI) are known or can be prepared by known methods.

The ketones of the formula (VII), in which $R^2$ stands for methyl, can also be prepared by the abovementioned processes.

1,2,4-Triazole of the formula (VI), which is also required as a reactant in process (b) according to the invention, is known. It is also possible to employ it as a sodium salt or potassium salt.

Formula (IV-a) provides a general definition of the compounds furthermore required as reactants in process (b) according to the invention. In this formula, $R^5$ preferably has those meanings which have already been preferably mentioned for the radical $R^1$ in connection with the description of the substances of the formula (1) according to the invention, with the exception of hydrogen. The radical Y preferably stands for chlorine, bromine or iodine.

The compounds of the formula (IV-a) are known.

Suitable diluents for carrying out process (b) according to the invention are all inert organic solvents, and also water. Alcohols, such as ethanol and methoxyethanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; amides, such as, for example, dimethylformamide, can preferably be used.

Suitable acid acceptors or bases for carrying out process (b) according to the invention are all inorganic and organic bases which can customarily be used. These preferably include alkali metal carbonates, such as, for example, sodium carbonate and potassium carbonate; alkali metal hydroxides, such as, for example, sodium hydroxide; alkali metal alkoxides, such as, for example, sodium methoxide, sodium ethoxide, potassium methoxide and potassium ethoxide; alkali metal hydrides, such as, for example, sodium hydride; lower tertiary alkylamines, cycloalkylamines and aralkylamines, such as, in particular, triethylamine.

Suitable free-radical initiators for carrying out process (b) according to the invention are all free-radical initiators customary for reactions of this type. $\alpha,\alpha'$-Azoisobutyronitrile and dibenzoyl peroxide can preferably be used.

When carrying out process (b) according to the invention, the reaction temperatures can be varied within a relatively wide range. In general, the process is carried out at temperatures between 0° C. and 200° C., preferably at temperatures between 60° C. and 150° C.

Process (b) according to the invention is generally carried out under atmospheric pressure. However, it is also possible for the process to be carried out under increased or reduced pressure.

For carrying out process (b) according to the invention, between 1 and 2 moles, preferably between 1.1 and 1.5 moles, of 1,2,4-triazole of the formula (VI) and if appropriate between 1 and 10 moles, preferably between 1 and 8 moles, of a compound of the formula (IV-a) are generally employed per mole of oxirane of the formula (V).

In general, the reactants are mixed at room temperature and stirred, preferably at an increased temperature, until the reaction is virtually complete. Working up can be carried out by customary methods. In general, a procedure is followed in which the reaction mixture is evaporated, the residue is dissolved in methylene chloride, and the solution is washed with water, dried over sodium sulphate and filtered. The solvent is distilled off from the filtrate under a waterpump vacuum, and, if appropriate, the crude product which is obtained as a residue is purified by customary methods, for example by column chromatography.

The compounds of the formula (I) which can be obtained by the process according to the invention can be converted to acid addition salts or metal salt complexes.

Suitable acids for preparing acid addition salts of the compounds of the formula (I) are preferably those which have already been mentioned as being preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off and, if appropriate, purified by washing with an inert organic solvent.

Suitable salts for the preparation of metal salt complexes of the compounds of the formula (I) are preferably those salts of metals which have already been mentioned in connection with the description of the substances according to the invention as being preferred metal salts.

The metal salt complexes of compounds of the formula (I) can be obtained in a simple manner by customary methods, for example by dissolving the metal salt in alcohol, for example ethanol, and adding the solution to compounds of the formula (I). Metal salt complexes can be isolated in a known manner, for example by filtering off, and, if appropriate, can be purified by recrystallization.

The active compounds according to the invention exhibit a powerful microbicidal action and can be employed in practice as fungicides for combating undesired micro-organisms.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erusiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, Pyrenophora teres or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, Septoria nodorum; Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention show a very broad activity when used in vitro. However, they can also be employed with very good success in vivo protectively against for example *Botrytis cinerea* on dwarf beans, *Pyrenophora teres* on barley and *Pyricularia oryzae* on rice, and curatively for example against *Venturia inaequalis* on apples. Furthermore, they show a good action against *Erysiphe graminis, Leptosphaeria nodorum and Puccinia recondita.*

Moreover, the active compounds according to the invention also show plant growth-regulating properties. Furthermore, the active compounds according to the invention are also suitable for the protection of industrial materials, such as, for example, wood, leather, paper, textiles, from damage and destruction by microorganisms, in particular by fungi.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such, in the form of their formulations or the use forms prepared therefrom, such as ready-to-use solutions, suspensions, wettable powders, pastes, soluble powders, dusting agents and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms can be varied within a relatively wide range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The preparation and the use of the active compounds according to the invention are illustrated by the following examples.

PREPARATION EXAMPLES

Example 1

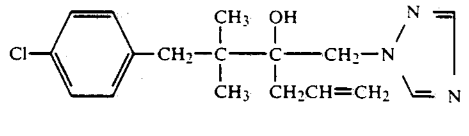

[Process (a)]

A suspension of 2.7 g (0.1 mol) of granular aluminum, one crystal of iodine and a spatula tipful of mercury(II) chloride in 20 ml of absolute tetrahydrofuran is left to stand overnight under argon. A few drops of a solution of 12.1 g (0.1 mol) of allyl bromide in 20 ml of absolute tetrahydrofuran are added, and the mixture is warmed in an ultrasonic bath (model: Bransonic 12 manufactured by Branson, Shelton; CT, USA). The reaction starts at 50° C., and the remaining amount of allyl bromide is added dropwise with stirring. The mixture is then cooled to −20° C., and a solution of 13.9 g (0.05 mol) of 4-(4-chlorophenyl)-3,3-dimethyl-1-(1,2,4-triazol-1-yl)-2-butanone in 100 ml of absolute tetrahydrofuran is added dropwise with stirring. The reaction mixture is then stirred for 1 hour at 0° C. and for 15 hours at 20° C., 100 ml of 3 N hydrochloric acid are then carefully added, and the mixture is concentrated under reduced pressure.

In the aqueous residue, a pH of 10 is adjusted using aqueous ammonia, the mixture is then diluted with water, ethyl acetate is then added, and filtration is carried out under reduced pressure. The residue remaining on the suction filter is washed with ethyl acetate, dried over sodium sulphate and concentrated. Following purification of the product by column chromatography (silica gel; methylene chloride/ethyl acetate = 1:1), 11.5 g (72% of theory) of 6-(4-chlorophenyl)-5,5-dimethyl-4-(1,2,4-triazol-1-yl-methyl)-1-hexen-4-ol of melting point 97°-98° C. are obtained.

EXAMPLE 2

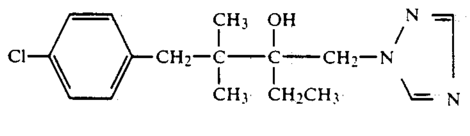

[Process (b)]

A solution of 17 g (0.07 mol) of 2-[1,1-dimethyl-2-(4-chlorophenyl)]-ethyl-2-ethyl-oxirane, 6.9 g (0.1 mol) of 1,2,4-triazole, 0.7 g (0.0175 mol) of sodium hydroxide, 0.7 ml of water and a spatula tipful of α,α'-azoisobutyronitrile in 100 ml of dimethylformamide is heated at 120° C. for 15 hours. The mixture is then cooled to room temperature and evaporated by stripping off the solvent under reduced pressure, the residue remaining is dissolved in dichloromethane, the mixture is washed twice with water, the organic phase is dried over sodium sulphate, and the solvent is removed under reduced pressure. The residue is purified by column chromatography (silica gel; dichloromethane:ethyl acetate = 1:1).

In this manner, 8.5 g (39% of theory) of 1-(4-chlorophenyl)-2,2-dimethyl-3-(1,2,4-triazol-1-yl-methyl)-pentan-3-ol of melting point 124°-125° C. are obtained.

The compounds of the formula (I) listed in Table 4 below are obtained in analogy to Examples 1 and 2 and following the general description of Preparation Processes (a) and (b) according to the invention.

TABLE 4

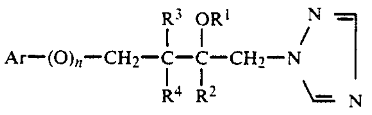

(I)

| Example No. | Ar | n | $R^1$ | $R^2$ | $R^3$ | $R^4$ | Melting point (°C.) |
|---|---|---|---|---|---|---|---|
| 3 | 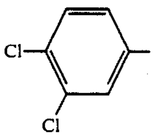 | 0 | H | $-CH_2CH{=}CH_2$ | $CH_3$ | $CH_3$ | 103 |
| 4 | 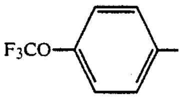 | 0 | H | $-CH_3$ | $CH_3$ | $CH_3$ | 108 |
| 5 | 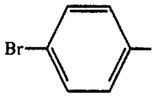 | 0 | H | $-CH_2CH_2CH_3$ | $CH_3$ | $CH_3$ | 125 |
| 6 | 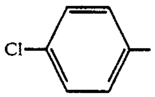 | 0 | H | $-(CH_2)_3-CH_3$ | $CH_3$ | $CH_3$ | 71 |
| 7 | 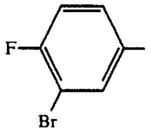 | 0 | H | $-CH_2CH{=}CH_2$ | $CH_3$ | $CH_3$ | 99 |
| 8 | 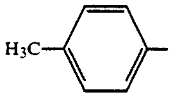 | 0 | H | $-CH_2CH{=}CH_2$ | $CH_3$ | $CH_3$ | 106 |
| 9 | 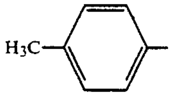 | 0 | H | $-CH_3$ | $CH_3$ | $CH_3$ | 140 |
| 10 | 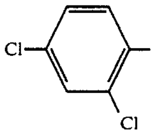 | 0 | H | $-CH_2CH{=}CH_2$ | $CH_3$ | $CH_3$ | 108 |
| 11 | 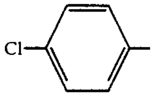 | 0 | H | $-CH(CH_3)_2$ | $CH_3$ | $CH_3$ | 130 |

TABLE 4-continued
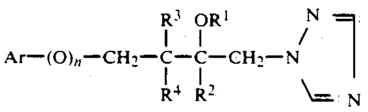
(I)
| Example No. | Ar | n | $R^1$ | $R^2$ | $R^3$ | $R^4$ | Melting point (°C.) |
|---|---|---|---|---|---|---|---|
| 12 | 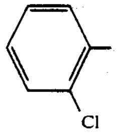 | 0 | H | $-CH_3$ | $CH_3$ | $CH_3$ | 100 |
| 13 | 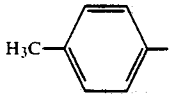 | 0 | H | 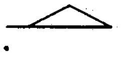 | $CH_3$ | $CH_3$ | 146 |
| 14 | 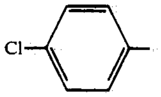 | 0 | $-CH_2CH{=}CH_2$ | $-CH_3$ | $CH_3$ | $CH_3$ | NMR* |
| 15 | 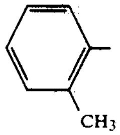 | 0 | H | $-CH_2CH{=}CH_2$ | $CH_3$ | $CH_3$ | 100 |
| 16 | 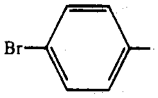 | 0 | H | $-CH_3$ | $CH_3$ | $CH_3$ | 153 |
| 17 | 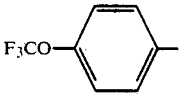 | 0 | H | $-CH_2CH{=}CH_2$ | $CH_3$ | $CH_3$ | NMR* |
| 18 | 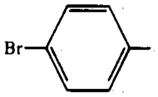 | 1 | H | $-CH_2CH{=}CH_2$ | $CH_3$ | $CH_3$ | NMR* |
| 19 | 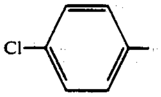 | 0 | H | $-(CH_2)_4-CH_3$ | $CH_3$ | $CH_3$ | 78 |
| 20 | 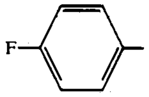 | 0 | H | $-(CH_2)_5-CH_3$ | $CH_3$ | $CH_3$ | NMR* |
| 21 | 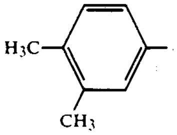 | 0 | H | $-CH_2CH{=}CH_2$ | $CH_3$ | $CH_3$ | 100 |
| 22 | 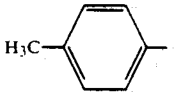 | 0 | H | $-(CH_2)_5-CH_3$ | $CH_3$ | $CH_3$ | NMR* |

TABLE 4-continued
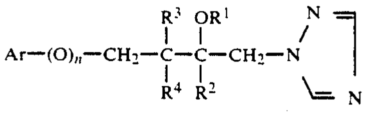
(I)
| Example No. | Ar | n | $R^1$ | $R^2$ | $R^3$ | $R^4$ | Melting point (°C.) |
|---|---|---|---|---|---|---|---|
| 23 | 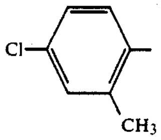 | 1 | H | $-CH_2CH{=}CH_2$ | $CH_3$ | $CH_3$ | NMR* |
| 24 | 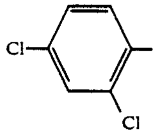 | 1 | H | $-CH_2CH{=}CH_2$ | $CH_3$ | $CH_3$ | NMR* |
| 25 | 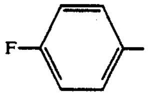 | 0 | H | $-CH_2CH_2CH_3$ | $CH_3$ | $CH_3$ | 87 |
| 26 | 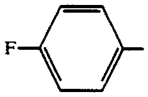 | 0 | H | $-CH(CH_3)_2$ | $CH_3$ | $CH_3$ | 93 |
| 27 | 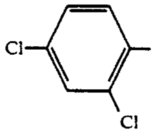 | 0 | H | $-CH_3$ | $CH_3$ | $CH_3$ | 114 |
| 28 | 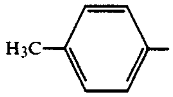 | 0 | H | $-C_2H_5$ | $CH_3$ | $CH_3$ | 120 |
| 29 | 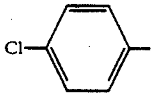 | 0 | H | $-CH_2CH_2CH_3$ | $CH_3$ | $CH_3$ | 126 |
| 30 | 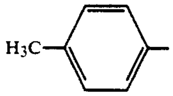 | 0 | H | $-CH(CH_3)_2$ | $CH_3$ | $CH_3$ | 109 |
| 31 | 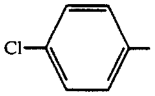 | 0 | H | $-CH_3$ | $CH_3$ | $CH_3$ | 135 |
| 32 | 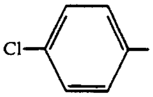 | 1 | H | $-CH_3$ | $CH_3$ | $CH_3$ | 116 |
| 33 | 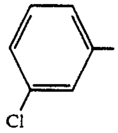 | 1 | H | $-CH_3$ | $CH_3$ | $CH_3$ | 67 |

TABLE 4-continued

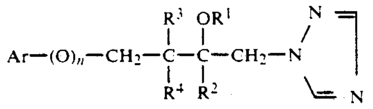

(I)

| Example No. | Ar | n | $R^1$ | $R^2$ | $R^3$ | $R^4$ | Melting point (°C.) |
|---|---|---|---|---|---|---|---|
| 34 | 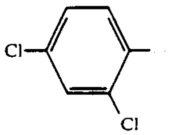 | 1 | H | $-CH(CH_3)_2$ | $CH_3$ | $CH_3$ | 84 |
| 35 | 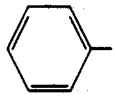 | 1 | H | $-CH(CH_3)_2$ | $CH_3$ | $CH_3$ | 104 |
| 36 | 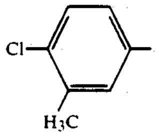 | 1 | H | $-CH(CH_3)_2-$ | $CH_3$ | $CH_3$ | 68 |
| 37 | 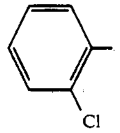 | 0 | H | $CH(CH_3)_2$ | $CH_3$ | $CH_3$ | 89 |
| 38 | 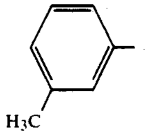 | 0 | H | $CH(CH_3)_2$ | $CH_3$ | $CH_3$ | 83 |
| 39 | 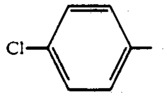 | 0 | H | $CH(CH_3)_2$ | $-CH_2CH_2-$ | | 161 |
| 40 | 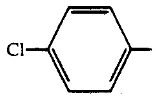 | 1 | H | $CH(CH_3)_2$ | $CH_3$ | $CH_3$ | 79 |

(*) The compounds listed in Examples 14, 17, 18, 20, 22, 23 and 24 are characterized by their 1H-NMR spectra (300 MHz; $CDCl_3$) as follows:

Example 14

δ4.04–3.40 (2 H. d/q $-CH_2-CH=CH_2$) (90 MHz, $CDCl_3$)

Example 17

δ2.52–2.35 (2 H, d/q. $-CH_2-CH=CH_2$)

Example 18

δ2.45–2.24 (2 H, d/q. $-CH_2-CH=CH_2$)

Example 20

δ1.65–1.48 (2 H, m, $-CH_2-C_5H_{11}$), 1.34–1.08 (7H. m. $-CH_2-C(H)(\underline{H})-(\underline{C}H_2)_3-CH_3$), 0.72–0.56 (1H. m. $-CH_2-C(H)(H)-(CH_2)_3-CH_3$)

Example 22

δ1.66–1.47 (2 H, m, $-CH_2-C_5H_{11}$), 1.37–1.10 (7H, m, 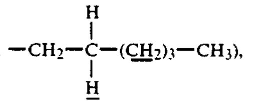

0.71–0.55 (1H, m, 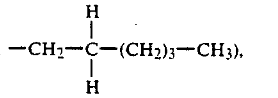

Example 23

δ2.48–2.24 (2 H, d/q, $-CH_2-CH{=}CH_2$)

Preparation of Starting substances of the formula (V):

Example (V-1)

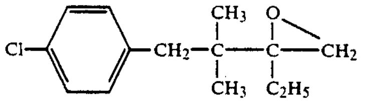

7 8 ml (0.125 mol) of iodomethane are added dropwise to a cooled solution of 10.7 ml (0.13 mol) of dimethyl sulphide in 40 ml of absolute tetrahydrofuran and 80 ml of absolute dimethyl sulphoxide. The mixture is stirred for 16 hours at room temperature (20° C.). A solution of 20.6 g (0.09 mol) of 1-(4-chlorophenyl)-2,2-dimethyl-3pentanone in 100 ml of absolute toluene is added with stirring. The reaction mixture is then cooled to 0°-5° C., and 7.0 g (0.13 mol) of sodium methoxide are added. The mixture is then stirred for a further 15 hours at room temperature, 1000 ml of water are then added to the mixture, the organic phase is separated off, and the aqueous phase is extracted with toluene. The combined organic phases are washed twice with plenty of water, then dried over sodium sulphate and concentrated by stripping off the solvent under reduced pressure. 19.3 g of a colorless oil which according to GC/MS analysis consists of 72% of 2-[2-(4-chlorophenyl)-1,1-dimethyl-ethyl]-2-ethyl-oxirane are obtained. Consequently, the yield is calculated at 65.3% of theory. The product is used for the further reaction without additional purification.

Preparation of Starting substances of the formula (VII):

Example (VII-1)

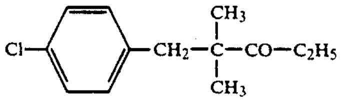

251.6 g (4.5 mol) of potassium hydroxide powder and 15 g of tetrabutylammonium bromide are initially introduced into 100ml of toluene. A solution of 180.5 9 (1.8 mol) of 2-methyl-3-pentanone in 500 ml of toluene is added dropwise with stirring, the temperature being kept below 20° C. A solution of 241.5 g (1.5 mol) of 4-chlorobenzyl chloride in 150 ml of toluene are then added dropwise with stirring and, during this, the temperature is again kept below 20° C. The mixture is then stirred for a further 15 hours at room temperature, the solids are filtered off in vacuo and rinsed with toluene, and the filtrate is evaporated by stripping off the solvent under reduced pressure. The residue is initially subjected to coarse distillation, resulting in 58 g of a product mixture of boiling point 75°-83° C. at 0.1 mbar. This product mixture is then subjected to precision distillation on a split-tube column under reduced pressure.

20.3 g of a colorless liquid which according to GC and NMR consists of 96% of 1-(4-chlorophenyl)-2,2-dimethyl-3-pentanone (b.p.21 mbar 156°-157° C.; 6% of theory) and 9.6 g of an also colorless liquid which according to GC and NMR consists of 96% of 1-(4-chlorophenyl)-2,4-dimethyl-3-pentanone (b.p.21 mbar 163°-165° C.; 2.8% of theory) are obtained.

Example (VII-2)

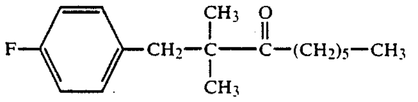

33 g (0.21 mol) of hexylbromide are added dropwise to a suspension of 4.8 g (0.21 mol) of magnesium filings in 80 ml of absolute tetrahydrofuran. When the reaction is complete, a solution of 17.7 g (0.1 mol) of 2,2-dimethyl-3-(4-fluorophenyl)-propanoic acid nitrile in 150 ml of absolute toluene is added dropwise, and the reaction mixture is heated to boiling. Subsequently, sufficient tetrahydrofuran is allowed to distil so that a boiling point of 100° C. is reached, and the mixture is then refluxed for 15 hours. An aqueous ammonium chloride solution is added to the reaction mixture, the organic phase is separated off, and the aqueous phase is extracted twice using ether. The combined organic phases are stirred for 5 hours with 100 ml of 3N hydrochloric acid. After the aqueous phase has been separated off, the organic phase is washed twice using water, dried over sodium sulphate and concentrated under reduced pressure.

19 g (72% of theory) of 2,2-dimethyl-1-(4-fluorophenyl)-3-nonanone are obtained as a pale oil.

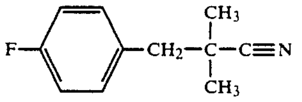

A solution of 168 g (0.86 mol) of 2,2-dmethyl-3-(4-fluorophenyl)-propan-1-al-oxime in 400 ml of acetic anhydride is refluxed for 4 hours. The solution is then cooled, and the solvent is removed by stripping off under reduced pressure. The residue is diluted with 2 l of water, and the resulting solution is extracted three times using dichloromethane. The combined organic phases are washed once with water, dried over sodium sulphate and concentrated by stripping off the solvent under reduced pressure.

150.2 g (98.7% of theory) of 2,2-dimethyl-3-(4-fluorophenyl)-propionitrile are obtained as a pale oil.

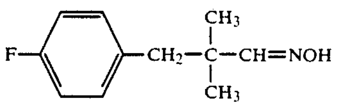

104.25 g (1.5 mol) of hydroxylamine hydrochloride and 123 g (1.5 mol) of sodium acetate are added to a solution of 206 g (1.14 mol) of 2,2-dimethyl-3-(4-fluorophenyl)propanal in 600 ml of water and 600 ml of ethanol, and the mixture is refluxed for 5 hours. The ethanol is then removed by stripping off under reduced pressure, and the aqueous residue is diluted with water and extracted three times using ethyl acetate. The combined organic phases are washed once with water, dried over sodium sulphate and concentrated by stripping off the solvent under reduced pressure.

168 g (75.6% of theory) of 2,2-dimethyl-3-(4-fluorophenyl)-propan-1-al-oxime are obtained as a pale oil which is used directly for the further reaction.

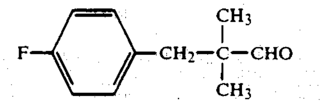

A mixture of 201 g (2.8 mol) of isobutyraldehyde and 289 g (2 mol) of 4-fluorobenzyl chloride are added dropwise in the course of 3 hours into a stirred mixture, maintained at 80° C., of 15 g of tetrabutylammonium bromide and 240 g (6 mol) of sodium hydroxide in 600 ml of water and 600 ml of toluene. The mixture is then stirred for a further 3 hours at 80° C. and diluted with 500 ml of toluene, and the organic phase is separated off, washed once with water and dried over sodium sulphate. The solvent is removed by stripping off under reduced pressure, and the residue is distilled under reduced pressure.

206 g (57.2% of theory) of 2,2-dimethyl-3-(4-fluorophenyl)propanal of b.p.26 mbar 110°-118° C. are obtained.

Use Examples

In the following Use Examples, the compound of the formula below is employed as comparison substance:

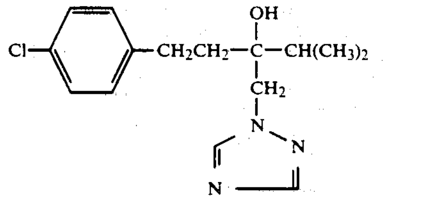

(A)

1-(4-Chloro-phenyl)-4-methyl-3-(1,2,4-triazol-1-yl-methyl)pentan-3-ol (disclosed in EP-OS (European Published Specification) No. 0,040,345).

Example A

Pyricularia test (rice)/protective

Solvent: 12.5 parts by weight of acetone

Emulsifier: 0.3 part by weight of alkyaryl polyglycol ether

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the substances according to the invention listed in Examples (2), (6), (7), (10), (11), (18), (19), (24) and (29) show a considerably better activity than the comparison substance (A).

Example B

Botrytis test (beans)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infested spots on the leaves is evaluated.

In this test, the substances according to the invention listed in Examples (11) and (18) show a better activity than the comparison substance (A).

Example C

Venturia test (apple)/curative

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (Venturia inaequalis). The plants remain in an incubation cabin at 20° C. and 100% relative atmospheric humidity for 1 day and are then placed in a greenhouse. After a given number of hours, the plants are sprayed with the preparation of active compound until dripping wet.

The plants are then placed in a greenhouse at 20° C. and a relative atmospheric humidity of about 70%.

Evaluation is carried out 12 days after the inoculation.

In this test, the substances according to the invention listed in Examples (6), (11), (17) and (18) show a considerably better activity than the comparison substance (A).

Example D

Pyrenophora teres test (barley)/protective

Solvent: 100 parts by weight of dimethylformamide

Emulsifier: 0.25 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, the substances according to the invention listed in Examples (3), (6), (17) and (29) show a considerably better activity than the comparison substance (A).

It will be understood that the specification and examples are illustrative but not limitative of the present invention and that other embodiments within the spirit and scope of the invention will suggest themselves to those skilled in the art.

What is claimed is:

1. A substituted triazolylmethylcarbinol of the formula

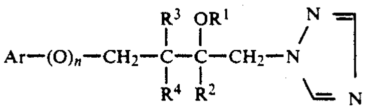

(I)

in which n stands for the numbers 0 or 1,

Ar is phenyl which is optionally substituted by one or two identical or different substituents selected from the group consisting of fluorine, chlorine, bromine, straight-chain or branched alkyl having 1 to 4 carbon atoms, straight-chain or branched halogenoalkyl having 1 to 4 carbon atoms and 1 to 9 halogen atoms and straight-chain or branched halogenoalkoxy having 1 to 4 carbon atoms and 1 to 9 halogen atoms, $R^1$ is hydrogen, straight-chain or branched alkyl having 1 to 8 carbon atoms or is alkenyl having 2 to 4 carbon atoms, $R^2$ is straight-chain or branched alkyl having 1 to 8 carbon atoms, cycloalkyl having 3 to 6 carbon atoms or is straight-chain or branched alkenyl having 2 to 6 carbon atoms, $R^3$ is methyl and $R^4$ is methyl or $R^3$ and $R^4$ together are ethane-1,2-diyl, or an addition product thereof with an acid or metal salt.

2. A compound or addition product thereof according to claim 1, in which $R^1$ is hydrogen, methyl, ethyl, propyl, isopropyl, butyl, isobutyl, sec.-butyl, pentyl or allyl, and $R^2$ is straight-chain or branched alkyl having 1 to 6 carbon atoms, cyclopropyl or alkenyl having 2 to 4 carbon atoms.

3. A compound or addition product thereof according to claim 1, in which n is the number 0, Ar is phenyl, phenyl which is substituted in the 4-position by fluorine, chlorine, bromine, methyl, trifluoromethyl, difluoromethoxy or trifluoromethoxy, or is phenyl which is substituted in the 2- or 3-position by a substituent selected from the group consisting of fluorine, chlorine, bromine, methyl, trifluoromethyl, difluoromethoxy and trifluoromethoxy and is optionally further substituted in the 4-position by fluorine, chlorine, bromine, methyl, trifluoromethyl, difluoromethoxy or trifluoromethoxy, $R^1$ is hydrogen, methyl, ethyl, propyl, isopropyl, butyl, isobutyl, sec.-butyl, pentyl or allyl, $R^2$ is alkyl having 1 to 6 carbon atoms or allyl, $R^3$ is methyl and $R^4$ is methyl.

4. A compound or addition product thereof according to claim 1 in which n is the number 1, Ar is phenyl, phenyl which is substituted in the 4-position by fluorine, chlorine, bromine, methyl, trifluoromethyl, difluoromethoxy or trifluoromethoxy, or is phenyl which is substituted in the 2- or 3-position by a substituent selected from the group consisting of fluorine, chlorine, bromine, methyl, trifluoromethyl, difluoromethoxy and trifluoromethoxy and is optionally further substituted in the 4-position by fluorine, chlorine, bromine, methyl, trifluoromethyl, difluoromethoxy or trifluoromethoxy, $R^1$ is hydrogen, methyl, ethyl, propyl, isopropyl, butyl, isobutyl, sec.-butyl, pentyl or allyl, $R^2$ is alkyl having 1 to 6 carbon atoms, cyclopropyl or allyl, $R^3$ is methyl and $R^4$ is methyl.

5. A compound or addition product thereof according to claim 1, in which n is the number 0, Ar is phenyl, phenyl which is substituted in the 4-position by fluorine, chlorine, bromine, methyl, trifluoromethyl, difluoromethoxy or trifluoromethoxy, or is phenyl which is substituted in the 2- or 3-position by a substituent selected from the group consisting of fluorine, chlorine, bromine, methyl, trifluoromethyl, difluoromethoxy and trifluoromethoxy and is optionally further substituted in the 4-position by fluorine, chlorine, bromine, methyl, trifluoromethyl, difluoromethoxy or trifluoromethoxy, $R^1$ is hydrogen, methyl, ethyl, propyl, isopropyl, butyl, isobutyl, sec.-butyl, pentyl or allyl, $R^2$ is alkyl having 1 to 6 carbon atoms, cyclopropyl or allyl and $R^3$ and $R^4$ together are ethane-1,2-diyl.

6. A compound or addition product thereof according to claim 1, in which n is the number 1, Ar is phenyl, phenyl which is optionally substituted in the 4-position by fluorine, chlorine, bromine, methyl, trifluoromethyl, difluoromethoxy or trifluoromethoxy, or is phenyl which is substituted in the 2- or 3-position by a substituent selected from the group consisting of fluorine, chlorine, bromine, methyl, trifluoromethyl, difluoromethoxy and trifluoromethoxy and is optionally further substituted in the 4-position by fluorine, chlorine, bromine, methyl, trifluoromethyl, difluoromethoxy or trifluoromethoxy, $R^1$ is hydrogen, methyl, ethyl, ethyl, propyl, isopropyl, butyl, isobutyl, sec.-butyl, pentyl or allyl, $R^2$ is alkyl having 1 to 6 carbon atoms, cyclopropyl or allyl and $R^3$ and $R^4$ together are ethane-1,2-diyl.

7. A compound according to claim 1, wherein such compound is 6-(3,4-dichlorophenyl)-5,5-dimethyl-4-(1,2,4-triazol-1-yl-methyl)-1-hexen-4-ol of the formula

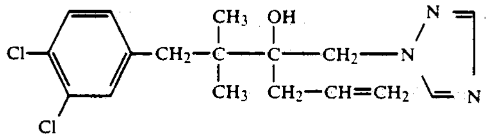

or an addition product thereof with an acid or metal salt.

8. A compound according to claim 1, wherein such compound is 1-(4-chlorophenyl)-2,2-dimethyl-3-(1,2,4-triazol-1-yl-methyl)-heptan-3-ol of the formula

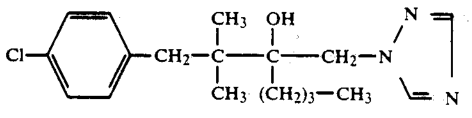

or an addition product thereof with an acid or metal salt.

9. A compound according to claim 1, wherein such compound is 6-(2,4-dichlorophenyl)-5,5-dimethyl-4-(1,2,4-triazol-1-yl-methyl)-1-hexen-4-ol of the formula

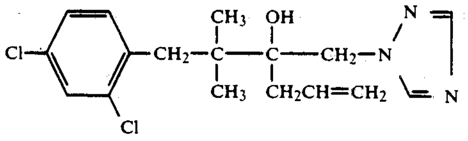

or an addition product thereof with an acid or metal salt.

10. A compound according to claim 1, wherein such compound is 1 (4-chlorophenyl)-2,2,4-trimethyl-3-(1,2,4-triazol-1-yl-methyl)-pentan-3-ol of the formula

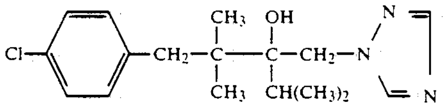

or an addition product thereof with an acid or metal salt.

11. A compound according to claim 1, wherein such compound is 1-(4-fluorophenyl)-2,2,4-trimethyl-3-(1,2,4-triazol-1-yl-methyl)-pentan-3-ol of the formula

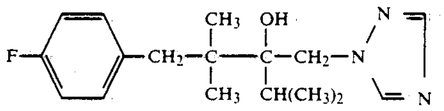

or an addition product thereof with an acid or metal salt.

12. A fungicidal composition comprising a fungicidally effective amount of a compound or addition product thereof according to claim 1 and an inert diluent.

13. A method of combating fungi which comprises applying to such fungi or to a fungus habitat a fungicidally effective amount of a compound or addition product thereof according to claim 2.

14. The method according to claim 13, wherein such compound is 6-(3,4-dichlorophenyl)-5,5-dimethyl-4-(1,2,4-triazol-1-yl-methyl)-1-hexen-4-ol,
1-(4-chlorophenyl)-2,2-dimethyl-3-(1,2,4-triazol-1-yl-methyl)-heptan-3-ol,
6-(2,4-dichlorophenyl)-5,5-dimethyl-4-(1,2,4-triazol-1yl-methyl)-1-hexen-4-ol,
1-(4-chlorophenyl)-2,2,4-trimethyl-3-(1,2,4-triazol-1-yl-methyl)-pentan-3-ol, or
1-(4-fluorophenyl)-2,2,4-trimethyl-3-(1,2,4-triazol-1-yl-methyl)-pentan-3-ol, or an addition product thereof with an acid or metal salt.

* * * * *

UNITED STATES PATENT AND TRADEMARK OFFICE
CERTIFICATE OF CORRECTION

PATENT NO. : 4,994,480

DATED : February 19, 1991

INVENTOR(S) : Karl H. Buchel, et al

It is certified that error appears in the above-identified patent and that said Letters Patent is hereby corrected as shown below:

Title Page [75] Inventors: 3rd Inventor delete " Hannsler " and substitute -- Hanssler --

Signed and Sealed this

First Day of June, 1993

Attest:

MICHAEL K. KIRK

*Attesting Officer*

*Acting Commissioner of Patents and Trademarks*